(12) United States Patent
Radhakrishnan et al.

(10) Patent No.: US 7,368,260 B2
(45) Date of Patent: May 6, 2008

(54) METHODS OF SYNTHESIZING INSULIN POLYPEPTIDE-OLIGOMER CONJUGATES, AND PROINSULIN POLYPEPTIDE-OLIGOMER CONJUGATES AND METHODS OF SYNTHESIZING SAME

(75) Inventors: Balasingam Radhakrishnan, Chapel Hill, NC (US); Richard Soltero, Holly Springs, NC (US); Nnochiri N. Ekwuribe, Cary, NC (US)

(73) Assignee: Biocon Limited (IN)

( * ) Notice: Subject to any disclaimer, the term of this patent is extended or adjusted under 35 U.S.C. 154(b) by 0 days.

(21) Appl. No.: 11/174,982

(22) Filed: Jul. 5, 2005

(65) Prior Publication Data

US 2005/0277580 A1    Dec. 15, 2005

Related U.S. Application Data

(62) Division of application No. 10/036,744, filed on Dec. 21, 2001, now Pat. No. 6,913,903.

(60) Provisional application No. 60/318,197, filed on Sep. 7, 2001.

(51) Int. Cl.
*A61K 38/28* (2006.01)

(52) U.S. Cl. .......................... 435/68.1; 514/3; 530/303

(58) Field of Classification Search .................. None
See application file for complete search history.

(56) References Cited

U.S. PATENT DOCUMENTS

| | | | | |
|---|---|---|---|---|
| 6,913,903 | B2 * | 7/2005 | Soltero et al. | 435/68.1 |
| 7,166,571 | B2 * | 1/2007 | Soltero et al. | 514/3 |
| 2003/0228652 | A1 * | 12/2003 | Radhakrishnan et al. | 435/68.1 |

* cited by examiner

*Primary Examiner*—Christopher Tate
*Assistant Examiner*—Roy Teller
(74) *Attorney, Agent, or Firm*—Marianne Fuierer; Moore & Van Allen PLLC

(57) ABSTRACT

Methods for synthesizing proinsulin polypeptides are described that include a contacting a proinsulin polypeptide including an insulin polypeptide coupled to one or more peptides by peptide bond(s) capable of being cleaved to yield the insulin polypeptide with an oligomer under conditions sufficient to couple the oligomer to the insulin polypeptide portion of the proinsulin polypeptide and provide a proinsulin polypeptide-oligomer conjugate, and cleaving the one or more peptides from the proinsulin polypeptide-oligomer conjugate to provide the insulin polypeptide-oligomer conjugate. Methods of synthesizing proinsulin polypeptide-oligomer conjugates are also described as are proinsulin polypeptide-oligomer conjugates. Methods of synthesizing C-peptide polypeptide-oligomer conjugates are also described.

45 Claims, 16 Drawing Sheets

FIG. 8. PRODUCT OF CARBOXYPEPTIDASE B CLEAVAGE OF B-29 ACYLATED INSULIN (Arg$^{31}$) HEXYL-PEG7

METHODS OF SYNTHESIZING INSULIN POLYPEPTIDE-OLIGOMER CONJUGATES, AND PROINSULIN POLYPEPTIDE-OLIGOMER CONJUGATES AND METHODS OF SYNTHESIZING SAME

RELATED APPLICATION

This application is a divisional application, and claims priority to U.S. patent application Ser. No. 10/036,744, filed Dec. 21, 2001, and issued on Jul. 5, 2005 as U.S. Pat. No. 6,913,903, entitled "METHODS OF SYNTHESIZiNG INSULiN POLYPEPTIDE-OLIGOMER CONJUGATES, AND PROINSULIN OF POLYPEPTIDE-OLIGOMER CONJUGATES AND METHODS OF SYNTHESIZING SAME", naming Balasingam Radhakrishnan, Richard Soltero and Nnochiri N. Ekwuribe as inventors, which claims priority to U.S. Provisional Application No. 60/318,197, filed Sep. 7, 2001. The contents of the patent applications are incorporated herein by reference in their entirety, and the benefit of the filing date of the patent application is hereby claimed for all purposes that are legally served by such claim for the benefit of the filing date.

FIELD OF THE INVENTION

The present invention relates to insulin conjugates, methods of synthesizing such conjugates, and methods of treating diseases including diabetes therewith.

BACKGROUND OF THE INVENTION

The polypeptide insulin is the primary hormone responsible for controlling the transport, utilization and storage of glucose in the body. The β-cells of the pancreatic islets secrete a single chain precursor of insulin, known as proinsulin. Proteolysis of proinsulin results in removal of certain basic amino acids in the proinsulin chain and the connecting or C-peptide and provides the biologically active polypeptide insulin.

The insulin molecule has been highly conserved in evolution and generally consists of two chains of amino acids linked by disulfide bonds. In the natural human, two-chain insulin molecule (mw 5,800 Daltons), the A-chain is composed of 21 amino acid residues and has glycine at the amino terminus; and the B-chain has 30 amino acid residues and phenylalanine at the amino terminus.

Insulin may exist as a monomer or may aggregate into a dimer or a hexamer formed from three of the dimers. Biological activity, i.e., the ability to bind to receptors and stimulate the biological actions of insulin, resides in the monomer.

Diabetes is a biological disorder involving improper carbohydrate metabolism. Diabetes results from insufficient production of or reduced sensitivity to insulin. In persons with diabetes, the normal ability to use glucose is inhibited, thereby increasing blood sugar levels (hyperglycemia). As glucose accumulates in the blood, excess levels of sugar are excreted in the urine (glycosuria). Other symptoms of diabetes include increased urinary volume and frequency, thirst, itching, hunger, weight loss, and weakness.

There are two varieties of diabetes. Type I is insulin-dependent diabetes mellitus, or IDDM. IDDM was formerly referred to as "juvenile onset diabetes." In IDDM, insulin is not secreted by the pancreas and must be provided from an external source. Type II or adult-onset diabetes can ordinarily be controlled by diet, although in some advanced cases insulin is required.

Before the isolation of insulin in the 1920s, most patients died within a short time after onset. Untreated diabetes leads to ketosis, the accumulation of ketones, products of fat breakdown, in the blood. This is followed by the accumulation of acid in the blood (acidosis) with nausea and vomiting. As the toxic products of disordered carbohydrate and fat metabolism continue to build up, the patient goes into a diabetic coma, which leads to death.

The use of insulin as a treatment for diabetes dates to 1922, when Banting et al. ("Pancreatic Extracts in the Treatment of Diabetes Mellitus," *Can. Med. Assoc. J.*, 12:141-146 (1922)) showed that the active extract from the pancreas had therapeutic effects in diabetic dogs. In that same year, treatment of a diabetic patient with pancreatic extracts resulted in a dramatic, life-saving clinical improvement.

Until recently, bovine and porcine insulin were used almost exclusively to treat diabetes in humans. Today, however, numerous variations in insulin between species are known. Each variation differs from natural human insulin in having amino acid substitution(s) at one or more positions in the A- and/or B-chain. Despite these differences, most mammalian insulin has comparable biological activity. The advent of recombinant technology allows commercial scale manufacture of human insulin (e.g., Humulin™ insulin, commercially available from Eli Lilly and Company, Indianapolis, Ind.) or genetically engineered insulin having biological activity comparable to natural human insulin.

Treatment of diabetes typically requires regular injections of insulin. Due to the inconvenience of insulin injections, massive efforts to improve insulin administration and bioassimilation have been undertaken.

Attempts have been made to deliver insulin by oral administration. The problems associated with oral administration of insulin to achieve euglycemia in diabetic patients are well documented in pharmaceutical and medical literature. Digestive enzymes in the gastrointestinal tract rapidly degrade insulin, resulting in biologically inactive breakdown products. In the stomach, for example, orally administered insulin undergoes enzymatic proteolysis and acidic degradation. Comparable proteolytic breakdown of insulin occurs in the intestine. In the lumen, insulin is attacked by a variety of enzymes including gastric and pancreatic enzymes, exo- and endopeptidases, and brush border peptidases. Even if insulin survives this enzymatic attack, the biological barriers that must be traversed before insulin can reach its receptors in vivo may limit its bioavailability after oral administration of insulin. For example, insulin may possess low membrane permeability, limiting its ability to pass from the intestinal lumen into the bloodstream.

Some efforts to provide an oral form of insulin have focused on providing insulin-oligomer conjugates. Human insulin and many closely related insulins that are used therapeutically contain three amino acid residues bearing free primary amino groups. All three primary amino groups, namely the N-termini (alpha amino groups) of the A and B chains ($Gly^{A1}$ and $Phe^{B1}$) and the epsilon-amino group of $Lys^{B29}$, may be modified by conjugation with oligomers. Depending on the reaction conditions, N-acylation of an unprotected insulin leads to a complex mixture of mono-, di-, and tri-conjugates (e.g., insulin mono-conjugated at $Gly^{A1}$, insulin mono-conjugated at $Phe^{B1}$, insulin mono-conjugated at $Lys^{B29}$, insulin di-conjugated at $Gly^{A1}$ and $Phe^{B1}$, insulin di-conjugated at $Gly^{A1}$ and $Lys^{B29}$, insulin di-conjugated at $Phe^{B1}$ and $Lys^{B29}$, and insulin tri-conjugated at $Gly^{A1}$, $Phe^{B1}$, and $Lys^{B29}$). When a particular conjugate, for example insulin mono-conjugated at $Lys^{B29}$, is desired, it can be burdensome and/or expensive to separate (or purify) such a complex mixture of conjugates to obtain the desired conjugate.

As a result, various efforts have been undertaken to selectively synthesize the desired insulin conjugate. For example, Muranishi and Kiso, in Japanese Patent Application 1-254,699, propose a five-step synthesis for preparing fatty acid insulin derivatives. The A1- and B1-amino groups of insulin are protected (or blocked) with p-methoxybenzoxy carbonyl azide (pMZ). After acylation with a fatty acid ester, the protection (blocking) groups are removed to provide insulin mono-acylated at Lys(B29) with a fatty acid. As another example, U.S. Pat. No. 5,750,497 to Havelund et al. proposes treating human insulin with a Boc-reagent (e.g. di-tert-butyl dicarbonate) to form (A1,B1)-diBoc human insulin, i.e., human insulin in which the N-terminal end of both the A- and B-chains are protected by a Boc-group. After an optional purification, e.g. by HPLC, a lipophilic acyl group is introduced in the ε-amino group of $LYS^{B29}$ by allowing the product to react with a N-hydroxysuccinimide ester of the formula X—OSu wherein X is the lipophilic acyl group to be introduced. In the final step, trifluoroacetic acid is used to remove the Boc-groups and the product, $N^{\epsilon B29}$—X human insulin, is isolated.

Various other efforts have been undertaken to preferentially synthesize the desired insulin conjugate to provide a mixture of conjugates in which the desired insulin conjugate is the preferred product. For example, U.S. Pat. No. 5,646,242 to Baker et al. proposes a reaction that is performed without the use of amino-protecting groups. Baker proposes the reaction of an activated fatty ester with the ε-amino group of insulin under basic conditions in a polar solvent. The acylation of the ε-amino group is dependent on the basicity of the reaction. At a pH greater than 9.0, the reaction preferentially acylates the ε-amino group of B29-lysine over the α-amino groups. Examples 1 through 4 report reaction yields of the mono-conjugated insulin as a percentage of the initial amount of insulin between 67.1% and 75.5%. In Example 5, Baker also proposes acylation of human proinsulin with N-succinimidyl palmitate. The exact ratios of ε-amino acylated species to α-amino acylated species were not calculated. The sum of all ε-amino acylated species within the chromatogram accounted for 87-90% of the total area, while the sum of all related substances (which would presumably include any α-amino acylated species) accounted for <7% of the total area, for any given point in time.

It is desirable to provide methods of site specifically synthesizing desired, particular insulin-oligomer conjugates that may be less burdensome and/or more cost effective than the conventional methods described above.

SUMMARY OF THE INVENTION

When compared to the conventional schemes described above, embodiments of the present invention may provide a commercially less expensive and/or higher yielding manufacturing scheme for producing insulin-oligomer conjugates where site-specific conjugation is desirable (e.g., where it is desirable to provide an insulin mono-conjugate having the oligomer coupled to the B-29 Lys of the insulin molecule). Unlike the conventional schemes described above, which propose selective conjugation of insulin by blocking the N-termini of the insulin with compounds such as p-methoxybenzoxy carbonyl azide (Muranishi and Kiso) or by attempting to control the reaction conditions to reduce but not eliminate conjugation at the N-termini of the insulin (Baker), embodiments of the present invention couple the oligomer to the B-29 Lys of proinsulin or of artificial proinsulin (e.g., proinsulin coupled at the N-terminus of its B-chain to a leader peptide). The C-peptide (and leader peptide, if present) is then cleaved from the proinsulin-oligomer conjugate to provide insulin mono-conjugated at B-29 Lys with the oligomer. Embodiments of the present invention may provide high site specificity for B-29 Lys modification. Methods according to embodiments of the present invention utilizing proinsulin polypeptides may provide high conversion B-29 modified product, for example with yields as high as 80% or greater, compared with that obtained via conventional insulin pathways.

According to embodiments of the present invention, a method of synthesizing an insulin polypeptide-oligomer conjugate includes contacting a proinsulin polypeptide comprising an insulin polypeptide coupled to one or more peptides by peptide bond(s) capable of being cleaved to yield the insulin polypeptide with an oligomer under conditions sufficient to couple the oligomer to the insulin polypeptide portion of the proinsulin polypeptide and provide a proinsulin polypeptide-oligomer conjugate, and cleaving the one or more peptides from the proinsulin polypeptide-oligomer conjugate to provide the insulin polypeptide-oligomer conjugate.

According to other embodiments of the present invention, a method of synthesizing an insulin polypeptide-acyl oligomer conjugate comprising enzymatically cleaving one or more peptides from a proinsulin polypeptide-acyl oligomer conjugate to provide the insulin polypeptide-acyl oligomer conjugate.

According to other embodiments of the present invention, a method of synthesizing a proinsulin polypeptide-oligomer conjugate includes contacting a proinsulin polypeptide comprising an insulin polypeptide coupled to one or more peptides by peptide bond(s) capable of being cleaved to yield the insulin polypeptide with an oligomer under conditions sufficient to couple the oligomer to the insulin polypeptide portion of the proinsulin polypeptide and provide the proinsulin polypeptide-oligomer conjugate.

According to still other embodiments of the present invention, a proinsulin polypeptide-oligomer conjugate includes a proinsulin polypeptide including an insulin polypeptide, and an oligomer coupled to the insulin polypeptide portion of the proinsulin polypeptide.

According to yet other embodiments of the present invention, a method of synthesizing a C-peptide polypeptide-oligomer conjugate includes contacting a pro-C-peptide polypeptide comprising a C-peptide polypeptide coupled to one or more peptides by peptide bond(s) that are cleavable to yield the C-peptide polypeptide with an oligomer under conditions sufficient to couple the oligomer to the C-peptide polypeptide portion of the pro-C-peptide polypeptide and provide a pro-C-peptide polypeptide-oligomer conjugate, and cleaving the one or more peptides from the pro-C-peptide polypeptide-oligomer conjugate to provide the C-peptide polypeptide-oligomer conjugate.

DETAILED DESCRIPTION OF PREFERRED EMBODIMENTS

Figure 1:
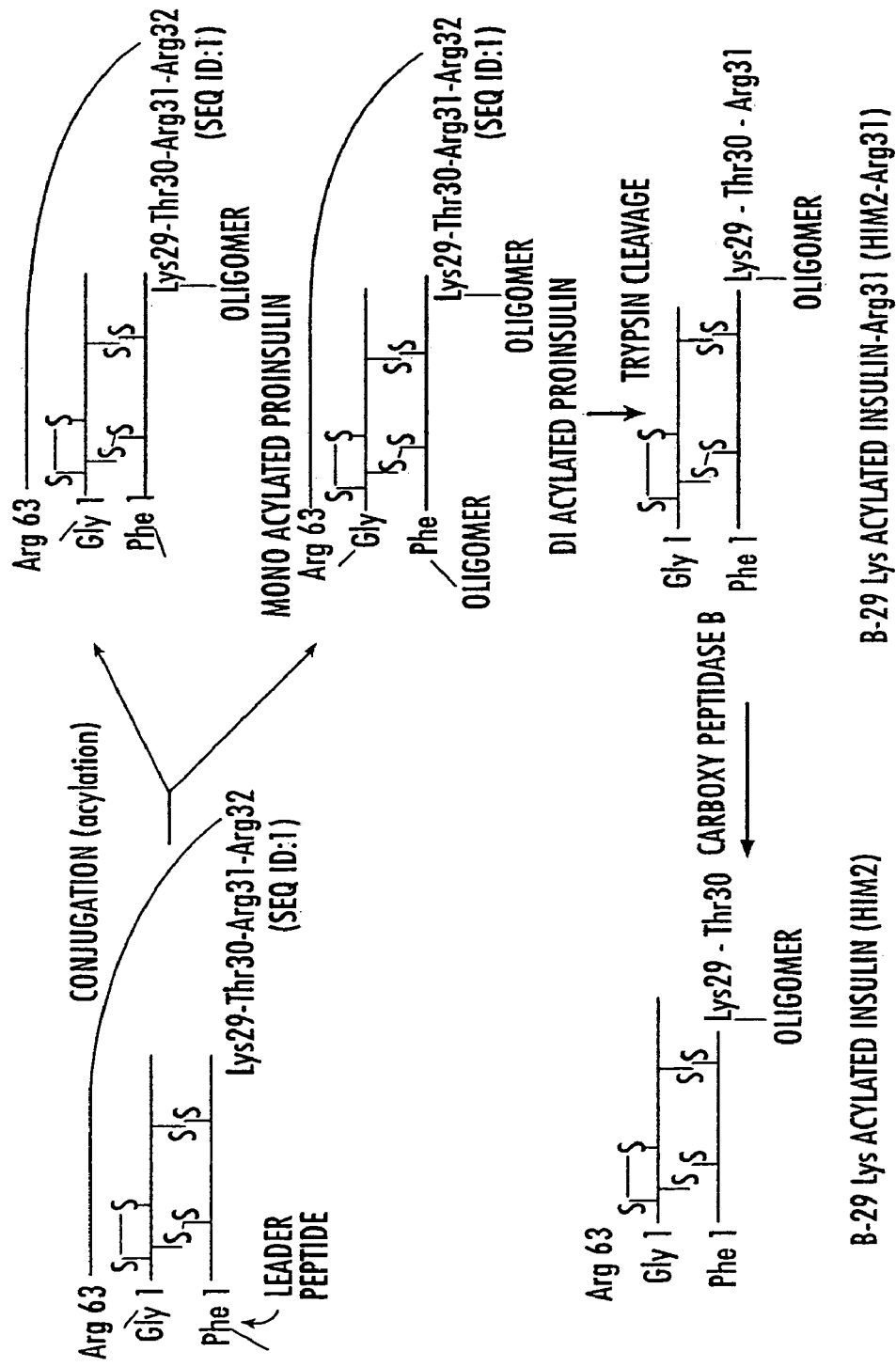
FIG. 1 illustrates embodiments of a synthesis route for preparation of B-29 Lys modified insulin using a proinsulin having a leader peptide.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

All amino acid abbreviations used in this disclosure are those accepted by the United States Patent and Trademark Office as set forth in 37 C.F.R. § 1.822(b).

As used herein, the term "between" when used to describe varous ranges should be interpreted to include the end-points of the described ranges.

As used herein, the term "substantially monodispersed" is used to describe a mixture of compounds wherein at least about 95 percent of the compounds in the mixture have the same molecular weight.

As used herein, the term "monodispersed" is used to describe a mixture of compounds wherein about 100 percent of the compounds in the mixture have the same molecular weight.

As used herein, the term "insulin polypeptide" means a polypeptide possessing at least some of the biological activity of insulin (e.g., ability to affect the body through insulin's primary mechanism of action). For example, an insulin polypeptide may be a polypeptide such as insulin having an A-chain polypeptide and a B-chain polypeptide coupled to the A-chain polypeptide by disulfide bonds. In various embodiments of the present invention, the insulin polypeptide preferably possesses a majority of the biological activity of insulin, more preferably possesses substantially all of the biological activity of insulin, and most preferably possesses all of the biological activity of insulin.

As used herein, the term "proinsulin polypeptide" means an insulin polypeptide that is coupled to one or more peptides (e.g., leader peptides and/or connecting or C-peptides) by peptide bond(s) that are capable of cleavage in vitro or in vivo. For example, a proinsulin polypeptide may include an insulin polypeptide, such as insulin, having an A-chain polypeptide coupled to a B-chain polypeptide by bonds such as disulfide bonds, and a connecting peptide coupled to the C-terminus of the B-chain polypeptide and coupled to the N-terminus of the A-chain polypeptide by peptide bonds that are capable of cleavage in vitro and/or in vivo. As another example, a proinsulin polypeptide may include an insulin polypeptide, such as insulin, having an A-chain polypeptide coupled to a B-chain polypeptide by bonds such as disulfide bonds, a connecting peptide coupled to the C-terminus of the B-chain polypeptide and coupled to the N-terminus of the A-chain polypeptide by peptide bonds that are capable of cleavage in vitro and/or in vivo, and a leader peptide coupled to the N-terminus of the B-chain polypeptide. Exemplary proinsulin polypeptides include, but are not limited to, proinsulin, proinsulin analogs, proinsulin fragments, proinsulin analog fragments, or any of proinsulin, proinsulin analogs, proinsulin fragments, proinsulin analog fragments having a leader peptide; preproinsulin, preproinsulin anaolgs, preproinsulin fragments, preproinsulin fragment analogs, miniproinsulin, and fusion proteins.

As used herein, the term "insulin" means the insulin of one of the following species: human, cow, pig, sheep, horse, dog, chicken, duck or whale, provided by natural, synthetic, or genetically engineered sources. In various embodiments of the present invention, insulin is preferably human insulin.

As used herein, the term "insulin analog" means insulin wherein one or more of the amino acids have been replaced while retaining some or all of the activity of the insulin. The analog is described by noting the replacement amino acids with the position of the replacement as a superscript followed by a description of the insulin. For example, "Pro$^{B29}$ insulin, human" means that the lysine typically found at the B29 position of a human insulin molecule has been replaced with proline.

Insulin analogs may be obtained by various means, as will be understood by those skilled in the art. For example, certain amino acids may be substituted for other amino acids in the insulin structure without appreciable loss of interactive binding capacity with structures such as, for example, antigen-binding regions of antibodies or binding sites on substrate molecules. As the interactive capacity and nature of insulin defines its biological functional activity, certain amino acid sequence substitutions can be made in the amino acid sequence and nevertheless remain a polypeptide with like properties.

In making such substitutions, the hydropathic index of amino acids may be considered. The importance of the hydropathic amino acid index in conferring interactive biologic function on a polypeptide is generally understood in the art. It is accepted that the relative hydropathic character of the amino acid contributes to the secondary structure of the resultant polypeptide, which in turn defines the interaction of the protein with other molecules, for example, enzymes, substrates, receptors, DNA, antibodies; antigens, and the like. Each amino acid has been assigned a hydropathic index on the basis of its hydrophobicity and charge characteristics as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). As will be understood by those skilled in the art, certain amino acids may be substituted by other amino acids having a similar hydropathic index or score and still result in a polypeptide with similar biological activity, i.e., still obtain a biological functionally equivalent polypeptide. In making such changes, the substitution of amino acids whose hydropathic indices are within ±2 of each other is preferred, those which are within ±1 of each other are particularly preferred, and those within ±0.5 of each other are even more particularly preferred.

It is also understood in the art that the substitution of like amino acids can be made effectively on the basis of hydrophilicity. U.S. Pat. No. 4,554,101, the disclosure of which is incorporate herein in its entirety, provides that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (±3.0); aspartate (+3.0±1); glutamate (+3.0±1); seine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). As is understood by those skilled in the art, an amino acid can be substituted for another having a similar hydrophilicity value and still obtain a biologically equivalent, and in particular, an immunologically equivalent polypeptide. In such changes, the substitution of amino acids whose hydrophilicity values are within ±2 of each other is preferred, those which are within ±1 of each other are particularly preferred, and those within ±0.5 of each other are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions (i.e., amino acids that may be interchanged without significantly altering the biological activity of the polypeptide) that take various of the foregoing characteristics into consideration are well known to those of skill in the art and include, for example: arginine and lysine; glutamate and aspartate; serine and threonine; glutamine and asparagine; and valine, leucine and isoleucine.

As will be understood by those skilled in the art, insulin analogs may be prepared by a variety of recognized peptide synthesis techniques including, but not limited to, classical (solution) methods, solid phase methods, semi-synthetic methods, and recombinant DNA methods.

Examples of human insulin analogs include, but are not limited to, Gly$^{A21}$ insulin, human; Gly$^{A21}$ Gln$^{B3}$ insulin, human; Ala$^{A21}$ insulin, human; Ala$^{A21}$ Gln$^{B3}$ insulin, human; Gln$^{B3}$ insulin, human; Gln$^{B30}$ insulin, human; Gly$^{A21}$ Glu$^{B30}$ insulin, human; Gly$^{A21}$ Gln$^{B3}$ Glu$^{B30}$ insulin, human; Gln$^{B3}$ Glu$^{B30}$ insulin, human; Asp$^{B28}$ insulin, human; Lys$^{B28}$ insulin, human; Leu$^{B28}$ insulin, human; Val$^{B28}$ insulin, human; Ala$^{B28}$ insulin, human; Asp$^{B28}$ Pro$^{B29}$ insulin, human; Lys$^{B28}$ Pro$^{B29}$ insulin, human; Leu$^{B28}$ Pro$^{B29}$ insulin, human; Val$^{B28}$ Pro$^{B29}$ insulin, human Ala$^{B28}$ Pro$^{B29}$ insulin, human.

As used herein, the term "insulin fragment" means a segment of the amino acid sequence found in the insulin that retains some or all of the activity of the insulin. Insulin fragments are denoted by stating the position(s) in an amino acid sequence followed by a description of the amino acid. For example, a "B25-B30 human insulin" fragment would be the six amino acid sequence corresponding to the B25, B26, B27, B28, B29 and B30 positions in the human insulin amino acid sequence.

As used herein, the term "insulin fragment analog" means a segment of the amino acid sequence found in the insulin molecule wherein one or more of the amino acids in the segment have been replace while retaining some or all of the activity of the insulin.

As used herein, the term "proinsulin" means the proinsulin of one of the following species: human, cow, pig, sheep, horse, dog, chicken, duck or whale, provided by natural, synthetic, or genetically engineered sources. In general, proinsulin consist of insulin having a C-peptide connecting the N-terminus of the A chain of the insulin to the C-terminus of the B chain of the insulin. In various embodiments of the present invention described herein, the proinsulin is preferably human proinsulin.

As used herein, the term "proinsulin analog" means proinsulin wherein one or more of the amino acids in proinsulin have been replaced as described above with respect to insulin analogs while retaining some or all of the activity of the insulin portion of the proinsulin. The analog is described by noting the replacement amino acids with the position of the replacement as a superscript followed by a description of the proinsulin. For example, "Pro$^{B29}$ proinsulin, human" means that the lysine typically found at the B29 position of a human proinsulin molecule has been replaced with proline.

As used herein, the term "proinsulin fragment" means a segment of the amino acid sequence found in the proinsulin that retains some or all of the biological activity of the insulin, insulin analog or insulin fragment portion of the proinsulin fragment. Proinsulin fragments are denoted by stating the position(s) in an amino acid sequence followed by a description of the amino acid. For example, a "B25-B35 human proinsulin" fragment would be the eleven amino acid sequence corresponding to the B25, B26, B27, B28, B29, B30, B31, B32, B33, B34 and B35 positions in the human proinsulin amino acid sequence.

As used herein, the term "proinsulin fragment analog" means a segment of the amino acid sequence found in proinsulin molecule wherein one or more of the amino acids in the segment have been replaced as described above with reference to insulin analogs while retaining some or all of the activity of the insulin, insulin analog, insulin fragment, or insulin fragment analog portion of the proinsulin fragment.

As used herein, the term "preproinsulin" means the preproinsulin of one of the following species: human, cow, pig, sheep, horse, dog, chicken, duck or whale, provided by natural, synthetic, or genetically engineered sources. In general, preproinsulin is a single chain polypeptide (e.g., a polypeptide having a leader peptide coupled to the N-terminus of the B-chain of the insulin and having the C-terminus of the B-chain coupled to the N-terminus of the A-chain by a connecting peptide) in which the A-chain is coupled to the B-chain by, for example, disulfide bonds. In the various embodiments of the present invention described herein, the preproinsulin is preferably human preproinsulin.

As used herein, the term "preproinsulin analog" means preproinsulin wherein one or more of the amino acids in preproinsulin have been replaced as described above with respect to insulin analogs while retaining some or all of the activity of the insulin or insulin analog portion of the preproinsulin analog. The analog is described by noting the replacement amino acids with the position of the replacement as a superscript followed by a description of the insulin.

As used herein, the term "preproinsulin fragment" means a segment of the amino acid sequence found in preproinsulin that retains some or all of the biological activity of the insulin or insulin fragment portion of the preproinsulin fragment. Preproinsulin fragments are denoted by stating the position(s) in an amino acid sequence followed by a description of the amino acid.

As used herein, the term "preproinsulin fragment analog" means a segment of the amino acid sequence found in preproinsulin molecule wherein one or more of the amino acids in the segment have been replaced as described above with reference to insulin analogs while retaining some or all of the activity of the insulin, insulin analog, insulin fragment or insulin fragment analog portion of the preproinsulin fragment analog.

As used herein, the term "miniproinsulin" refers to a single-chain insulin propolypeptide having an A-chain polypeptide and a B-chain polypeptide, where the N— or C-terminus of the A-chain is coupled to the C— or N-terminus of the B-chain by a connecting peptide having between a lower limit of 1, 2, 3, 4, 5, 6, 7, 8, or 9 and an upper limit of 2, 3, 4, 5, 6, 7, 8, 9, or 10 amino acid residues, and wherein the A-chain polypeptide is coupled to the B-chain polypeptide by bonds, such as disulfide bonds. Miniproinsulins may be various miniproinsulins as will be understood by those skilled in the art including, but not limited to, those described in U.S. Pat. No. 5,157,021 to Balschmidt et al. and U.S. Pat. No. 5,202,415 to Jonassen et al., the disclosures of each of which are incorporated by reference herein in their entireties.

As used herein, the term "C-peptide" means a peptide having the amino acid sequence of the C-peptide of the proinsulin of one of the following species: human, monkey, cow, pig, sheep, horse, dog, chicken, duck or whale, provided by natural, synthetic, or genetically engineered sources. In various embodiments of the present invention described herein, the C-peptide is preferably human C-peptide.

As used herein, the term "C-peptide analog" means C-peptide wherein one or more of the amino acids in the C-peptide have been replaced as described above with respect to insulin analogs while retaining some or all of the biological activity of the C-peptide. Preferably, the C-peptide analog comprises the pentapeptide segment at the C-terminus of a C-peptide and/or the nonapeptide segment found at positions 11-19 of a C-peptide. When the C-peptide analog comprises the pentapeptide segment, the pentapeptide segment is preferably at the C-terminus of the C-peptide analog. More preferably, the C-peptide analog comprises the tetrapeptide segment at the C-terminus of a C-peptide and/or the nonapeptide segment found at positions 11-19 of a C-peptide. When the C-peptide analog comprises the tetrapeptide segment, the tetrapeptide segment is preferably at the C-terminus of the C-peptide analog. The nonapeptide segment found at positions 11-19 of a C-peptide described above is preferably the nonapeptide segment fount at positions 11-19 of human C-peptide.

As used herein, the term "C-peptide fragment" means a segment of the amino acid sequence of C-peptide that retains some, substantially all, or all of the biological activity of the C-peptide. Preferably, the C-peptide fragment comprises the pentapeptide segment at the C-terminus of a C-peptide and/or the nonapeptide segment found at positions 11-19 of a C-peptide. When the C-peptide fragment comprises the pentapeptide segment, the pentapeptide segment is preferably at the C-terminus of the C-peptide fragment. More preferably, the C-peptide fragment comprises the tetrapeptide segment at the C-terminus of a C-peptide and/or the nonapeptide segment found at positions 11-19 of a C-peptide. When the C-peptide fragment comprises the tetrapeptide segment, the tetrapeptide segment is preferably at the C-terminus of the C-peptide fragment. Still more preferably, the C-peptide fragment consists of a peptide selected from the group consisting of the petapetide segment of the C-terminus of a C-peptide, the nonapeptide segment found at positions 11-19 of a C-peptide, and the terapeptide segment of the C-terminus of a C-peptide. The nonapeptide segment found at positions 11-19 of a C-peptide described above is preferably the nonapeptide segment fount at positions 11-19 of human C-peptide.

As used herein, the term "C-peptide fragment analog" means a segment of the amino acid sequence of C-peptide wherein one or more of the amino acids in the segment have been replaced as described above with reference to insulin analogs while retaining some, substantially all, or all of the biological activity of the insulin. Preferably, the C-peptide fragment analog comprises the pentapeptide segment at the C-terminus of a C-peptide and/or the nonapeptide segment found at positions 11-19 of a C-peptide. When the C-peptide fragment analog comprises the pentapeptide segment, the pentapeptide segment is preferably at the C-terminus of the C-peptide fragment analog. More preferably, the C-peptide fragment analog comprises the tetrapeptide segment at the C-terminus of a C-peptide and/or the nonapeptide segment found at positions 11-19 of a C-peptide. When the C-peptide fragment analog comprises the tetrapeptide segment, the tetrapeptide segment is preferably at the C-terminus of the C-peptide fragment analog. The nonapeptide segment found at positions 11-19 of a C-peptide described above is preferably the nonapeptide segment fount at positions 11-19 of human C-peptide.

As used herein, the term "C-peptide polypeptide" means a polypeptide having a therapeutic utility and biological activity similar to the therapeutic utility and biological functionality for C-peptides and/or C-peptide fragments described in J. Wahren et al., "Role of C-peptide in Human Physiology," *Am. J. Physiol. Endocrinol. Metab.,* 278: E759-E768 (2000) and/or T. Forst et al., "New Aspects on Biological Activity of C-peptide in IDDM Patients," *Exp. Clin. Endocrinol. Diabetes,* 106: 270-276 (1998), the disclosures of which are incorporated herein by reference in their entireties. For example, C-peptide polypeptides have therapeutic utility that includes, but is not limited to, decreased glomerular hyperfiltration, augmented whole body and/or skeletal muscle glucose utilization, improved autonomic nerve function, and/or a redistribution of microvascular skin blood flow. C-peptide polypeptides have biological activity that includes, but is not limited to, the ability to stimulate $Na^+$-$K^+$-ATPase acitivity, the ability to stimulate endotheial nitric oxide synthase activity, and/or the ability to bind specifically to cell surfaces (e.g., at a G-protein-coupled surface receptor) with subsequent activation of $Ca^{2+}$-dependent intracellular signaling pathways. C-peptide polypeptides preferably have an association rate constant for binding to endothelial cells, renal tubular cells, and fibroblasts of ~$3 \times 10^9$ $M^{-1}$. C-peptide polypeptides are preferably C-peptides, C-peptide analogs, C-peptide fragments, or C-peptide fragment analogs.

As used herein, the term "pro-C-peptide polypeptide" means a C-peptide polypeptide coupled to one or more peptides that are cleavable to provide the C-peptide polypeptide.

As used herein, the term "A-chain polypeptide" means a polypeptide that is substantially biologically equivalent to the A-chain of an insulin molecule. For example, A-chain polypeptides may be A-chain analogs, which may be provided as described above with respect to insulin analogs, A-chain fragments, or A-chain analog fragments.

As used herein, the term "B-chain polypeptide" means a polypeptide that is substantially biologically equivalent to the B-chain of an insulin molecule. For example, B-chain polypeptides may be B-chain analogs, which may be provided as described above with respect to insulin analogs, B-chain fragments, or B-chain analog fragments.

As used herein, the term "polypeptide" means a peptide having two or more amino acid residues.

As used herein, the term "amphiphilically balanced" means capable of substantially dissolving in water and capable of penetrating biological membranes.

As used herein, the term "polyalkylene glycol" refers to straight or branched polyalkylene glycol polymers such as polyethylene glycol, polypropylene glycol, and polybutylene glycol, and includes the monoalkylether of the polyalkylene glycol. The term "polyalkylene glycol subunit" refers to a single polyalkylene glycol unit. For example, a polyethylene glycol subunit would be —O—$CH_2$—$CH_2O$—.

As used herein, the term "lipophilic" means the ability to dissolve in lipids and/or the ability to penetrate, interact with and/or traverse biological membranes, and the term, "lipophilic moiety" or "lipophile" means a moiety which is lipophilic and/or which, when attached to another chemical entity, increases the lipophilicity of such chemical entity. Examples of lipophilic moieties include, but are not limited to, alkyls, fatty acids, esters of fatty acids, cholesteryl, adamantyl and the like.

As used herein, the term "lower alkyl" refers to substituted or unsubstituted alkyl moieties having from one to five carbon atoms.

As used herein, the term "higher alkyl" refers to substituted or unsubstituted alkyl moieties having six or more carbon atoms.

According to embodiments of the present invention, methods of synthesizing an insulin polypeptide-oligomer conjugate include contacting a proinsulin polypeptide comprising an insulin polypeptide coupled to one or more peptides by peptide bond(s) capable of being cleaved to yield the insulin polypeptide with an oligomer under conditions sufficient to couple the oligomer to the insulin polypeptide portion of the proinsulin polypeptide and provide a proinsulin polypeptide-oligomer conjugate, and cleaving the one or more peptides from the proinsulin polypeptide-oligomer conjugate to provide the insulin polypeptide-oligomer conjugate. For example, insulin-oligomer conjugates may be synthesized as described in the Examples provided below. An embodiment of a synthesis route is provided in FIG. 1.

The proinsulin polypeptide may be various proinsulin polypeptides comprising an insulin polypeptide coupled to one or more peptides by peptide bond(s) capable of being cleaved to yield the insulin polypeptide as will be understood by those skilled in the art including, but not limited to, proinsulin, proinsulin analogs, proinsulin fragments, proinsulin fragment analogs, miniproinsulin, or fusion proteins. In some embodiments, the proinsulin polypeptide is a proinsulin analog having a leader peptide. The proinsulin analog having a leader peptide is produced by Itoham Foods, Inc. of Ibaraki Pref, Japan. The leader peptide and the C-peptide of the proinsulin analog are each devoid of lysine residues. In other embodiments, the proinsulin polypeptide is a proinsulin poplypeptide produced by Biobras of Belo Horizonte, Brazil. The proinsulin polypeptide has a leader peptide coupled to the N-terminus of the B-chain of the proinsulin. The leader peptide is devoid of lysine residues.

The insulin polypeptide preferably has an A-chain polypeptide and a B-chain polypeptide. The A-chain polypeptide is preferably devoid of lysine residues. The B-chain polypeptide preferably comprises a single lysine residue. The A-chain polypeptide and the B-chain polypeptide are preferably cross-linked, and are more preferably cross-linked using one or more disulfide bonds. Still more preferably, the A-chain polypeptide and the B-chain polypeptide each comprise cysteine residues, one or more of which are coupled using one or more disulfide bonds to cross-link the A-chain polypeptide with the B-chain polypeptide. Preferably, the insulin polypeptide is insulin, an insulin analog, an insulin fragment, or an insulin analog fragment.

In some embodiments, the one or more peptides coupled to the insulin polypeptide comprise a connecting peptide coupled at a first end to the C-terminus of the B-chain polypeptide and at a second end to the N-terminus of the A-chain polypeptide. In general, the amino acid sequence of the connecting peptide is not critical and the connecting peptide may be various connecting peptides as will be understood by those skilled in the art including, but not limited to, C-peptide polypeptides, C-peptides, and the connecting peptides in miniproinsulins. In some embodiments, the connecting peptide is devoid of lysine residues. These embodiments may utilize less oligomeric reagents by reducing the number of possible conjugation sites on the proinsulin polypeptide molecule.

In other embodiments, the one or more peptides coupled to the insulin polypeptide comprise a leader peptide that is coupled to the N-terminus of the B-chain polypeptide. In general, the amino acid sequence of the leader peptide is not critical. In some embodiments, the leader peptide is devoid of lysine residues. These embodiments may reduce the amount of oligomeric reagent used by limiting the number of conjugation sites on the proinsulin polypeptide molecule.

In still other embodiments, the one or more peptides coupled to the insulin polypeptide comprise both a connecting peptide as described above and a leader peptide as described above. The one or more peptides may consist essentially of a connecting peptide and a leader peptide, or may consist of a connecting peptide and a leader peptide.

The peptide bonds are bonds that may be cleaved in various ways as will be understood by those skilled in the art. Preferably, the peptide bonds are bonds that may be enzymatically cleaved by enzymes including, but not limited to, trypsin, carboxy peptidase B, thrombin, pepsin, and chymotripsin. Peptide bonds that may be enzymatically cleaved will be understood by those skilled in the art and include, but are not limited to, Arg-Arg, Thr-Arg, Ala-Arg, Thr-Arg-Arg, Thr-Lys, Arg-Gly, and Arg-Phe.

The oligomer may be various oligomers as will be understood by those skilled in the art. In general, the oligomer may be any oligomer capable of being coupled to a polypeptide as will be understood by those skilled in the art. For example, the oligomer may be a poly-dispersed oligomer as described in U.S. Pat. No. 4,179,337 to Davis et al.; U.S. Pat. No. 5,567,422 to Greenwald; U.S. Pat. No. 5,359,030 to Ekwuribe; U.S. Pat. No. 5,438,040 to Ekwuribe, U.S. Pat. No. 5,681,811 to Ekwuribe, and U.S. Pat. No. 6,309,633 to Ekwuribe et al., the disclosures of each of which are incorporated herein by reference in their entireties. As another example, the oligomer may be a non-polydispersed oligomer as described in U.S. patent application Ser. No. 09/873,731 filed Jun. 4, 2001 by Ekwuribe et al. entitled "Methods of Synthesizing Substantially Monodispersed Mixtures of Polymers Having Polyethylene Glycol Mixtures"; U.S. patent application Ser. No. 09/873,797 filed Jun. 4, 2001 by Ekwuribe et al. entitled "Mixtures of Drug-Oligomer Conjugates Comprising Polyalkylene Glycol, Uses Thereof, and Methods of Making Same"; and U.S. patent application Ser. No. 09/873,899 filed Jun. 4, 2001 by Ekwuribe et al. entitled "Mixtures of Insulin Drug-Oligomer Conjugates Comprising Polyalkylene Glycol, Uses Thereof, and Methods of Making Same," the disclosures of each of which are incorporated herein in their entireties.

In some embodiments, the oligomer comprises a hydrophilic moiety as will be understood by those skilled in the art including, but not limited to, polyalkylene glycols such as polyethylene glycol or polypropylene glycol, polyoxyethylenated polyols, copolymers thereof and block copolymers thereof, provided that the hydrophilicity of the block copolymers is maintained. The hydrophilic moiety is preferably a polyalkylene glycol moiety. The polyalkylene glycol moiety has at least 1, 2, 3, 4, 5, 6 or 7 polyalkylene glycol subunits. The polyalkylene glycol moiety preferably has between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. The polyalkylene glycol moiety more preferably has between a lower limit of 2, 3, 4, 5, or 6 and an upper limit of 5, 6, 7, 8, 9, 10, 11, 12, 13, 14, 15, 16, 17, 18, 19, or 20 polyalkylene glycol subunits. Even more preferably, the polyalkylene glycol moiety has between a lower limit of 3, 4, 5, or 6 and an upper limit of 5, 6, 7, 8, 9, 10, 11, or 12 polyalkylene glycol subunits. The polyalkylene glycol moiety still more preferably has between a lower limit of 4, 5, or 6 and an upper limit of 6, 7, or 8 polyalkylene glycol subunits. The polyalkylene glycol moiety most preferably has 7 polyalkylene glycol subunits. The polyalkylene glycol moiety of the oligomer is preferably a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety preferably has a uniform (i.e., not random) structure. An exemplary polypropylene glycol moiety having a uniform structure is as follows:

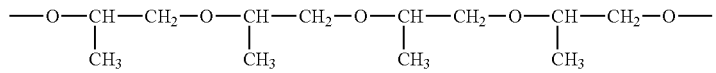

This uniform polypropylene glycol structure may be described as having only one methyl substituted carbon atom adjacent each oxygen atom in the polypropylene glycol chain. Such uniform polypropylene glycol moieties may exhibit both lipophilic and hydrophilic characteristics.

The oligomer may comprise one or more other moieties as will be understood by those skilled in the art including, but not limited to, additional hydrophilic moieties, lipophilic moieties, spacer moieties, linker moieties, and terminating moieties. The various moieties in the oligomer are covalently coupled to one another by either hydrolyzable or non-hydrolyzable bonds.

The oligomer may further comprise one or more additional hydrophilic moieties (i.e., moieties in addition to the polyalkylene glycol moiety) including, but not limited to, sugars, polyalkylene glycols, and polyamine/PEG copolymers. Adjacent polyalkylene glycol moieties will be considered to be the same moiety if they are coupled by ether bonds. For example, the moiety

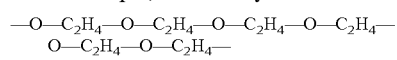

is a single polyethylene glycol moiety having six polyethylene glycol subunits. If this moiety were the only hydrophilic moiety in the oligomer, the oligomer would not contain an additional hydrophilic moiety. Adjacent polyethylene glycol moieties will be considered to be different moieties if they are coupled by a bond other than an ether bond. For example, the moiety

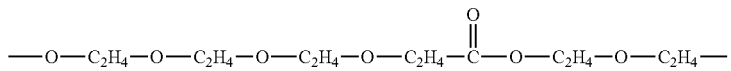

is a polyethylene glycol moiety having four polyethylene glycol subunits and an additional hydrophilic moiety having two polyethylene glycol subunits. Preferably, oligomers according to embodiments of the present invention comprise a polyalkylene glycol moiety and no additional hydrophilic moieties.

The oligomer preferably further comprises one or more lipophilic moieties as will be understood by those skilled in the art. The lipophilic moiety has at least 1, 2, 3, 4, 5, or 6 carbon atoms. The lipophilic moiety preferably has between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety more preferably has between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or carbon atoms. The lipophilic moiety even more preferably has between a lower limit of 3, 4, 5, 6, 7, 8, or 9 and an upper limit of 4, 5, 6, 7, 8, 9, 10, 11, 12, 13, or 14 carbon atoms. The lipophilic moiety still more preferably has between a lower limit of 3, 4, 5, 6, or 7 and an upper limit of 6, 7, 8, 9, or 10 carbon atoms. The lipophilic moiety most preferably has 6 carbon atoms. The lipophilic moiety is preferably selected from the group consisting of saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaentoate, and docosahexaenoate; and saturated fatty acid moieties such as acetate, caproate, caprylate, caprate, laurate, arachidate, behenate, lignocerate, and cerotate.

The oligomer may further comprise one or more spacer moieties as will be understood by those skilled in the art. Spacer moieties may, for example, be used to separate a hydrophilic moiety from a lipophilic moiety, to separate a lipophilic moiety or hydrophilic moiety from the proinsulin polypeptide, to separate a first hydrophilic or lipophilic moiety from a second hydrophilic or lipophilic moiety, or to separate a hydrophilic moiety or lipophilic moiety from a linker moiety. Spacer moieties are preferably selected from the group consisting of sugar, cholesterol and glycerine moieties. Sugar moieties may be various sugar moieties as will be understood by those skilled in the art including, but not limited to, monosaccharide moieties and disaccharide moieties. Preferred monosaccharide moieties have between 4 and 6 carbon atoms.

The oligomer may further comprise one or more linker moieties that are used to couple the oligomer with the proinsulin polypeptide as will be understood by those skilled in the art. Linker moieties are preferably selected from the group consisting of alkyl and fatty acid moieties. The alkyl linker moiety may be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety may be various alkoxy moieties including, but not limited to, methoxy, ethoxy, propoxy, butoxy, pentyloxy, hexyloxy, heptyloxy, octyloxy, nonyloxy, decyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The alkyl linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms, and preferably has between 1, 2, 3, 4, or 5 and 8, 9, 10, 11, or 12 carbon atoms. The fatty acid linker moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate. The fatty acid linker moiety may have between a lower limit of 1, 2, 3, 4 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms and preferably has between 1, 2, 3, 4, or 5 and 8, 10, 12, 14 or 16 carbon atoms.

The oligomer may further comprise one or more terminating moieties at the one or more ends of the oligomer, which are not coupled to the insulin polypeptide. The terminating moiety is preferably an alkyl or alkoxy moiety. The alkyl or alkoxy moiety preferably has between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety more preferably has between a lower limit of 1, 2, 3, 4, 5, 6, or 7 and an upper limit of 5, 6, 7, 8, 9, 10, 11, 12, 13, or 14 carbon atoms. The alkyl or alkoxy moiety even more preferably has between a lower limit of 1, 2, 3, 4, or 5 and an upper limit of 5, 6, 7, 8, 9, or 10 carbon atoms. The alkyl or alkoxy moiety still more preferably has between a lower limit of 1, 2, 3, or 4 and an upper limit of 5, 6, or 7 carbon atoms. The alkyl moiety may be a linear or branched, saturated or unsaturated alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety is more preferably a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. Most preferably, the terminating moiety is methyl or methoxy. While the terminating moiety is preferably an alkyl or alkoxy moiety, it is to be understood that the terminating moiety may be various moieties as will be understood by those skilled in the art including, but not limited to, sugars, cholesterol, alcohols, and fatty acids.

According to other embodiments of the present invention, the oligomer comprises the structure of Formula I:

  (I)

wherein:
A is an activatable moiety;
L is a linker moiety;
G, G' and G" are individually selected spacer moieties;
R is a lipophilic moiety and R' is a polyalkylene glycol moiety, or R' is the lipophilic moiety and R is the polyalkylene glycol moiety;
T is a terminating moiety; and
j, k, m and n are individually 0 or 1.

According to these embodiments of the present invention, the polyalkylene glycol moiety has at least 1, 2, 3, 4, 5, 6 or 7 polyalkylene glycol subunits. The polyalkylene glycol moiety preferably has between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. The polyalkylene glycol moiety more preferably has between a lower limit of 2, 3, 4, 5, or 6 and an upper limit of 5, 6, 7, 8, 9, 10, 11, 12, 13, 14, 15, 16, 17, 18, 19, or 20 polyalkylene glycol subunits. Even more preferably, the polyalkylene glycol moiety has between a lower limit of 3, 4, 5, or 6 and an upper limit of 5, 6, 7, 8, 9, 10, 11, or 12 polyalkylene glycol subunits. The polyalkylene glycol moiety still more preferably has between a lower limit of 4, 5, or 6 and an upper limit of 6, 7, or 8 polyalkylene glycol subunits. The polyalkylene glycol moiety most preferably has 7 polyalkylene glycol subunits. The polyalkylene glycol moiety of the oligomer is preferably a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety preferably has a uniform (i.e., not random) structure. An exemplary polypropylene glycol moiety having a uniform structure is as follows:

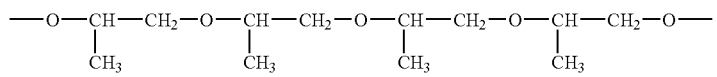

This uniform polypropylene glycol structure may be described as having only one methyl substituted carbon atom adjacent each oxygen atom in the polypropylene glycol chain. Such uniform polypropylene glycol moieties may exhibit both lipophilic and hydrophilic characteristics.

According to these embodiments of the present invention, the lipophilic moiety is a lipophilic moiety as will be understood by those skilled in the art. The lipophilic moiety has at least 1, 2, 3, 4, 5, or 6 carbon atoms. The lipophilic moiety preferably has between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety more preferably has between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or carbon atoms. The lipophilic moiety even more preferably has between a lower limit of 3, 4, 5, 6, 7, 8, or 9 and an upper limit of 4, 5, 6, 7, 8, 9, 10, 11, 12, 13, or 14 carbon atoms. The lipophilic moiety still more preferably has between a lower limit of 3, 4, 5, 6, or 7 and an upper limit of 6, 7, 8, 9, or 10 carbon atoms. The lipophilic moiety most preferably has 6 carbon atoms. The lipophilic moiety is preferably selected from the group consisting of saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaentoate, and docosahexaenoate; and saturated fatty acid moieties such as acetate, caproate, caprylate, caprate, laurate, arachidate, behenate, lignocerate, and cerotate.

According to these embodiments of the present invention, the spacer moieties, G, G' and G", are spacer moieties as will be understood by those skilled in the art. Spacer moieties are preferably selected from the group consisting of sugar moieties, cholesterol and glycerine moieties. Sugar moieties may be various sugar moieties as will be understood by those skilled in the art including, but not limited to, monosaccharide moieties and disaccharide moieties. Preferred monosaccharide moieties have between 4 and 6 carbon atoms. Preferably, oligomers of these embodiments do not include spacer moieties (i.e., k, m and n are preferably 0).

According to these embodiments of the present invention, the linker moiety, L, may be used to couple the oligomer with the drug as will be understood by those skilled in the art. Linker moieties are preferably selected from the group consisting of alkyl and fatty acid moieties. The alkyl linker moiety may be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The alkyl linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms, and preferably has between 1, 2, 3, 4, or 5 and 8, 9, 10, 11, or 12 carbon atoms. The fatty acid linker moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate. The fatty acid linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms and preferably has between 1, 2, 3, 4, or 5 and 8, 10, 12, 14 or 16 carbon atoms.

According to these embodiments of the present invention, the terminating moiety, T, is preferably an alkyl or alkoxy moiety. The alkyl or alkoxy moiety preferably has between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety more preferably has between a lower limit of 1, 2, 3, 4, 5, 6, or 7 and an upper limit of 5, 6, 7, 8, 9, 10, 11, 12, 13, or 14 carbon atoms. The alkyl or alkoxy moiety even more preferably has between a lower limit of 1, 2, 3, 4, or 5 and an upper limit of 5, 6, 7, 8, 9, or 10 carbon atoms. The alkyl or alkoxy moiety still more preferably has between a lower limit of 1, 2, 3, or 4 and an upper limit of 5, 6, or 7 carbon atoms. The alkyl moiety may be various linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. Exemplary alkoxy moieties may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety is more preferably a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. Most preferably, the terminating moiety is methyl or methoxy. While the terminating moiety is preferably an alkyl or alkoxy moiety, it is to be understood that the terminating moiety maybe various moieties as will be understood by those skilled in the art including, but not limited to, sugar moieties, cholesterol, alcohols, and fatty acid moieties.

According to these embodiments of the present invention, the activatable moiety, A, is a moiety that allows for the coupling of the oligomer to an activating agent to form an activated oligomer capable of coupling with the proinsulin polypeptide. The activatable moiety may be various activatable moieties as will be understood by those skilled in the art including, but not limited to, —C(O)—OH, C(S)—OH, —C(S)—SH, —OH, —SH, and NH$_2$.

In still other embodiments, the oligomer comprises the structure of Formula II:

$$A\text{-}X(CH_2)_mY(C_2H_4O)_nR \qquad (II)$$

wherein:

A is —C(O)—OH, C(S)—OH, —C(S)—SH, —OH, —SH, or NH$_2$;

X is an oxygen atom or a covalent bond, with the proviso X is not an oxygen atom when A is —OH;

Y is an ester, an ether, a carbamate, a carbonate, or an amide bonding moiety, and is preferably an ether bonding moiety;

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably has between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, is more preferably between a lower limit of 2, 3, 4, 5, or 6 and an upper limit of 5, 6, 7, 8, 9, 10, 11, 12, 13, 14, 15, 16, 17, 18, 19, or 20, is even more preferably between a lower limit of 3, 4, 5, or 6 and an upper limit of 5, 6, 7, 8, 9, 10, 11, or 12 polyalkylene glycol subunits, is still more preferably between a lower limit of 4, 5, or 6 and an upper limit of 6, 7, or 8 polyalkylene glycol subunits, and is most preferably 7; and R is an alkyl moiety, a sugar moiety, cholesterol, adamantane, an alcohol moiety, or a fatty acid moiety. The alkyl moiety may be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety is more preferably a lower alkyl moiety such as methyl, ethyl, propyl, isopropyl, butyl, sec-butyl, tert-butyl, pentyl, or tert-pentyl. The alkyl moiety is still more preferably a $C_1$ to $C_3$ alkyl. The alkyl moiety is most preferably methyl. The fatty acid moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate.

In still other embodiments, the oligomer comprises the structure of Formula III:

$$A\text{-}(CH_2)_m(OC_2H_4)_nOR \qquad (III)$$

wherein:

A is —C(O)—OH, C(S)—OH, —C(S)—SH, —OH, —SH, or $NH_2$;

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably has between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, is more preferably between a lower limit of 2, 3, 4, 5, or 6 and an upper limit of 5, 6, 7, 8, 9, 10, 11, 12, 13, 14, 15, 16, 17, 18, 19, or 20, is even more preferably between a lower limit of 3, 4, 5, or 6 and an upper limit of 5, 6, 7, 8, 9, 10, 11, or 12 polyalkylene glycol subunits, is still more preferably between a lower limit of 4, 5, or 6 and an upper limit of 6, 7, or 8 polyalkylene glycol subunits, and is most preferably 7; and R is an alkyl moiety, a sugar moiety, cholesterol, adamantane, an alcohol moiety, or a fatty acid moiety. The alkyl moiety may be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety is more preferably a lower alkyl moiety such as methyl, ethyl, propyl, isopropyl, butyl, sec-butyl, tert-butyl, pentyl, or tert-pentyl. The alkyl moiety is still more preferably a $C_1$ to $C_3$ alkyl. The alkyl moiety is most preferably methyl. The fatty acid moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate.

In yet other embodiments, the oligomer comprises the structure of Formula IV:

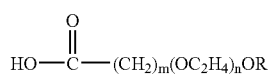

(IV)

wherein:

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 4, 5, 6, 7, 8, 9, 10, 11, 12, 13, 14, 15, 16, 11, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably has between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, is more preferably between a lower limit of 2, 3, 4, 5, or 6 and an upper limit of 5, 6, 7, 8, 9, 10, 11, 12, 13, 14, 15, 16, 17, 18, 19, or 20, is even more preferably between a lower limit of 3, 4, 5, or 6 and an upper limit of 5, 6, 7, 8, 9, 10, 11, or 12 polyalkylene glycol subunits, is still more preferably between a lower limit of 4, 5, or 6 and an upper limit of 6, 7, or 8 polyalkylene glycol subunits, and is most preferably 7; and R is an alkyl moiety, a sugar moiety, cholesterol, adamantine, an alcohol moiety, or a fatty acid moiety. The alkyl moiety may be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety is more preferably a lower alkyl moiety such as methyl, ethyl, propyl, isopropyl, butyl, sec-butyl, tert-butyl, pentyl, or tert-pentyl. The alkyl moiety is still more preferably a $C_1$ to $C_3$ alkyl. The alkyl moiety is most preferably methyl. The fatty acid moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate.

In still other embodiments, the oligomer comprises the structure of Formula V:

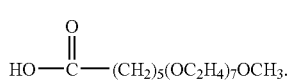

(V)

In the various embodiments described above, the oligomer is covalently coupled to the insulin polypeptide. In some embodiments, the oligomer is coupled to the insulin polypeptide utilizing a hydrolyzable bond (e.g., an ester or carbonate bond). A hydrolyzable coupling may provide an insulin polypeptide-oligomer conjugate that acts as a prodrug. In certain instances, for example where the insulin polypeptide-oligomer conjugate is biologically inactive (i.e., the conjugate lacks the ability to affect the body through the insulin polypeptide's primary mechanism of action), a hydrolyzable coupling may provide for a time-release or controlled-release effect, providing the biologically active insulin polypeptide over a given time period as one or more oligomers are cleaved from their respective biologically inactive insulin polypeptide-oligomer conjugates to provide the biologically active insulin polypeptide. In other embodiments, the oligomer is coupled to the insulin polypeptide utilizing a non-hydrolyzable bond (e.g., a carbamate, amide, or ether bond). Use of a non-hydrolyzable bond may be preferable when it is desirable to allow the biologically inactive insulin polypeptide-oligomer conjugate to circulate in the bloodstream for an extended period of time, preferably at least 2 hours. When the oligomer is coupled to the insulin polypeptide utilizing a bonding moiety that comprises a carbonyl moiety, such as an ester, a carbamate, a carbonate, or an amide bonding moiety, the resulting insulin polypeptide-oligomer conjugate is an insulin polypeptide-acyl oligomer conjugate.

Oligomers employed in the various embodiments described above are commercially available or may be synthesized by various methods as will be understood by those skilled in the art. For example, polydispersed oligomers may be synthesized by the methods provided in one or more of the following references: U.S. Pat. No. 4,179,337 to Davis et al.; U.S. Pat. No. 5,567,422 to Greenwald; U.S. Pat. No. 5,359,030 to Ekwuribe; U.S. Pat. No. 5,438,040 to Ekwuribe, U.S. Pat. No. 5,681,811 to Ekwuribe, U.S. Pat. No. 6,309,633 to Ekwuribe et al. Non-polydispersed (e.g., substantially monodispersed and monodispersed) oligomers may be synthesized by methods provided in one or more of the following references: U.S. patent application Ser. No. 09/873,731 filed Jun. 4, 2001 by Ekwuribe et al. entitled "Methods of Synthesizing Substantially Monodispersed Mixtures of Polymers Having Polyethylene Glycol Mixtures"; U.S. patent application Ser. No. 09/873,797 filed Jun. 4, 2001 by Ekwuribe et al. entitled "Mixtures of Drug-Oligomer Conjugates Comprising Polyalkylene Glycol, Uses Thereof, and Methods of Making Same"; and U.S. patent application Ser. No. 09/873,899 filed Jun. 4, 2001 by Ekwuribe et al. entitled "Mixtures of Insulin Drug-Oligomer Conjugates Comprising Polyalkylene Glycol, Uses Thereof, and Methods of Making Same". Oligomers according to embodiments of the present invention are preferably substantially monodispersed and are more preferably monodispersed. Exemplary methods for synthesizing preferred monodispersed oligomers are provided in Examples 1 through 10 below.

The contacting of the proinsulin polypeptide with the oligomer under conditions sufficient to provide a proinsulin polypeptide-oligomer conjugate may be performed utilizing various conditions as will be understood by those skilled in the art. Preferably, the contacting of the proinsulin polypeptide with the oligomer under conditions sufficient to provide a proinsulin polypeptide-oligomer conjugate comprises contacting the oligomer with an activating agent under conditions sufficient to provide an activated oligomer; and contacting the activated oligomer with the proinsulin polypeptide under conditions sufficient to provide the proinsulin polypeptide conjugate. The activated oligomer may be formed ex situ or in situ.

The activating agent may be various activating agents capable of activating one or more of the oligomers described above so that the oligomer is capable of reacting with nucleophilic hydroxyl functions and/or amino functions in the proinsulin polypeptide as will be understood by those skilled in the art including, but not limited to, N-hydroxysuccinimide, p-nitrophenyl chloroformate, 1,3-dicyclohexylcarbodiimide, and hydroxybenzotriazide.

One skilled in the art will understand the conditions sufficient to couple the activating agent to the oligomer to provide an activated oligomer. For example, one skilled in the art can refer to R. C. Larock, COMPREHENSIVE ORGANIC TRANSFORMATIONS. A GUIDE TO FUNCTIONAL GROUP PREPARATIONS (2d Edition, New York, Wiley-VCH, 1999), the disclosure of which is incorporated by reference herein in its entirety.

The conditions sufficient to couple the activated oligomer to the proinsulin polypeptide will be understood to one of skill in the art. For example, the proinsulin polypeptide may be dissolved in a dipolar aprotic solvent, such as dimethylsulfoxide, to provide a proinsulin polypeptide solution. A buffering agent, such as triethylamine, may be added to the proinsulin polypeptide solution. The activated oligomer dissolved in an anydrous solvent such as acetonitrile may then be added to the proinsulin polypeptide solution. One skilled in the art may also refer to R. C. Larock, COMPREHENSIVE ORGANIC TRANSFORMATIONS. A GUIDE TO FUNCTIONAL GROUP PREPARATIONS (2d Edition, New York, Wiley-VCH, 1999). The molar ratio of activated oligomer to proinsulin polypeptide is preferably greater than about 1:1, is more preferably greater than about 2:1, is even more preferably greater than about 3:1, is still more preferably greater than about 4:1, and is still even more preferably greater than about 5:1.

In the various embodiments described above, more than one oligomer (i.e., a plurality of oligomers) may be coupled to the insulin polypeptide portion of the proinsulin polypeptide. The oligomers in the plurality are preferably the same. However, it is to be understood that the oligomers in the plurality may be different from one another, or, alternatively, some of the oligomers in the plurality may be the same and some may be different. When a plurality of oligomers are coupled to the insulin polypeptide portion of the proinsulin polypeptide, it may be preferable to couple one or more of the oligomers to the insulin polypeptide portion of the proinsulin polypeptide with hydrolyzable bonds and couple one or more of the oligomers to the insulin polypeptide portion of the proinsulin polypeptide with non-hydrolyzable bonds. Alternatively, all of the bonds coupling the plurality of oligomers to the insulin polypeptide portion of the proinsulin polypeptide may be hydrolyzable, but have varying degrees of hydrolyzability such that, for example, one or more of the oligomers is rapidly removed from the insulin polypeptide or insulin polypeptide portion of the proinsulin polypeptide by hydrolysis in the body and one or more of the oligomers is slowly removed from the insulin polypeptide or insulin polypeptide portion by hydrolysis in the body.

In the various embodiments described above, the oligomer may be coupled to the insulin polypeptide portion of the proinsulin polypeptide at various nucleophilic residues of the insulin polypeptide portion including, but not limited to, nucleophilic hydroxyl functions and/or amino functions. A nucleophilic hydroxyl function may be found, for example, at serine and/or tyrosine residues, and a nucleophilic amino function may be found, for example, at histidine and/or lysine residues, and/or at the one or more N-termini of the polypeptide. When an oligomer is coupled to the one or more N-termini of the proinsulin polypeptide, the coupling preferably forms a secondary amine. When the proinsulin polypeptide has a leader peptide coupled to the N-terminus of the B-chain polypeptide, the N-termini of the insulin molecule may be protected from conjugation (e.g., acylation). When the proinsulin polypeptide is human proinsulin having a leader peptide coupled to the N-terminus of the B-chain, for example, the oligomer may be coupled to the three amino functionalities of the proinsulin: the N-terminus of the leader peptide, the amino functionality of the Lys residue in the C-peptide, and the amino functionality of $Lys^{B29}$. Upon cleavage of the leader peptide and the C-peptide, one finds that the oligomer has been site specifically coupled to the $Lys^{B29}$ of the insulin to provide a single insulin conjugate, insulin mono-conjugated with an oligomer at $Lys^{B29}$.

The cleaving of the one or more peptides from the proinsulin polypeptide-oligomer conjugate to provide the insulin polypeptide-oligomer conjugate may be performed by various processes as will be understood by those skilled in the art. Preferably, the cleaving of the one or more peptides from the proinsulin polypeptide-oligomer conjugate comprises contacting the proinsulin polypeptide-oligomer conjugate with one or more enzymes that are capable of cleaving the bond(s) between the one or more peptides and the insulin polypeptide under conditions sufficient to cleave the one or more peptides from the proinsulin polypeptide-oligomer conjugate. As described in various references, for example, Kemmler et al. "Studies on the Conversion of Proinsulin to Insulin," *J. Biol. Chem.*, 246: 6786-6791 (1971), the disclosure of which is incorporated herein by reference in its entirety, one skilled in the art will understand how to select appropriate enzymes in view of the particular peptide bond(s) to be cleaved and how to provide conditions sufficient to cleave the one or more peptides from the proinsulin polypeptide-oligomer conjugate. The one or more enzymes preferably comprise various enzymes including, but not limited to, trypsin, chymotrypsin, carboxy peptidase B, and mixtures thereof. More preferably, the one or more enzymes are selected from the group consisting of trypsin, carboxy peptidase B, and mixtures thereof.

In some embodiments such as those described above having a connecting peptide, the connecting peptide has a terminal amino acid residue at the first end. In some of these embodiments, the cleaving of the connecting peptide from the proinsulin polypeptide-oligomer conjugate comprises contacting the proinsulin polypeptide-oligomer conjugate with a first enzyme under conditions sufficient to provide a terminal amino acid residue-insulin polypeptide-oligomer conjugate, and contacting the terminal amino acid residue-insulin polypeptide-oligomer conjugate with a second enzyme under conditions sufficient to provide the insulin polypeptide-oligomer conjugate. The contacting of the proinsulin polypeptide-oligomer conjugate with a first enzyme and the contacting of the terminal amino acid residue-insulin polypeptide-oligomer conjugate with a second enzyme may occur substantially concurrently, for example when the first enzyme and the second enzyme are provided as a mixture or cocktail. Preferably, the first enzyme is trypsin and the second enzyme is carboxy peptidase B. The terminal amino acid residue may be various residues, such as an arginine residue. For example, the terminal amino acid residue is an arginine residue when the insulin polypeptide is insulin and the connecting peptide is human C-peptide.

The cleaving of the one or more peptides from the proinsulin polypeptide-oligomer conjugate preferably provides an insulin polypeptide-oligomer conjugate product that consists of a single insulin polypeptide-oligomer conjugate (i.e., is substantially devoid of additional insulin polypeptide-oligomer conjugates). Preferably, the insulin polypeptide-oligomer conjugate product consists of a single insulin polypeptide-oligomer monoconjugate. For example, in embodiments described above in which the proinsulin polypeptide comprises an insulin polypeptide having an A-chain polypeptide devoid of lysine residues and a B-chain polypeptide comprising a single lysine residue, the insulin polypeptide-oligomer conjugate product preferably consists of a single insulin polypeptide-oligomer monoconjugate where the oligomer is coupled to the lysine residue of the B-chain polypeptide. As another example, when the proinsulin polypeptide is proinsulin with a leader peptide, the cleaving of the C-peptide and the leader peptide from the proinsulin-oligomer conjugate provides an insulin-oligomer monoconjugate, wherein the insulin is monoconjugated at $Lys^{B29}$.

The embodiments of the methods for synthesizing insulin polypeptide-oligomer conjugates described above preferably result in a yield of insulin polypeptide-oligomer conjugates that is greater than 75, 76, 77, 78, or 79 percent. More preferably, the yield is greater than 80, 81, 82, 83, 84, or 85 percent. Even more preferably, the yield is greater than 86, 87, 88, 89, or 90 percent. Still more preferably, the yield is greater than 91, 92, 93, 94, or 95 percent. When the proinsulin polypeptide-oligomer conjugate is provided by contacting an activated oligomer with the proinsulin polypeptide-oligomer conjugate, it may be preferable to use an excess of activated oligomers in achieving higher yields. For example, yields described above are preferably obtained by using a molar ratio of activated oligomer to proinsulin polypeptide of greater than about 2:1, more preferably greater than about 3:1, even more preferably greater than about 4:1, and still more preferably greater than about 5:1. Preferably, yields greater than 91, 92, 93, 94, or 95 percent are obtained using a molar ratio of activated oligomer to proinsulin polypeptide of greater than about 4:1, more preferably greater than about 5:1.

According to other embodiments of the present invention, methods of synthesizing a proinsulin polypeptide-oligomer conjugate include contacting a proinsulin polypeptide comprising an insulin polypeptide coupled to one or more peptides by peptide bond(s) capable of being cleaved to yield the insulin polypeptide with an oligomer under conditions sufficient to couple the oligomer to the insulin polypeptide portion of the proinsulin polypeptide and provide a proinsulin polypeptide-oligomer conjugate. For example, proinsulin-oligomer conjugates may be synthesized as described in the Examples provided below. An embodiment of a synthesis route is provided in FIG. 1.

The proinsulin polypeptide may be various proinsulin polypeptides comprising an insulin polypeptide coupled to one or more peptides by peptide bond(s) capable of being cleaved to yield the insulin polypeptide as will be understood by those skilled in the art including, but not limited to, proinsulin, proinsulin analogs, proinsulin fragments, proinsulin fragment analogs, miniproinsulin, or fusion proteins. In some embodiments, the proinsulin polypeptide is a proinsulin analog having a leader peptide. The proinsulin analog having a leader peptide is produced by Itoham Foods, Inc. of Ibaraki Pref, Japan. The leader peptide and the C-peptide of the proinsulin analog are each devoid of lysine residues. In other embodiments, the proinsulin polypeptide is a proinsulin poplypeptide produced by Biobras of Belo Horizonte, Brazil. The proinsulin polypeptide has a leader peptide coupled to the N-terminus of the B-chain of the proinsulin. The leader peptide is devoid of lysine residues.

The insulin polypeptide preferably has an A-chain polypeptide and a B-chain polypeptide. The A-chain polypeptide is preferably devoid of lysine residues. The B-chain polypeptide preferably comprises a single lysine residue. The A-chain polypeptide and the B-chain polypeptide are preferably cross-linked, and are more preferably cross-linked using one or more disulfide bonds. Still more preferably, the A-chain polypeptide and the B-chain polypeptide each comprise cysteine residues, one or more of which are coupled using one or more disulfide bonds to cross-link the A-chain polypeptide with the B-chain polypeptide. Preferably, the insulin polypeptide is insulin, an insulin analog, an insulin fragment, or an insulin analog fragment.

In some embodiments, the one or more peptides coupled to the insulin polypeptide comprise a connecting peptide coupled at a first end to the C-terminus of the B-chain polypeptide and at a second end to the N-terminus of the A-chain polypeptide. In general, the amino acid sequence of the connecting peptide is not critical and the connecting peptide may be various connecting peptides as will be understood by those skilled in the art including, but not limited to, C-peptide polypeptides, C-peptides, and the connecting peptides in miniproinsulins. In some embodiments, the connecting peptide is devoid of lysine residues. These embodiments may utilize less oligomeric reagents by reducing the number of possible conjugation sites on the proinsulin polypeptide molecule.

In other embodiments, the one or more peptides coupled to the insulin polypeptide comprise a leader peptide that is coupled to the N-terminus of the B-chain polypeptide. In general, the amino acid sequence of the leader peptide is not critical. In some embodiments, the leader peptide is devoid of lysine residues. These embodiments may reduce the amount of oligomeric reagent used by limiting the number of conjugation sites on the proinsulin polypeptide molecule.

In still other embodiments, the one or more peptides coupled to the insulin polypeptide comprise both a connecting peptide as described above and a leader peptide as described above. The one or more peptides may consist essentially of a connecting peptide and a leader peptide, or may consist of a connecting peptide and a leader peptide.

The peptide bonds are bonds that may be cleaved in various ways as will be understood by those skilled in the art. Preferably, the peptide bonds are bonds that may be enzymatically cleaved by enzymes including, but not limited to, trypsin, carboxy peptidase B, thrombin, pepsin, and chymotripsin. Peptide bonds that may be enzymatically cleaved will be understood by those skilled in the art and include, but are not limited to, Arg-Arg, Thr-Arg, Ala-Arg, Thr-Arg-Arg, Thr-Lys, Arg-Gly, and Arg-Phe.

The oligomer may be various oligomers as will be understood by those skilled in the art. In general, the oligomer may be any oligomer capable of being coupled to a polypeptide as will be understood by those skilled in the art. For example, the oligomer may be a poly-dispersed oligomer as described in U.S. Pat. No. 4,179,337 to Davis et al.; U.S. Pat. No. 5,567,422 to Greenwald; U.S. Pat. No. 5,359,030 to Ekwuribe; U.S. Pat. No. 5,438,040 to Ekwuribe, U.S. Pat. No. 5,681,811 to Ekwuribe, and U.S. Pat. No. 6,309,633 to Ekwuribe et al. As another example, the oligomer may be a non-polydispersed oligomer as described in U.S. patent application Ser. No. 09/873,731 filed Jun. 4, 2001 by Ekwuribe et al. entitled "Methods of Synthesizing Substantially Monodispersed Mixtures of Polymers Having Polyethylene Glycol-Mixtures"; U.S. patent application Ser. No. 09/873,797 filed Jun. 4, 2001 by Ekwuribe et al. entitled "Mixtures of Drug-Oligomer Conjugates Comprising Polyalkylene Glycol, Uses Thereof, and Methods of Making Same"; and U.S. patent application Ser. No. 09/873,899 filed Jun. 4, 2001 by Ekwuribe et al. entitled "Mixtures of Insulin Drug-Oligomer Conjugates Comprising Polyalkylene Glycol, Uses Thereof, and Methods of Making Same."

The oligomer preferably comprises a hydrophilic moiety as will be understood by those skilled in the art including, but not limited to, polyalkylene glycols such as polyethylene glycol or polypropylene glycol, polyoxyethylenated polyols, copolymers thereof and block copolymers thereof, provided that the hydrophilicity of the block copolymers is maintained. The hydrophilic moiety is preferably a polyalkylene glycol moiety. The polyalkylene glycol moiety has at least 1, 2, 3, 4, 5, 6 or 7 polyalkylene glycol subunits. The polyalkylene glycol moiety preferably has between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. The polyalkylene glycol moiety more preferably has between a lower limit of 2, 3, 4, 5, or 6 and an upper limit of 5, 6, 7, 8, 9, 10, 11, 12, 13, 14, 15, 16, 17, 18, 19, or 20 polyalkylene glycol subunits. Even more preferably, the polyalkylene glycol moiety has between a lower limit of 3, 4, 5, or 6 and an upper limit of 5, 6, 7, 8, 9, 10, 11, or 12 polyalkylene glycol subunits. The polyalkylene glycol moiety still more preferably has between a lower limit of 4, 5, or 6 and an upper limit of 6, 7, or 8 polyalkylene glycol subunits. The polyalkylene glycol moiety most preferably has 7 polyalkylene glycol subunits. The polyalkylene glycol moiety of the oligomer is preferably a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety preferably has a uniform (i.e., not random) structure. An exemplary polypropylene glycol moiety having a uniform structure is as follows:

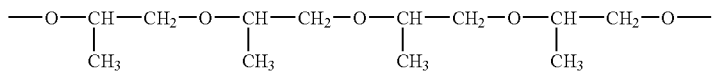

This uniform polypropylene glycol structure may be described as having only one methyl substituted carbon atom adjacent each oxygen atom in the polypropylene glycol chain. Such uniform polypropylene glycol moieties may exhibit both lipophilic and hydrophilic characteristics.

The oligomer may comprise one or more other moieties as will be understood by those skilled in the art including, but not limited to, additional hydrophilic moieties, lipophilic moieties, spacer moieties, linker moieties, and terminating moieties. The various moieties in the oligomer are covalently coupled to one another by either hydrolyzable or non-hydrolyzable bonds.

The oligomer may further comprise one or more additional hydrophilic moieties (i.e., moieties in addition to the polyalkylene glycol moiety) including, but not limited to, sugars, polyalkylene glycols, and polyamine/PEG copolymers. Adjacent polyalkylene glycol moieties will be considered to be the same moiety if they are coupled by ether bonds. For example, the moiety

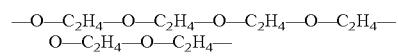

is a single polyethylene glycol moiety having six polyethylene glycol subunits. If this moiety were the only hydrophilic moiety in the oligomer, the oligomer would not contain an additional hydrophilic moiety. Adjacent polyethylene glycol moieties will be considered to be different moieties if they are coupled by a bond other than an ether bond. For example, the moiety

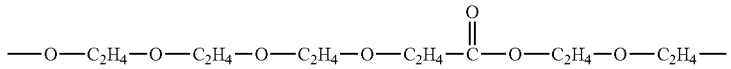

is a polyethylene glycol moiety having four polyethylene glycol subunits and an additional hydrophilic moiety having two polyethylene glycol subunits. Preferably, oligomers according to embodiments of the present invention comprise a polyalkylene glycol moiety and no additional hydrophilic moieties.

The oligomer preferably further comprises one or more lipophilic moieties as will be understood by those skilled in the art. The lipophilic moiety has at least 1, 2, 3, 4, 5, or 6 carbon atoms. The lipophilic moiety preferably has between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety more preferably has between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or carbon atoms. The lipophilic moiety even more preferably has between a lower limit of 3, 4, 5, 6, 7, 8, or 9 and an upper limit of 4, 5, 6, 7, 8, 9, 10, 11, 12, 13, or 14 carbon atoms. The lipophilic moiety still more preferably has between a lower limit of 3, 4, 5, 6, or 7 and an upper limit of 6, 7, 8, 9, or 10 carbon atoms. The lipophilic moiety most preferably has 6 carbon atoms. The lipophilic moiety is preferably selected from the group consisting of saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaentoate, and docosahexaenoate; and saturated fatty acid moieties such as acetate, caproate, caprylate, caprate, laurate, arachidate, behenate, lignocerate, and cerotate.

The oligomer may further comprise one or more spacer moieties as will be understood by those skilled in the art. Spacer moieties may, for example, be used to separate a hydrophilic moiety from a lipophilic moiety, to separate a lipophilic moiety or hydrophilic moiety from the proinsulin polypeptide, to separate a first hydrophilic or lipophilic moiety from a second hydrophilic or lipophilic moiety, or to separate a hydrophilic moiety or lipophilic moiety from a linker moiety. Spacer moieties are preferably selected from the group consisting of sugar, cholesterol and glycerine moieties. Sugar moieties may be various sugar moieties as will be understood by those skilled in the art including, but not limited to, monosaccharide moieties and disaccharide moieties. Preferred monosaccharide moieties have between 4 and 6 carbon atoms.

The oligomer may further comprise one or more linker moieties that are used to couple the oligomer with the proinsulin polypeptide as will be understood by those skilled in the art. Linker moieties are preferably selected from the group consisting of alkyl and fatty acid moieties. The alkyl linker moiety may be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The alkyl linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms, and preferably has between 1, 2, 3, 4, or 5 and 8, 9, 10, 11, or 12 carbon atoms. The fatty acid linker moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate. The fatty acid linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms and preferably has between 1, 2, 3, 4, or 5 and 8, 10, 12, 14 or 16 carbon atoms.

The oligomer may further comprise one or more terminating moieties at the one or more ends of the oligomer, which are not coupled to the insulin polypeptide. The terminating moiety is preferably an alkyl or alkoxy moiety. The alkyl or alkoxy moiety preferably has between a lower limit of 1, 2, 3, 4, 5, 6, 7, 8, 9, 10, 11, 11, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety more preferably has between a lower limit of 1, 2, 3, 4, 5, 6, or 7 and an upper limit of 5, 6, 7, 8, 9, 10, 11, 12, 13, or 14 carbon atoms. The alkyl or alkoxy moiety even more preferably has between a lower limit of 1, 2, 3, 4, or 5 and an upper limit of 5, 6, 7, 8, 9, or 10 carbon atoms. The alkyl or alkoxy moiety still more preferably has between a lower limit of 1, 2, 3, or 4 and an upper limit of 5, 6, or 7 carbon atoms. The alkyl moiety may be a linear or branched, saturated or unsaturated alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety is more preferably a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. Most preferably, the terminating moiety is methyl or methoxy. While the terminating moiety is preferably an alkyl or alkoxy moiety, it is to be understood that the terminating moiety may be various moieties as will be understood by those skilled in the art including, but not limited to, sugars, cholesterol, alcohols, and fatty acids.

According to other embodiments of the present invention, the oligomer comprises the structure of Formula VI:

wherein:
A is an activatable moiety;
L is a linker moiety;
G, G' and G" are individually selected spacer moieties;
R is a lipophilic moiety and R' is a polyalkylene glycol moiety, or R' is the lipophilic moiety and R is the polyalkylene glycol moiety;
T is a terminating moiety; and
j, k, m and n are individually 0 or 1.

According to these embodiments of the present invention, the polyalkylene glycol moiety has at least 1, 2, 3, 4, 5, 6 or 7 polyalkylene glycol subunits. The polyalkylene glycol moiety preferably has between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. The polyalkylene glycol moiety more preferably has between a lower limit of 2, 3, 4, 5, or 6 and an upper limit of 5, 6, 7, 8, 9, 10, 11, 12, 13, 14, 15, 16, 17, 18, 19, or 20 polyalkylene glycol subunits. Even more preferably, the polyalkylene glycol moiety has between a lower limit of 3, 4, 5, or 6 and an upper limit of 5, 6, 7, 8, 9, 10, 11, or 12 polyalkylene glycol subunits. The polyalkylene glycol moiety still more preferably has between a lower limit of 4, 5, or 6 and an upper limit of 6, 7, or 8 polyalkylene glycol subunits. The polyalkylene glycol moiety most preferably has 7 polyalkylene glycol subunits. The polyalkylene glycol moiety of the oligomer is preferably a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety preferably has a uniform (i.e., not random) structure. An exemplary polypropylene glycol moiety having a uniform structure is as follows:

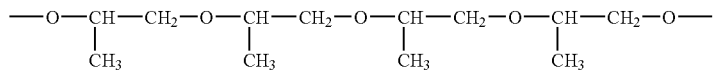

This uniform polypropylene glycol structure may be described as having only one methyl substituted carbon atom adjacent each oxygen atom in the polypropylene glycol chain. Such uniform polypropylene glycol moieties may exhibit both lipophilic and hydrophilic characteristics.

According to these embodiments of the present invention, the lipophilic moiety is a lipophilic moiety as will be understood by those skilled in the art. The lipophilic moiety has at least 1, 2, 3, 4, 5, or 6 carbon atoms. The lipophilic moiety preferably has between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety more preferably has between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or carbon atoms. The lipophilic moiety even more preferably has between a lower limit of 3, 4, 5, 6, 7, 8, or 9 and an upper limit of 4, 5, 6, 7, 8, 9, 10, 11, 12, 13, or 14 carbon atoms. The lipophilic moiety still more preferably has between a lower limit of 3, 4, 5, 6, or 7 and an upper limit of 6, 7, 8, 9, or 10 carbon atoms. The lipophilic moiety most preferably has 6 carbon atoms. The lipophilic moiety is preferably selected from the group consisting of saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaentoate, and docosahexaenoate; and saturated fatty acid moieties such as acetate, caproate, caprylate, caprate, laurate, arachidate, behenate, lignocerate, and cerotate.

According to these embodiments of the present invention, the spacer moieties, G, G' and G", are spacer moieties as will be understood by those skilled in the art. Spacer moieties are preferably selected from the group consisting of sugar moieties, cholesterol and glycerine moieties. Sugar moieties may be various sugar moieties as will be understood by those skilled in the art including, but not limited to, monosaccharide moieties and disaccharide moieties. Preferred monosaccharide moieties have between 4 and 6 carbon atoms. Preferably, oligomers of these embodiments do not include spacer moieties (i.e., k, m and n are preferably 0).

According to these embodiments of the present invention, the linker moiety, L, may be used to couple the oligomer with the drug as will be understood by those skilled in the art. Linker moieties are preferably selected from the group consisting of alkyl and fatty acid moieties. The alkyl linker moiety may be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The alkyl linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms, and preferably has between 1, 2, 3, 4, or 5 and 8, 9, 10, 11, or 12 carbon atoms. The fatty acid linker moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaenoate, docosahexaenoate, acetate, caproate, caprylate, caprate, laurate, arachidate, behenate, lignocerate, and cerotate. The fatty acid linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms and preferably has between 1, 2, 3, 4, or 5 and 8, 10, 12, 14 or 16 carbon atoms.

According to these embodiments of the present invention, the terminating moiety, T, is preferably an alkyl or alkoxy moiety. The alkyl or alkoxy moiety preferably has between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety more preferably has between a lower limit of 1, 2, 3, 4, 5, 6, or 7 and an upper limit of 5, 6, 7, 8, 9, 10, 11, 12, 13, or 14 carbon atoms. The alkyl or alkoxy moiety even more preferably has between a lower limit of 1, 2, 3, 4, or 5 and an upper limit of 5, 6, 7, 8, 9, or 10 carbon atoms. The alkyl or alkoxy moiety still more preferably has between a lower limit of 1, 2, 3, or 4 and an upper limit of 5, 6, or 7 carbon atoms. The alkyl moiety may be various linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. Exemplary alkoxy moieties may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety is more preferably a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. Most preferably, the terminating moiety is methyl or methoxy. While the terminating moiety is preferably an alkyl or alkoxy moiety, it is to be understood that the terminating moiety may be various moieties as will be understood by those skilled in the art including, but not limited to, sugar moieties, cholesterol, alcohols, and fatty acid moieties.

According to these embodiments of the present invention, the activatable moiety, A, is a moiety that allows for the coupling of the oligomer to an activating agent to form an activated oligomer capable of coupling with the proinsulin polypeptide. The activatable moiety may be various activatable moieties as will be understood by those skilled in the art including, but not limited to, —C(O)—OH, C(S)—OH, —C(S)—SH, —OH, —SH, and NH$_2$.

In still other embodiments, the oligomer comprises the structure of Formula VII:

A-X(CH$_2$)$_m$Y(C$_2$H$_4$O)$_n$R  (VII)

wherein:

A is —C(O)—OH, C(S)—OH, —C(S)—SH, —OH, —SH, or NH$_2$;

X is an oxygen atom or a covalent bond, with the proviso X is not an oxygen atom when A is —OH;

Y is an ester, an ether, a carbamate, a carbonate, or an amide bonding moiety, and is preferably an ether bonding moiety;

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably has between a lower limit of 3, 4, 5, 6, or 7 and an upper limit of 6, 7, 8, 9, or 10;

n is between a lower limit of 1, 2, 3, 4, 5, 6,7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 is more preferably between a lower limit of 2, 3, 4, 5, or 6 and an upper limit of 5, 6, 7, 8, 9, 10, 11, 12, 13, 14, 15, 16, 17, 18, 19, or 20, is even more preferably between a lower limit of 3, 4, 5, or 6 and an upper limit of 5, 6, 7, 8, 9, 10, 11, or 12 polyalkylene glycol subunits, is still more preferably between a lower limit of 4, 5, or 6 and an upper limit of 6, 7, or 8 polyalkylene glycol subunits, and is most preferably 7; and R is an alkyl moiety, a sugar moiety, cholesterol, adamantane, an alcohol moiety, or a fatty acid moiety. The alkyl moiety may be a linear or branched, saturated or unsaturated-alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety is more preferably a lower alkyl moiety such as methyl, ethyl, propyl, isopropyl, butyl, sec-butyl, tert-butyl, pentyl, or tert-pentyl. The alkyl moiety is still more preferably a $C_1$ to $C_3$ alkyl. The alkyl moiety is most preferably methyl. The fatty acid moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate.

In still other embodiments, the oligomer comprises the structure of Formula VIII:

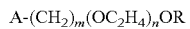 (VIII)

wherein:

A is —C(O)—OH, C(S)—OH, —C(S)—SH, —OH, —SH, or $NH_2$;

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably has between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, is more preferably between a lower limit of 2, 3, 4, 5, or 6 and an upper limit of 5, 6, 7, 8, 9, 10, 11, 12, 13, 14, 15, 16, 17, 18, 19, or 20, is even more preferably between a lower limit of 3, 4, 5, or 6 and an upper limit of 5, 6, 7, 8, 9, 10, 11, or 12 polyalkylene glycol subunits, is still more preferably between a lower limit of 4, 5, or 6 and an upper limit of 6, 7, or 8 polyalkylene glycol subunits, and is most preferably 7; and R is an alkyl moiety, a sugar moiety, cholesterol, adamantane, an alcohol moiety, or a fatty acid moiety. The alkyl moiety may be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety is more preferably a lower alkyl moiety such as methyl, ethyl, propyl, isopropyl, butyl, sec-butyl, tert-butyl, pentyl, or tert-pentyl. The alkyl moiety is still more preferably a $C_1$ to $C_3$ alkyl. The alkyl moiety is most preferably methyl. The fatty acid moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate.

In yet other embodiments, the oligomer comprises the structure of Formula IX:

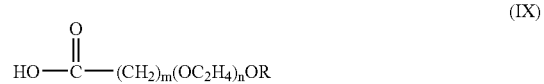 (IX)

wherein:

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably has between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, is more preferably between a lower limit of 2, 3, 4, 5, or 6 and an upper limit of 5, 6, 7, 8, 9, 10, 11, 12, 13, 14, 15, 16, 17, 18, 19, or 20, is even more preferably between a lower limit of 3, 4, 5, or 6 and an upper limit of 5, 6, 7, 8, 9, 10, 11, or 12 polyalkylene glycol subunits, is still more preferably between a lower limit of 4, 5, or 6 and an upper limit of 6, 7, or 8 polyalkylene glycol subunits, and is most preferably 7; and R is an alkyl moiety, a sugar moiety, cholesterol, adamantane, an alcohol moiety, or a fatty acid moiety. The alkyl moiety may be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety is more preferably a lower alkyl moiety such as methyl, ethyl, propyl, isopropyl, butyl, sec-butyl, tert-butyl, pentyl, or tert-pentyl. The alkyl moiety is still more preferably a $C_1$ to $C_3$ alkyl. The alkyl moiety is most preferably methyl. The fatty acid moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate.

In still other embodiments, the oligomer comprises the structure of Formula X:

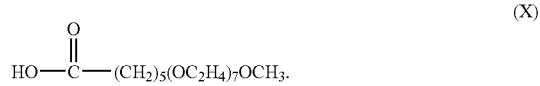

(X)

In the various embodiments of methods for synthesizing proinsulin polypeptide-oligomer conjugates described above, the oligomer is covalently coupled to the insulin polypeptide. In some embodiments, the oligomer is coupled to the insulin polypeptide utilizing a hydrolyzable bond (e.g., an ester or carbonate bond). A hydrolyzable coupling may provide an insulin polypeptide-oligomer conjugate that acts as a prodrug. In certain instances, for example where the insulin polypeptide-oligomer conjugate is biologically inactive (i.e., the conjugate lacks the ability to affect the body through the insulin polypeptide's primary mechanism of action), a hydrolyzable coupling may provide for a time-release or controlled-release effect, providing the biologically active insulin polypeptide over a given time period as one or more oligomers are cleaved from their respective biologically inactive insulin polypeptide-oligomer conjugates to provide the biologically active insulin polypeptide. In other embodiments, the oligomer is coupled to the insulin polypeptide utilizing a non-hydrolyzable bond (e.g., a carbamate, amide, or ether bond). Use of a non-hydrolyzable bond may be preferable when it is desirable to allow the biologically inactive insulin polypeptide-oligomer conjugate to circulate in the bloodstream for an extended period of time, preferably at least 2 hours. When the oligomer is coupled to the insulin polypeptide utilizing a bonding moiety that comprises a carbonyl moiety, such as an ester, a carbamate, a carbonate, or an amide bonding moiety, the resulting insulin polypeptide-oligomer conjugate is an insulin polypeptide-acyl oligomer conjugate.

Oligomers employed in the embodiments of methods for synthesizing proinsulin polypeptide oligomer conjugates described above are commercially available or may be synthesized by various methods as will be understood by those skilled in the art. For example, polydispersed oligomers may be synthesized by the methods provided in one or more of the following references: U.S. Pat. No. 4,179,337 to Davis et al.; U.S. Pat. No. 5,567,422 to Greenwald; U.S. Pat. No. 5,359,030 to Ekwuribe; U.S. Pat. No. 5,438,040 to Ekwuribe, U.S. Pat. No. 5,681,811 to Ekwuribe, U.S. Pat. No. 6,309,633 to Ekwuribe et al. Non-polydispersed (e.g., substantially monodispersed and monodispersed) oligomers may be synthesized by methods provided in one or more of the following references: U.S. patent application Ser. No. 09/873,731 filed Jun. 4, 2001 by Ekwuribe et al. entitled "Methods of Synthesizing Substantially Monodispersed Mixtures of Polymers Having Polyethylene Glycol Mixtures"; U.S. patent application Ser. No. 09/873,797 filed Jun. 4, 2001 by Ekwuribe et al. entitled "Mixtures of Drug-Oligomer Conjugates Comprising Polyalkylene Glycol, Uses Thereof, and Methods of Making Same"; and U.S. patent application Ser. No. 09/873,899. filed Jun. 4, 2001 by Ekwuribe et al. entitled "Mixtures of Insulin Drug-Oligomer Conjugates Comprising Polyalkylene Glycol, Uses Thereof, and Methods of Making Same". Oligomers according to embodiments of the present invention are preferably substantially monodispersed and are more preferably monodispersed. Exemplary methods for synthesizing preferred monodispersed oligomers are provided in Examples 1 through 10 below.

The contacting of the proinsulin polypeptide with the oligomer under conditions sufficient to provide a proinsulin polypeptide-oligomer conjugate may be performed utilizing various conditions as will be understood by those skilled in the art. Preferably, the contacting of the proinsulin polypeptide with the oligomer under conditions sufficient to provide a proinsulin polypeptide-oligomer conjugate comprises contacting the oligomer with an activating agent under conditions sufficient to provide an activated oligomer; and contacting the activated oligomer with the proinsulin polypeptide under conditions sufficient to provide the proinsulin polypeptide conjugate. The activated oligomer may be formed ex situ or in situ.

The activating agent may be various activating agents capable of activating one or more of the oligomers described above so that the oligomer is capable of reacting with nucleophilic hydroxyl functions and/or amino functions in the proinsulin polypeptide as will be understood by those skilled in the art including, but not limited to, N-hydroxysuccinimide, p-nitrophenyl chloroformate, 1,3-dicyclohexylcarbodiimide, and hydroxybenzotriazide.

One skilled in the art will understand the conditions sufficient to couple the activating agent to the oligomer to provide an activated oligomer. For example, one skilled in the art can refer to R. C. Larock, COMPREHENSIVE ORGANIC TRANSFORMATIONS. A GUIDE TO FUNCTIONAL GROUP PREPARATIONS (2d Edition, New York, Wiley-VCH, 1999).

The conditions sufficient to couple the activated oligomer to the proinsulin polypeptide will be understood to one of skill in the art. For example, the proinsulin polypeptide may be dissolved in a dipolar aprotic solvent, such as dimethylsulfoxide, to provide a proinsulin polypeptide solution. A buffering agent, such as triethylamine, may be added to the proinsulin polypeptide solution. The activated oligomer dissolved in an anydrous solvent such as acetonitrile may then be added to the proinsulin polypeptide solution. One skilled in the art may also refer to R. C. Larock, COMPREHENSIVE ORGANIC TRANSFORMATIONS. A GUIDE TO FUNCTIONAL GROUP PREPARATIONS (2d Edition, New York, Wiley-VCH, 1999). The molar ratio of activated oligomer to proinsulin polypeptide is preferably greater than about 1:1, is more preferably greater than about 2:1, is even more preferably greater than about 3:1, is still more preferably greater than about 4:1, and is still even more preferably greater than about 5:1.

In the various embodiments of methods for synthesizing proinsulin polypeptide-oligomer conjugates described above, more than one oligomer (i.e., a plurality of oligomers) may be coupled to the insulin polypeptide portion of the proinsulin polypeptide. The oligomers in the plurality are preferably the same. However, it is to be understood that the oligomers in the plurality may be different from one another, or, alternatively, some of the oligomers in the plurality may be the same and some may be different. When a plurality of oligomers are coupled to the insulin polypeptide portion of the proinsulin polypeptide, it may be preferable to couple one or more of the oligomers to the insulin polypeptide portion of the proinsulin polypeptide with hydrolyzable bonds and couple one or more of the oligomers to the insulin polypeptide portion of the proinsulin polypeptide with non-hydrolyzable bonds. Alternatively, all of the bonds coupling the plurality of oligomers to the insulin polypeptide portion of the proinsulin polypeptide may be hydrolyzable, but have varying degrees of hydrolyzability such that, for example, one or more of the oligomers is rapidly removed from the insulin polypeptide or insulin polypeptide portion of the proinsulin polypeptide by hydrolysis in the body and one or more of the oligomers is slowly removed from the insulin polypeptide or insulin polypeptide portion by hydrolysis in the body.

In the various embodiments of methods for synthesizing proinsulin polypeptide-oligomer conjugates described above, the oligomer may be coupled to the insulin polypeptide portion of the proinsulin polypeptide at various nucleophilic residues of the insulin polypeptide portion including, but not limited to, nucleophilic hydroxyl functions and/or amino functions. A nucleophilic hydroxyl function may be found, for example, at serine and/or tyrosine residues, and a nucleophilic amino function may be found, for example, at histidine and/or lysine residues, and/or at the one or more N-termini of the polypeptide. When an oligomer is coupled to the one or more N-termini of the proinsulin polypeptide, the coupling preferably forms a secondary amine. When the proinsulin polypeptide has a leader peptide coupled to the N-terminus of the B-chain polypeptide, the N-termini of the insulin molecule may be protected from conjugation (e.g., acylation). When the proinsulin polypeptide is human proinsulin having a leader peptide coupled to the N-terminus of the B-chain, for example, the oligomer may be coupled to the three amino functionalities of the proinsulin: the N-terminus of the leader peptide, the amino functionality of the Lys residue in the C-peptide, and the amino functionality of $Lys^{B29}$. Upon cleavage of the leader peptide and the C-peptide, one finds that the oligomer has been site specifically coupled to the $Lys^{B29}$ of the insulin to provide a single insulin conjugate, insulin mono-conjugated with an oligomer at $Lys^{B29}$.

According to still other embodiments of the present invention, a proinsulin polypeptide-oligomer conjugate includes a proinsulin polypeptide comprising an insulin polypeptide coupled to one or more peptides by peptide bond(s) that are cleavable to yield the insulin polypeptide, and an oligomer coupled to the insulin polypeptide portion of the proinsulin polypeptide.

The proinsulin polypeptide comprising an insulin polypeptide coupled to one or more peptides by peptide bond(s) that are cleavable to yield the insulin polypeptide may be various proinsulin polypeptides including, but not limited to, the proinsulin polypeptides described above with reference to the methods of synthesizing proinsulin polypeptide-oligomer conjugates. The oligomer may be various oligomers including, but not limited to, the oligomers described above with reference to the methods of synthesizing proinsulin polypeptide-oligomer conjugates. The oligomer preferably comprises a hydrophilic moiety and a lipophilic moiety. Proinsulin polypeptide-oligomer conjugates according to the present invention may be synthesized by various methods as will be understood by those skilled in the art including, but not limited to, the methods of synthesizing proinsulin polypeptide-oligomer conjugates described above.

According to yet other embodiments, a method of synthesizing a C-peptide polypeptide-oligomer conjugate includes contacting a pro-C-peptide polypeptide comprising a C-peptide polypeptide coupled to one or more peptides by peptide bond(s) that are cleavable to yield the C-peptide polypeptide with an oligomer under conditions sufficient to couple the oligomer to the C-peptide polypeptide portion of the pro-C-peptide polypeptide and provide a pro-C-peptide polypeptide-oligomer conjugate, and cleaving the one or more peptides from the pro-C-peptide polypeptide-oligomer conjugate to provide the C-peptide polypeptide-oligomer conjugate.

The pro-C-peptide polypeptide may be various pro-C-peptide polypeptides as will be understood by those skilled in the art. Preferably, the pro-C-peptide polypeptide is a proinsulin polypeptide, and, more preferably, the pro-C-peptide polypeptide is proinsulin.

The C-peptide polypeptide may be various C-peptide polypeptides as will be understood by those skilled in the art. Preferably, the C-peptide polypeptide is C-peptide.

The one or more peptides coupled to the C-peptide polypeptide may be various peptides as will be understood by those skilled in the art. Preferably, the one or more peptides comprise an insulin polypeptide. More preferably, the one or more polypeptides is an insulin polypeptide. The insulin polypeptide may be devoid of lysine residues, which may reduce the amount of oligomeric reagents utilized to conjugate the pro-C-peptide polypeptide. Still more preferably, the one or more peptides is insulin or insulin coupled at the N-terminus of the B-chain to a leader peptide.

The peptide bonds are bonds that may be cleaved in various ways as will be understood by those skilled in the art. Preferably, the peptide bonds are bonds that may be enzymatically cleaved by enzymes including, but not limited to, trypsin, carboxy peptidase B, thrombin, pepsin, and chymotripsin. Peptide bonds that may be enzymatically cleaved will be understood by those skilled in the art and include, but are not limited to, Arg-Arg, Thr-Arg, Ala-Arg, Thr-Arg-Arg, Thr-Lys, Arg-Gly, and Arg-Phe.

The oligomer may be various oligomers as will be understood by those skilled in the art. In general, the oligomer may be any oligomer capable of being coupled to a polypeptide as will be understood by those skilled in the art. For example, the oligomer may be a poly-dispersed oligomer as described in U.S. Pat. No. 4,179,337 to Davis et al.; U.S. Pat. No. 5,567,422 to Greenwald; U.S. Pat. No. 5,359,030 to Ekwuribe; U.S. Pat. No. 5,438,040 to Ekwuribe, U.S. Pat. No. 5,681,811 to Ekwuribe, and U.S. Pat. No. 6,309,633 to Ekwuribe et al. As another example, the oligomer may be a non-polydispersed oligomer as described in U.S. patent application Ser. No. 09/873,731 filed Jun. 4, 2001 by Ekwuribe et al. entitled "Methods of Synthesizing Substantially Monodispersed Mixtures of Polymers Having Polyethylene Glycol Mixtures"; U.S. patent application Ser. No. 09/873,797 filed Jun. 4, 2001 by Ekwuribe et al. entitled "Mixtures of Drug-Oligomer Conjugates Comprising Polyalkylene Glycol, Uses Thereof, and Methods of Making Same"; and U.S. patent application Ser. No. 09/873,899 filed Jun. 4, 2001 by Ekwuribe et al. entitled "Mixtures of Insulin Drug-Oligomer Conjugates Comprising Polyalkylene Glycol, Uses Thereof, and Methods of Making Same."

The oligomer preferably comprises a hydrophilic moiety as will be understood by those skilled in the art including, but not limited to, polyalkylene glycols such as polyethylene glycol or polypropylene glycol, polyoxyethylenated polyols, copolymers thereof and block copolymers thereof, provided that the hydrophilicity of the block copolymers is maintained. The hydrophilic moiety is preferably a polyalkylene glycol moiety. The polyalkylene glycol moiety has at least 1, 2, 3, 4, 5, 6 or 7 polyalkylene glycol subunits. The polyalkylene glycol moiety preferably has between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. The polyalkylene glycol moiety more preferably has between a lower limit of 2, 3, 4, 5, or 6 and an upper limit of 5, 6, 7, 8, 9, 10, 11, 12, 13, 14, 15, 16, 17, 18, 19, or 20 polyalkylene glycol subunits. Even more preferably, the polyalkylene glycol moiety has between a lower limit of 3, 4, 5, or 6 and an upper limit of 5, 6, 7, 8, 9, 10, 11, or 12 polyalkylene glycol subunits. The polyalkylene glycol moiety still more preferably has between a lower limit of 4, 5, or 6 and an upper limit of 6, 7, or 8 polyalkylene glycol subunits. The polyalkylene glycol moiety most preferably has 7 polyalkylene glycol subunits. The polyalkylene glycol moiety of the oligomer is preferably a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety preferably has a uniform (i.e., not random) structure. An exemplary polypropylene glycol moiety having a uniform structure is as follows:

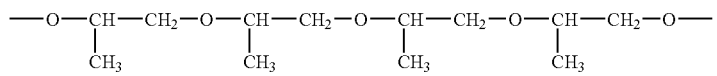

This uniform polypropylene glycol structure may be described as having only one methyl substituted carbon atom adjacent each oxygen atom in the polypropylene glycol chain. Such uniform polypropylene glycol moieties may exhibit both lipophilic and hydrophilic characteristics.

The oligomer may comprise one or more other moieties as will be understood by those skilled in the art including, but not limited to, additional hydrophilic moieties, lipophilic moieties, spacer moieties, linker moieties, and terminating moieties. The various moieties in the oligomer are covalently coupled to one another by either hydrolyzable or non-hydrolyzable bonds.

The oligomer may further comprise one or more additional hydrophilic moieties (i.e., moieties in addition to the polyalkylene glycol moiety) including, but not limited to, sugars, polyalkylene glycols, and polyamine/PEG copolymers. Adjacent polyalkylene glycol moieties will be considered to be the same moiety if they are coupled by ether bonds. For example, the moiety

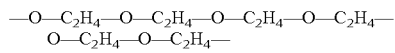

is a single polyethylene glycol moiety having six polyethylene glycol subunits. If this moiety were the only hydrophilic moiety in the oligomer, the oligomer would not contain an additional hydrophilic moiety. Adjacent polyethylene glycol moieties will be considered to be different moieties if they are coupled by a bond other than an ether bond. For example, the moiety is a polyethylene glycol moiety having four polyethylene glycol subunits and an additional hydrophilic moiety having two polyethylene glycol subunits. Preferably, oligomers according to embodiments of the present invention comprise a polyalkylene glycol moiety and no additional hydrophilic moieties.

The oligomer preferably further comprises one or more lipophilic moieties as will be understood by those skilled in the art. The lipophilic moiety has at least 1, 2, 3, 4, 5, or 6 carbon atoms. The lipophilic moiety preferably has between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety more preferably has between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or carbon atoms. The lipophilic moiety even more preferably has between a lower limit of 3, 4, 5, 6, 7, 8, or 9 and an upper limit of 4, 5, 6, 7, 8, 9, 10, 11, 12, 13, or 14 carbon atoms. The lipophilic moiety still more preferably has between a lower limit of 3, 4, 5, 6, or 7 and an upper limit of 6, 7, 8, 9, or 10 carbon atoms. The lipophilic moiety most preferably has 6 carbon atoms. The lipophilic moiety is preferably selected from the group consisting of saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaentoate, and docosahexaenoate; and saturated fatty acid moieties such as acetate, caproate, caprylate, caprate, laurate, arachidate, behenate, lignocerate, and cerotate.

The oligomer may further comprise one or more spacer moieties as will be understood by those skilled in the art. Spacer moieties may, for example, be used to separate a hydrophilic moiety from a lipophilic moiety, to separate a lipophilic moiety or hydrophilic moiety from the C-peptide polypeptide, to separate a first hydrophilic or lipophilic moiety from a second hydrophilic or lipophilic moiety, or to

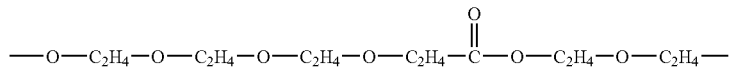

separate a hydrophilic moiety or lipophilic moiety from a linker moiety. Spacer moieties are preferably selected from the group consisting of sugar, cholesterol and glycerine moieties. Sugar moieties may be various sugar moieties as will be understood by those skilled in the art including, but not limited to, monosaccharide moieties and disaccharide moieties. Preferred monosaccharide moieties have between 4 and 6 carbon atoms.

The oligomer may further comprise one or more linker moieties that are used to couple the oligomer with the C-peptide polypeptide as will be understood by those skilled in the art. Linker moieties are preferably selected from the group consisting of alkyl and fatty acid moieties. The alkyl linker moiety may be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The alkyl linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms, and preferably has between 1, 2, 3, 4, or 5 and 8, 9, 10, 11, or 12 carbon atoms. The fatty acid linker moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate. The fatty acid linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms and preferably has between 1, 2, 3, 4, or 5 and 8, 10, 12, 14 or 16 carbon atoms.

The oligomer may further comprise one or more terminating moieties at the one or more ends of the oligomer, which are not coupled to the C-peptide polypeptide. The terminating moiety is preferably an alkyl or alkoxy moiety. The alkyl or alkoxy moiety preferably has between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety more preferably has between a lower limit of 1, 2, 3, 4, 5, 6, or 7 and an upper limit of 5, 6, 7, 8, 9, 10, 11, 12, 13, or 14 carbon atoms. The alkyl or alkoxy moiety even more preferably has between a lower limit of 1, 2, 3, 4, or 5 and an upper limit of 5, 6, 7, 8, 9, or 10 carbon atoms. The alkyl or alkoxy moiety still more preferably has between a lower limit of 1, 2, 3, or 4 and an upper limit of 5, 6, or 7 carbon atoms. The alkyl moiety may be a linear or branched, saturated or unsaturated alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety is more preferably a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. Most preferably, the terminating moiety is methyl or methoxy. While the terminating moiety is preferably an alkyl or alkoxy moiety, it is to be understood that the terminating moiety may be various moieties as will be understood by those skilled in the art including, but not limited to, sugars, cholesterol, alcohols, and fatty acids.

According to other embodiments of the present invention, the oligomer comprises the structure of Formula XI:

$$A\text{-}L_j\text{-}G_k\text{-}R\text{-}G'_m\text{-}R'\text{-}G''_n\text{-}T \tag{XI}$$

wherein:

A is an activatable moiety;

L is a linker moiety;

G, G' and G'' are individually selected spacer moieties;

R is a lipophilic moiety and R' is a polyalkylene glycol moiety, or R' is the lipophilic moiety and R is the polyalkylene glycol moiety;

T is a terminating moiety; and j, k, m and n are individually 0 or 1.

According to these embodiments of the present invention, the polyalkylene glycol moiety has at least 1, 2, 3, 4, 5, 6 or 7 polyalkylene glycol subunits. The polyalkylene glycol moiety preferably has between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more polyalkylene glycol subunits. The polyalkylene glycol moiety more preferably has between a lower limit of 2, 3, 4, 5, or 6 and an upper limit of 5, 6, 7, 8, 9, 10, 11, 12, 13, 14, 15, 16, 17, 18, 19, or 20 polyalkylene glycol subunits. Even more preferably, the polyalkylene glycol moiety has between a lower limit of 3, 4, 5, or 6 and an upper limit of 5, 6, 7, 8, 9, 10, 11, or 12 polyalkylene glycol subunits. The polyalkylene glycol moiety still more preferably has between a lower limit of 4, 5, or 6 and an upper limit of 6, 7, or 8 polyalkylene glycol subunits. The polyalkylene glycol moiety most preferably has 7 polyalkylene glycol subunits. The polyalkylene glycol moiety of the oligomer is preferably a lower alkyl polyalkylene glycol moiety such as a polyethylene glycol moiety, a polypropylene glycol moiety, or a polybutylene glycol moiety. When the polyalkylene glycol moiety is a polypropylene glycol moiety, the moiety preferably has a uniform (i.e., not random) structure. An exemplary polypropylene glycol moiety having a uniform structure is as follows:

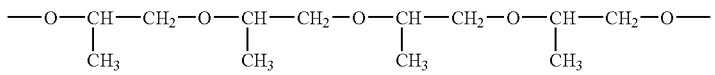

This uniform polypropylene glycol structure may be described as having only one methyl substituted carbon atom adjacent each oxygen atom in the polypropylene glycol chain. Such uniform polypropylene glycol moieties may exhibit both lipophilic and hydrophilic characteristics.

According to these embodiments of the present invention, the lipophilic moiety is a lipophilic moiety as will be understood by those skilled in the art. The lipophilic moiety has at least 1, 2, 3, 4, 5, or 6 carbon atoms. The lipophilic moiety preferably has between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30 carbon atoms. The lipophilic moiety more preferably has between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or carbon atoms. The lipophilic moiety even more preferably has between a lower limit of 3, 4, 5, 6, 7, 8, or 9 and an upper limit of 4, 5, 6, 7, 8, 9, 10, 11, 12, 13, or 14 carbon atoms. The lipophilic moiety still more preferably has between a lower limit of 3, 4, 5, 6, or 7 and an upper limit of 6, 7, 8, 9, or 10 carbon atoms. The lipophilic moiety most preferably has 6 carbon atoms. The lipophilic moiety is preferably selected from the group consisting of saturated or unsaturated, linear or branched alkyl moieties, saturated or unsaturated, linear or branched fatty acid moieties, cholesterol, and adamantane. Exemplary alkyl moieties include, but are not limited to, saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. Exemplary fatty acid moieties include, but are not limited to, unsaturated fatty acid moieties such as lauroleate, myristoleate, palmitoleate, oleate, elaidate, erucate, linoleate, linolenate, arachidonate, eicosapentaentoate, and docosahexaenoate; and saturated fatty acid moieties such as acetate, caproate, caprylate, caprate, laurate, arachidate, behenate, lignocerate, and cerotate.

According to these embodiments of the present invention, the spacer moieties, G, G' and G", are spacer moieties as will be understood by those skilled in the art. Spacer moieties are preferably selected from the group consisting of sugar moieties, cholesterol and glycerine moieties. Sugar moieties may be various sugar moieties as will be understood by those skilled in the art including, but not limited to, monosaccharide moieties and disaccharide moieties. Preferred monosaccharide moieties have between 4 and 6 carbon atoms. Preferably, oligomers of these embodiments do not include spacer moieties (i.e., k, m and n are preferably 0).

According to these embodiments of the present invention, the linker moiety, L, may be used to couple the oligomer with the C-peptide polypeptide as will be understood by those skilled in the art. Linker moieties are preferably selected from the group consisting of alkyl and fatty acid moieties. The alkyl linker moiety may be a saturated or unsaturated, linear or branched alkyl moiety as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkoxy moiety may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The alkyl linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms, and preferably has between 1, 2, 3, 4, or 5 and 8, 9, 10, 11, or 12 carbon atoms. The fatty acid linker moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate. The fatty acid linker moiety may have between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms and preferably has between 1, 2, 3, 4, or 5 and 8, 10, 12, 14 or 16 carbon atoms.

According to these embodiments of the present invention, the terminating moiety, T, is preferably an alkyl or alkoxy moiety. The alkyl or alkoxy moiety preferably has between a lower limit of 1, 2, 3, 4, 5, 6, 7, 8, 9, 10, 11, 12, 13, 14, 15, 16, 17, 18, 19, or 20 and an upper limit of 5, 6, 7, 8, 9, 10, 11, 12, 13, 14, 15, 16, 17, 18, 19, 20, 21, 22, 23, 24, 25, 26, 27, 28, 29, or 30 carbon atoms. The alkyl or alkoxy moiety more preferably has between a lower limit of 1, 2, 3, 4, 5, 6, or 7 and an upper limit of 5, 6, 7, 8, 9, 10, 11, 12, 13, or 14 carbon atoms. The alkyl or alkoxy moiety even more preferably has between a lower limit of 1, 2, 3, 4, or 5 and an upper limit of 5, 6, 7, 8, 9, or 10 carbon atoms. The alkyl or alkoxy moiety still more preferably has between a lower limit of 1, 2, 3, or 4 and an upper limit of 5, 6, or 7 carbon atoms. The alkyl moiety may be various linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. Exemplary alkoxy moieties may be various alkoxy moieties including, but not limited to, methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, octadecyloxy, nonadecyloxy, eicosyloxy, isopropoxy, sec-butoxy, tert-butoxy, 2-methylbutoxy, tert-pentyloxy, 2-methyl-pentyloxy, 3-methylpentyloxy, 2-ethylhexyloxy, 2-propylpentyloxy, vinyloxy, allyloxy, 1-butenyloxy, 2-butenyloxy, ethynyloxy, 1-propynyloxy, and 2-propynyloxy. The terminating moiety is more preferably a lower alkyl moiety such as methyl, ethyl, propyl, isopropyl, butyl, sec-butyl, tert-butyl, pentyl, or tert-pentyl, or a lower alkoxy moiety such as methoxy, ethoxy, propoxy, isopropoxy, butoxy, sec-butoxy, tert-butoxy, pentyloxy, or tert-pentyloxy. Most preferably, the terminating moiety is methyl or methoxy. While the terminating moiety is preferably an alkyl or alkoxy moiety, it is to be understood that the terminating moiety may be various moieties as will be understood by those skilled in the art including, but not limited to, sugar moieties, cholesterol, alcohols, and fatty acid moieties.

According to these embodiments of the present invention, the activatable moiety, A, is a moiety that allows for the coupling of the oligomer to an activating agent to form an activated oligomer capable of coupling with the proinsulin polypeptide. The activatable moiety may be various activatable moieties as will be understood by those skilled in the art including, but not limited to, —C(O)—OH, C(S)—OH, —C(S)—SH, —OH, —SH, and $NH_2$.

In still other embodiments, the oligomer comprises the structure of Formula XII:

A-X(CH$_2$)$_m$Y(C$_2$H$_4$O)$_n$R    (XII)

wherein:

A is —C(O)—OH, C(S)—OH, —C(S)—SH, —OH, —SH, or $NH_2$;

X is an oxygen atom or a covalent bond, with the proviso X is not an oxygen atom when A is —OH;

Y is an ester, an ether, a carbamate, a carbonate, or an amide bonding moiety, and is preferably an ether bonding moiety;

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably has between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, is more preferably between a lower limit of 2, 3, 4, 5, or 6 and an upper limit of 5, 6, 7, 8, 9, 10, 11, 12, 13, 14, 15, 16, 17, 18, 19, or 20, is even more preferably between a lower limit of 3, 4, 5, or 6 and an upper limit of 5, 6, 7, 8, 9, 10, 11, or 12 polyalkylene glycol subunits, is still more preferably between a lower limit of 4, 5, or 6 and an upper limit of 6, 7, or 8 polyalkylene glycol subunits, and is most preferably 7; and R is an alkyl moiety, a sugar moiety, cholesterol, adamantane, an alcohol moiety, or a fatty acid moiety. The alkyl moiety may be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety is more preferably a lower alkyl moiety such as methyl, ethyl, propyl, isopropyl, butyl, sec-butyl, tert-butyl, pentyl, or tert-pentyl. The alkyl moiety is still more preferably a $C_1$ to $C_3$ alkyl. The alkyl moiety is most preferably methyl. The fatty acid moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate.

In still other embodiments, the oligomer comprises the structure of Formula XIII:

A-(CH$_2$)$_m$(OC$_2$H$_4$)$_n$OR    (XIII)

wherein:

A is —C(O)—OH, C(S)—OH, —C(S)—SH, —OH, —SH, or $NH_2$;

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably has between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, is more preferably between a lower limit of 2, 3, 4, 5, or 6 and an upper limit of 5, 6, 7, 8, 9, 10, 11, 12, 13, 14, 15, 16, 17, 18, 19, or 20, is even more preferably between a lower limit of 3, 4, 5, or 6 and an upper limit of 5, 6, 7, 8, 9, 10, 11, or 12 polyalkylene glycol subunits, is still more preferably between a lower limit of 4, 5, or 6 and an upper limit of 6, 7, or 8 polyalkylene glycol subunits, and is most preferably 7; and R is an alkyl moiety, a sugar moiety, cholesterol, adamantane, an alcohol moiety, or a fatty acid moiety. The alkyl moiety may be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety is more preferably a lower alkyl moiety such as methyl, ethyl, propyl, isopropyl, butyl, sec-butyl, tert-butyl, pentyl, or tert-pentyl. The alkyl moiety is still more preferably a $C_1$ to $C_3$ alkyl. The alkyl moiety is most preferably methyl. The fatty acid moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate.

In yet other embodiments, the oligomer comprises the structure of Formula XIV:

(XIV)

wherein:

m is between a lower limit of 1, 2, 3, 4, 5, 6, 7, 8, 9, 10, 11, 12, 13, 14, 15, 16, 17, 18, 19, or 20 and an upper limit of 4, 5, 6, 7, 8, 9, 10, 11, 12, 13, 14, 15, 16, 17, 18, 19, 20, 21, 22, 23, 24, 25, 26, 27, 28, 29, or 30, is more preferably between a lower limit of 2, 3, 4, 5, 6, 7, 8, 9, or 10 and an upper limit of 4, 5, 6, 7, 8, 9, 10, 11, 12, 13, 14, 15, 16, 17, 18, 19, 20, 21, or 22, is even more preferably between a lower limit of 3, 4, 5, 6, 7, 8, or 9 and an upper limit of 4, 5, 6, 7, 8, 9, 10, 11, 12, 13, or 14, and is still more preferably has between a lower limit of 3, 4, 5, 6, or 7 and an upper limit of 6, 7, 8, 9, or 10;

n is between a lower limit of 1, 2, 3, 4, 5, 6, 7, 8, 9, 10, 11, 12, 13, 14, 15, 16, 17, 18, 19, or 20 and an upper limit of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, is more preferably between a lower limit of 2, 3, 4, 5, or 6 and an upper limit of 5, 6, 7, 8, 9, 10, 11, 12, 13, 14, 15, 16, 17, 18, 19, or 20, is even more preferably between a lower limit of 3, 4, 5, or 6 and an upper limit of 5, 6, 7, 8, 9, 10, 11, or 12 polyalkylene glycol subunits, is still more preferably between a lower limit of 4, 5, or 6 and an upper limit of 6, 7, or 8 polyalkylene glycol subunits, and is most preferably 7; and R is an alkyl moiety, a sugar moiety, cholesterol, adamantane, an alcohol moiety, or a fatty acid moiety. The alkyl moiety may be a linear or branched, saturated or unsaturated alkyl moieties as will be understood by those skilled in the art including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl, eicosyl, isopropyl, sec-butyl, tert-butyl, 2-methylbutyl, tert-pentyl, 2-methyl-pentyl, 3-methylpentyl, 2-ethylhexyl, 2-propylpentyl, vinyl, allyl, 1-butenyl, 2-butenyl, ethynyl, 1-propynyl, and 2-propynyl. The alkyl moiety is more preferably a lower alkyl moiety such as methyl, ethyl, propyl, isopropyl, butyl, sec-butyl, tert-butyl, pentyl, or tert-pentyl. The alkyl moiety is still more preferably a $C_1$ to $C_3$ alkyl. The alkyl moiety is most preferably methyl. The fatty acid moiety may be a saturated or unsaturated, linear or branched fatty acid moiety as will be understood by those skilled in the art including, but not limited to, lauroleate, myristoleate, palmitoleate, oleate, elaidate, erucate, linoleate, linolenate, arachidonate, eicosapentaentoate, docosahexaenoate, acetate, caproate, caprylate, caprate, laurate, arachidate, behenate, lignocerate, and cerotate.

In the various embodiments of method for synthesizing C-peptide polypeptide oligomer conjugates described above, the oligomer is covalently coupled to the C-peptide polypeptide. In some embodiments, the oligomer is coupled to the C-peptide polypeptide utilizing a hydrolyzable bond (e.g., an ester or carbonate bond). A hydrolyzable coupling may provide a C-peptide polypeptide-oligomer conjugate that acts as a prodrug. In certain instances, for example where the C-peptide polypeptide-oligomer conjugate is biologically inactive (i.e., the conjugate lacks the ability to affect the body through the C-peptide polypeptide's primary mechanism of action), a hydrolyzable coupling may provide for a time-release or controlled-release effect, providing the biologically active C-peptide polypeptide over a given time period as one or more oligomers are cleaved from their respective biologically inactive C-peptide polypeptide-oligomer conjugates to provide the biologically active C-peptide polypeptide. In other embodiments, the oligomer is coupled to the C-peptide polypeptide utilizing a non-hydrolyzable bond (e.g., a carbamate, amide, or ether bond). Use of a non-hydrolyzable bond may be preferable when it is desirable to allow the biologically inactive C-peptide polypeptide-oligomer conjugate to circulate in the bloodstream for an extended period of time, preferably at least 2 hours. When the oligomer is coupled to the C-peptide polypeptide utilizing a bonding moiety that comprises a carbonyl moiety, such as an ester, a carbamate, a carbonate, or an amide bonding moiety, the resulting C-peptide polypeptide-oligomer conjugate is a C-peptide polypeptide-acyl oligomer conjugate.

Oligomers employed in the various methods of synthesizing C-peptide polypeptide-oligomer conjugates described above are commercially available or may be synthesized by various methods as will be understood by those skilled in the art. For example, polydispersed oligomers may be synthesized by the methods provided in one or more of the following references: U.S. Pat. No. 4,179,337 to Davis et al.; U.S. Pat. No. 5,567,422 to Greenwald; U.S. Pat. No. 5,359,030 to Ekwuribe; U.S. Pat. No. 5,438,040 to Ekwuribe, U.S. Pat. No. 5,681,811 to Ekwuribe, U.S. Pat. No. 6,309,633 to Ekwuribe et al. Non-polydispersed (e.g., substantially monodispersed and monodispersed) oligomers may be synthesized by methods provided in one or more of the following references: U.S. patent application Ser. No. 09/873,731 filed Jun. 4, 2001 by Ekwuribe et al. entitled "Methods of Synthesizing Substantially Monodispersed Mixtures of Polymers Having Polyethylene Glycol Mixtures"; U.S. patent application Ser. No. 09/873,797 filed Jun. 4, 2001 by Ekwuribe et al. entitled "Mixtures of Drug-Oligomer Conjugates Comprising Polyalkylene Glycol, Uses Thereof, and Methods of Making Same"; and U.S. patent application Ser. No. 09/873,899 filed Jun. 4, 2001 by Ekwuribe et al. entitled "Mixtures of Insulin Drug-Oligomer Conjugates Comprising Polyalkylene Glycol, Uses Thereof, and Methods of Making Same". Oligomers according to embodiments of the present invention are preferably substantially monodispersed and are more preferably monodispersed. Exemplary methods for synthesizing preferred monodispersed oligomers are provided in Examples 1 through 10 below.

The contacting of the pro-C-peptide polypeptide with the oligomer under conditions sufficient to provide a pro-C- peptide polypeptide-oligomer conjugate may be performed utilizing various conditions as will be understood by those skilled in the art. Preferably, the contacting of the pro-C-peptide polypeptide with the oligomer under conditions sufficient to provide a pro-C-peptide polypeptide-oligomer conjugate comprises contacting the oligomer with an activating agent under conditions sufficient to provide an activated oligomer; and contacting the activated oligomer with the pro-C-peptide polypeptide under conditions sufficient to provide the pro-C-peptide polypeptide conjugate. The activated oligomer may be formed ex situ or in situ.

The activating agent may be various activating agents capable of activating one or more of the oligomers described above so that the oligomer is capable of reacting with nucleophilic hydroxyl functions and/or amino functions in the proinsulin polypeptide as will be understood by those skilled in the art including, but not limited to, N-hydroxysuccinimide, p-nitrophenyl chloroformate, 1,3-dicyclohexylcarbodiimide, and hydroxybenzotriazide.

One skilled in the art will understand the conditions sufficient to couple the activating agent to the oligomer to provide an activated oligomer. For example, one skilled in the art can refer to R. C. Larock, COMPREHENSIVE ORGANIC TRANSFORMATIONS. A GUIDE TO FUNCTIONAL GROUP PREPARATIONS (2d Edition, New York, Wiley-VCH, 1999).

The conditions sufficient to couple the activated oligomer to the pro-C-peptide polypeptide will be understood to one of skill in the art. For example, the pro-C-peptide polypeptide may be dissolved in a dipolar aprotic solvent, such as dimethylsulfoxide, to provide a pro-C-peptide polypeptide solution. A buffering agent, such as triethylamine, may be added to the pro-C-peptide polypeptide solution. The activated oligomer dissolved in an anydrous solvent such as acetonitrile may then be added to the pro-C-peptide polypeptide solution. One skilled in the art may also refer to R. C. Larock, COMPREHENSIVE ORGANIC TRANSFORMATIONS. A GUIDE TO FUNCTIONAL GROUP PREPARATIONS (2d Edition, New York, Wiley-VCH, 1999). The molar ratio of activated oligomer to pro-C-peptide polypeptide is preferably greater than about 1:1, is more preferably greater than about 2:1, is even more preferably greater than about 3:1, is still more preferably greater than about 4:1, and is still even more preferably greater than about 5:1.

In the various embodiments of methods for synthesizing C-peptide polypeptide-oligomer conjugates described above, more than one oligomer (i.e., a plurality of oligomers) may be coupled to the C-peptide polypeptide portion of the pro-C-peptide polypeptide. The oligomers in the plurality are preferably the same. However, it is to be understood that the oligomers in the plurality may be different from one another, or, alternatively, some of the oligomers in the plurality may be the same and some may be different. When a plurality of oligomers are coupled to the C-peptide polypeptide portion of the pro-C-peptide polypeptide, it may be preferable to couple one or more of the oligomers to the C-pepdtide polypeptide portion of the pro-C-peptide polypeptide with hydrolyzable bonds and couple one or more of the oligomers to the C-peptide polypeptide portion of the pro-C-peptide polypeptide with non-hydrolyzable bonds. Alternatively, all of the bonds coupling the plurality of oligomers to the C-peptide polypeptide portion of the pro-C-peptide polypeptide may be hydrolyzable, but have varying degrees of hydrolyzability such that, for example, one or more of the oligomers is rapidly removed from the C-peptide polypeptide or C-peptide polypeptide portion of the pro-C-peptide polypeptide by hydrolysis in the body and one or more of the oligomers is slowly removed from the C-peptide polypeptide or C-peptide polypeptide portion by hydrolysis in the body.

In the various embodiments of methods for synthesizing C-peptide polypeptide-oligomer conjugates described above, the oligomer may be coupled to the C-peptide polypeptide portion of the pro-C-peptide polypeptide at various nucleophilic residues of the C-peptide polypeptide portion including, but not limited to, nucleophilic hydroxyl functions and/or amino functions. A nucleophilic hydroxyl function may be found, for example, at serine and/or tyrosine residues, and a nucleophilic amino function may be found, for example, at histidine and/or lysine residues, and/or at the one or more N-termini of the polypeptide. When an oligomer is coupled to the one or more N-termini of the proinsulin polypeptide, the coupling preferably forms a secondary amine.

The cleaving of the one or more peptides from the pro-C-peptide polypeptide-oligomer conjugate to provide the C-peptide polypeptide-oligomer conjugate may be performed by various processes as will be understood by those skilled in the art. Preferably, the cleaving of the one or more peptides from the pro-C-peptide polypeptide-oligomer conjugate comprises contacting the pro-C-peptide polypeptide-oligomer conjugate with one or more enzymes that are capable of cleaving the bond(s) between the one or more peptides and the C-peptide polypeptide under conditions sufficient to cleave the one or more peptides from the pro-C-peptide polypeptide-oligomer conjugate. As described in various references, for example, Kemmler et al; "Studies on the Conversion of Proinsulin to Insulin," *J. Biol. Chem.*, 246: 6786-6791 (1971), one skilled in the art will understand how to select appropriate enzymes in view of the particular peptide bond(s) to be cleaved and how to provide conditions sufficient to cleave the one or more peptides from the pro-C-peptide polypeptide-oligomer conjugate. The one or more enzymes preferably comprise various enzymes including, but not limited to, trypsin, chymotrypsin, carboxy peptidase B, and mixtures thereof. More preferably, the one or more enzymes are selected from the group consisting of trypsin, carboxy peptidase B, and mixtures thereof.

The present invention will now be described with reference to the following examples. It should be appreciated that these examples are for the purposes of illustrating aspects of the present invention, and do not limit the scope of the invention as defined by the claims.

EXAMPLES

Example 1

Synthesis of 6-(2-{2-[2-(2-{2-[2-(2-methoxyethoxy)ethoxy]-ethoxy}-ethoxy)-ethoxy]-ethoxy}-ethoxy)-hexanoic acid 2,5-dioxo-pyrrolidin-1-yl ester (8)

Hexaethylene glycol monobenzyl ether (1). An aqueous sodium hydroxide solution prepared by dissolving 3.99 g (100 mmol) NaOH in 4 ml water was added slowly to monodispersed hexaethylene glycol (28.175 g, 25 ml, 100 mmol). Benzyl chloride (3.9 g, 30.8. mmol, 3.54 ml) was added and the reaction mixture was heated with stirring to 100° C. for 18 hours. The reaction mixture was then cooled, diluted with brine (250 ml) and extracted with methylene chloride (200 ml×2). The combined organic layers were washed with brine once, dried over $Na_2SO_4$, filtered and concentrated in vacuo to a dark brown oil. The crude product mixture was purified via flash chromatography (silica gel, gradient elution: ethyl acetate to 9/1 ethyl acetate/methanol) to yield 8.099 g (70%) of monodispersed compound 1 as a yellow oil.

Ethyl 6-methylsulfonyloxyhexanoate (2). A solution of monodispersed ethyl 6-hydroxyhexanoate (50.76 ml, 50.41 g, 227 mmol) in dry dichloromethane (75 ml) was chilled in an ice bath and placed under a nitrogen atmosphere. Triethylamine (34.43 ml, 24.99 g, 247 mmol) was added. A solution of methanesulfonyl chloride (19.15 ml, 28.3 g, 247 mmol) in dry dichloromethane (75 ml) was added dropwise from an addition funnel. The mixture was stirred for three and one half hours, slowly being allowed to come to room temperature as the ice bath melted. The mixture was filtered through silica gel, and the filtrate was washed successively with water, saturated $NaHCO_3$, water and brine. The organics were dried over $Na_2SO_4$, filtered and concentrated in vacuo to a pale yellow oil. Final purification of the crude product was achieved by flash chromatography (silica gel, 1/1 hexanes/ethyl acetate) to give the monodispersed compound 2 (46.13 g, 85%) as a clear, colorless oil. FAB MS: m/e 239 (M+H), 193 (M—$C_2H_5O$).

6-{2-[2-(2-{2-[2-(2-Benzyloxyethoxy)ethoxy]ethoxy}-ethoxy)-ethoxy]-ethoxy}-hexanoic acid ethyl ester (3). Sodium hydride (3.225 g or a 60% oil dispersion, 80.6 mmol) was suspended in 80 ml of anhydrous toluene, placed under a nitrogen atmosphere and cooled in an ice bath. A solution of the monodispersed alcohol 9 (27.3 g, 73.3 mmol) in 80 ml dry toluene was added to the NaH suspension. The mixture was stirred at 0° C. for thirty minutes, allowed to come to room temperature and stirred for another five hours, during which time the mixture became a clear brown solution. The monodispersed mesylate 10 (19.21 g, 80.6 mmol) in 80 ml dry toluene was added to the NaH/alcohol mixture, and the combined solutions were stirred at room temperature for three days. The reaction mixture was quenched with 50 ml methanol and filtered through basic alumina. The filtrate was concentrated in vacuo and purified by flash chromatography (silica gel, gradient elution: 3/1 ethyl acetate/hexanes to ethyl acetate) to yield the monodispersed compound 3 as a pale yellow oil (16.52 g, 44%). FAB MS: m/e 515 (M+H).

6-{2-[2-(2-{2-[2-(2-hydroxyethoxy)ethoxy]ethoxy}-ethoxy)-ethoxy]-ethoxy}-hexanoic acid ethyl ester (4). Substantially monodispersed benzyl ether 3 (1.03 g, 2.0 mmol) was dissolved in 25 ml ethanol. To this solution was added 270 mg 10% Pd/C, and the mixture was placed under a hydrogen atmosphere and stirred for four hours, at which time TLC showed the complete disappearance of the starting material. The reaction mixture was filtered through Celite 545 to remove the catalyst, and the filtrate was concentrated in vacuo to yield the monodispersed compound 4 as a clear oil (0.67 g, 79%). FAB MS: m/e 425 (M+H), 447 (M+Na).

6-{2-[2-(2-{2-[2-(2-methylsulfonylethoxy)ethoxy]ethoxy}-ethoxy)-ethoxy]-ethoxy}-hexanoic acid ethyl ester (5). The monodispersed alcohol 4 (0.835 g, 1.97 mmol) was dissolved in 3.5 ml dry dichloromethane and placed under a nitrogen atmosphere. Triethylamine (0.301 ml, 0.219 g, 2.16 mmol) was added and the mixture was chilled in an ice bath. After two minutes, the methanesulfonyl chloride (0.16 ml, 0.248 g, 2.16 mmol) was added. The mixture was stirred for 15 minutes at 0° C., then at room temperature for two hours. The reaction mixture was filtered through silica gel to remove the triethylammonium chloride, and the filtrate was washed successively with water, saturated $NaHCO_3$, water and brine. The organics were dried over $Na_2SO_4$, filtered and concentrated in vacuo. The residue was purified by column chromatography (silica gel, 9/1 ethyl acetate/methanol) to give monodispersed compound 5 as a clear oil (0.819 g, 83%). FAB MS: m/e 503 (M+H).

6-(2-{2-[2-(2-{2-[2-(2-methoxyethoxy)ethoxy]-ethoxy}-ethoxy)-ethoxy]-ethoxy}-ethoxy)-hexanoic acid ethyl ester (6). NaH (88 mg of a 60% dispersion in oil, 2.2 mmol) was suspended in anhydrous toluene (3 ml) under $N_2$ and chilled to 0° C. Monodispersed diethylene glycol monomethyl ether (0.26 ml, 0.26 g, 2.2 mmol) that had been dried via azeotropic distillation with toluene was added. The reaction mixture was allowed to warm to room temperature and stirred for four hours, during which time the cloudy grey suspension became clear and yellow and then turned brown. Mesylate 5 (0.50 g, 1.0 mmol) in 2.5 ml dry toluene was added. After stirring at room temperature over night, the reaction was quenched by the addition of 2 ml of methanol and the resultant solution was filtered through silica gel. The filtrate was concentrated in vacuo and the FAB MS: m/e 499 (M+H), 521 (M+Na). Additional purification by preparatory chromatography (silica gel, 19/3 chloroform/methanol) provided the monodispersed compound 6 as a clear yellow oil (0.302 g 57%). FAB MS: m/e 527 (M+H), 549 (M+Na).

6-(2-{2-[2-(2-{2-[2-(2-methoxyethoxy)ethoxy]-ethoxy}-ethoxy)-ethoxy]-ethoxy}-ethoxy)-hexanoic acid (7). Monodispersed ester 6 (0.25 g, 0.46 mmol) was stirred for 18 hours in 0.71 ml of 1 N NaOH. After 18 hours, the mixture was concentrated in vacuo to remove the alcohol and the residue dissolved in a further 10 ml of water. The aqueous solution was acidified to pH 2 with 2 N HCl and the product was extracted into dichloromethane (30 ml×2). The combined organics were then washed with brine (25 ml×2), dried over $Na_2SO_4$, filtered and concentrated in vacuo to yield the monodispersed compound 15 as a yellow oil (0.147 g, 62%). FAB MS: m/e 499 (M+H), 521 (M+Na).

6-(2-{2-[2-(2-{2-[2-(2-methoxyethoxy)ethoxy]-ethoxy}-ethoxy)-ethoxy]-ethoxy}-ethoxy)-hexanoic acid 2,5-dioxo-pyrrolidin-1-yl ester (8). Monodispersed acid 7 (0.209 g, 0.42 mmol) was dissolved in 4 ml of dry dichloromethane and added to a dry flask already containing NHS (N-hydroxysuccinimide) (57.8 mg, 0.502 mmol) and EDC (1-(3-dimethylaminopropyl)-3-ethylcarbodiimide hydrochloride) (98.0 mg, 0.502 mmol) under a $N_2$ atmosphere. The solution was stirred at room temperature overnight and filtered through silica gel to remove excess reagents and the urea formed from the EDC. The filtrate was concentrated in vacuo to provide the activated monodispersed oligomer 8 as a dark yellow oil (0.235 g, 94%). FAB MS: m/e 596 (M+H), 618 (M+Na).

Example 2

Synthesis of Activated $MPEG_7$-$C_8$ (14)

Mesylate of triethylene glycol monomethyl ether (9). To a solution of $CH_2Cl_2$ (100 mL) cooled to 0° C. in an ice bath was added monodispersed triethylene glycol monomethyl ether (25 g, 0.15 mol). Then triethylamine (29.5 mL, 0.22 mol) was added and the solution was stirred for 15 min at 0° C., which was followed by dropwise addition of methanesulfonyl chloride (13.8 mL, 0.18 mol, dissolved in 20 mL $CH_2Cl_2$). The reaction mixture was stirred for 30 min at 0° C., allowed to warm to room temperature, and then stirred for 2 h. The crude reaction mixture was filtered through Celite (washed $CH_2Cl_2$ ~200 mL), then washed with $H_2O$ (300 mL), 5% $NaHCO_3$ (300 mL), $H_2O$ (300 mL), sat. NaCl (300 mL), dried $MgSO_4$, and evaporated to dryness. The oil was then placed on a vacuum line for ~2 h to ensure dryness and afforded the monodispersed compound 9 as a yellow oil (29.15 g, 80% yield).

Heptaethylene glycol monomethyl ether (10). To a solution of monodispersed tetraethylene glycol (51.5 g, 0.27 mol) in THF (1L) was added potassium t-butoxide (14.8 g, 0.13 mol, small portions over ~30 min). The reaction mixture was then stirred for 1 h and then 9 (29.15 g, 0.12 mol) dissolved in THF (90 mL) was added dropwise and the reaction mixture was stirred overnight. The crude reaction mixture was filtered through Celite (washed $CH_2Cl_2$, ~200 mL) and evaporated to dryness. The oil was then dissolved in HCl (250 mL, 1 N) and washed with ethyl acetate (250 mL) to remove excess 9. Additional washings of ethyl acetate (125 mL) may be required to remove remaining 9. The aqueous phase was washed repetitively with $CH_2Cl_2$ (125 mL volumes) until most of the compound 18 has been removed from the aqueous phase. The first extraction will contain 9, 10, and dicoupled side product and should be back extracted with HCl (125 mL, 1N). The organic layers were combined and evaporated to dryness. The resultant oil was then dissolved in $CH_2Cl_2$ (100 mL) and washed repetitively with $H_2O$ (50 mL volumes) until 10 was removed. The aqueous fractions were combined, total volume 500 mL, and NaCl was added until the solution became cloudy and then was washed with $CH_2Cl_2$ (2×500 mL). The organic layers were combined, dried $MgSO_4$, and evaporated to dryness to afford the monodispersed compound 10 as an oil (16.9 g, 41% yield). It may be desirable to repeat one or more steps of the purification procedure to ensure high purity.

8-Bromooctoanate (11). To a solution of monodispersed. 8-bromooctanoic acid (5.0 g, 22 mmol) in ethanol (100 mL) was added $H_2SO_4$ (0.36 mL, 7.5 mmol) and the reaction was heated to reflux with stirring for 3 h. The crude reaction mixture was cooled to room temperature and washed $H_2O$ (100 mL), sat. $NaHCO_3$ (2×100 mL), $H_2O$ (100 mL), dried $MgSO_4$, and evaporated to dryness to afford a clear oil 11 (5.5 g, 98% yield).

$MPEG_7$-$C_8$ ester (12). To a solution of the monodispersed compound 10 (3.0 g, 8.8 mmol) in ether (90 mL) was added potassium t-butoxide (1.2 g, 9.6 mmol) and the reaction mixture was stirred for 1 h. Then dropwise addition of the monodispersed compound 11 (2.4 g, 9.6 mmol), dissolved in ether (10 mL), was added and the reaction mixture was stirred overnight. The crude reaction mixture was filtered through Celite (washed $CH_2Cl_2$, ~200 mL) and evaporated to dryness. The resultant oil was dissolved in ethyl acetate and washed $H_2O$ (2×200 mL), dried $MgSO_4$, and evaporated to dryness. Column chromatography (Silica, ethyl acetate to ethyl acetate/methanol, 10:1) was performed and afforded the monodispersed compound 12 as a clear oil (0.843 g, 19% yield).

$MPEG_7$-$C_8$ acid (13). To the oil of the monodispersed compound 12 (0.70 g, 1.4 mmol) was added 1N NaOH (2.0 mL) and the reaction mixture was stirred for 4 h. The crude reaction mixture was concentrated, acidified (pH~2), saturated with NaCl, and washed $CH_2Cl_2$ (2×50 mL). The organic layers were combined, washed sat. NaCl, dried $MgSO_4$, and evaporated to dryness to afford the monodispersed compound 13 as a clear oil (0.35 g, 53% yield).

Activation of $MPEG_7$-$C_8$ acid. Monodispersed mPEG7-C8-acid 13 (0.31 g, 0.64 mmol) was dissolved in 3 ml of anhydrous methylene chloride and then solution of N-hydroxysuccinimide (0.079 g, 0.69 mmol) and EDCI.HCl (135.6 mg, 0.71 mmol) in anhydrous methylene chloride added. Reaction was stirred for several hours, then washed with 1N HCl, water, dried over $MgSO_4$, filtered and concentrated. Crude material was purified by column chromatography, concentrated to afford monodispersed activated $MPEG_7$-$C_8$ 14 as a clear oil and dried via vacuum.

Example 3

Synthesis of Activated $MPEG_7$-$C_{10}$ (19)

10-hydroxydecanoate (15). To a solution of monodispersed 10-hydroxydecanoic acid (5.0 g, 26.5 mmol) in ethanol (100 mL) was added $H_2SO_4$ (0.43 mL, 8.8 mmol) and the reaction was heated to reflux with stirring for 3 h. The crude reaction mixture was cooled to room temperature and washed $H_2O$ (100 mL), sat. $NaHCO_3$ (2×100 mL), $H_2O$ (100 mL), dried $MgSO_4$, and evaporated to dryness to afford the monodispersed compound 15 as a clear oil (6.9 g, 98% yield).

Mesylate of 10-hydroxydecanoate (16). To a solution of $CH_2Cl_2$ (27 mL) was added monodispersed 10-hydroxydecanoate 15 (5.6 g, 26 mmol) and cooled to 0° C. in an ice bath. Then triethylamine (5 mL, 37 mmol) was added and the reaction mixture was stirred for 15-min at 0° C. Then methanesulfonyl chloride (2.7 mL, 24 mmol) dissolved in $CH_2Cl_2$ (3 mL) was added and the reaction mixture was stirred at 0° C. for 30 min, the ice bath was removed and the reaction was stirred for an additional 2 h at room temperature. The crude reaction mixture was filtered through Celite (washed $CH_2Cl_2$, 80 mL) and the filtrate was washed $H_2O$ (100 mL), 5% $NaHCO_3$ (2×100 mL), $H_2O$ (100 mL), sat. NaCl (100 mL), dried $MgSO_4$, and evaporated to dryness to afford the monodispersed compound 16 as a yellowish oil (7.42 g, 97% yield).

$MPEG_7$-$C_{10}$ Ester (17). To a solution of substantially monodispersed heptaethylene glycol monomethyl ether 10 (2.5 g, 7.3 mmol) in tetrahydrofuran (100 mL) was added sodium hydride (0.194 g, 8.1 mmol) and the reaction mixture was stirred for 1 h. Then dropwise addition of mesylate of monodispersed 10-hydroxydecanoate 16 (2.4 g, 8.1 mmol), dissolved in tetrahydrofuran (10 mL), was added and the reaction mixture was stirred overnight. The crude reaction mixture was filtered through Celite (washed $CH_2Cl_2$, ~200 mL) and evaporated to dryness. The resultant oil was dissolved in ethyl acetate and washed $H_2O$ (2×200 mL), dried $MgSO_4$, evaporated to dryness, chromatographed (silica, ethyl acetate/methanol, 10:1), and chromatographed (silica, ethyl acetate) to afford the monodispersed compound 17 as a clear oil (0.570 g, 15%. yield).

$MPEG_7$-$C_{10}$ Acid (18). To the oil of monodispersed $mPEG_7$-$C_{10}$ ester 17 (0.570 g, 1.1 mmol) was added 1N NaOH (1.6 mL) and the reaction mixture was stirred overnight. The crude reaction mixture was concentrated, acidified (pH~2), saturated with NaCl, and washed $CH_2Cl_2$ (2×50 mL). The organic layers were combined, washed sat. NaCl (2×50 mL), dried $MgSO_4$, and evaporated to dryness to afford the monodispersed compound 18 as a clear oil (0.340 g, 62% yield).

Activation of $MPEG_7$-$C_{10}$ Acid. The monodispersed acid 18 was activated using procedures similar to those described above in Example 10 to provide activated $MPEG_7$-$C_{10}$ Oligomer 19.

Example 4

Synthesis of Activated $C_{18}(PEG_6)$ Oliomer (22)

Synthesis of $C_{18}(PEG_6)$ Oligomer (20). Monodispersed stearoyl chloride (0.7 g, 2.31 mmol) was added slowly to a mixture of monodispersed PEG$_6$ (5 g, 17.7 mmol) and pyridine (0.97 g, 12.4 mmol) in benzene. The reaction mixture was stirred for several hours (~5). The reaction was followed by TLC using ethylacetate/methanol as a developing solvent. Then the reaction mixture was washed with water, dried over MgSO$_4$, concentrated and dried via vacuum. Purified monodispersed compound 20 was analyzed by FABMS: m/e 549/M$^+$H.

Activation of C$_{18}$(PEG$_6$) Oligomer. Activation of monodispersed C$_{18}$(PEG$_6$) oligomer was accomplished in two steps:

1) Monodispersed stearoyl-PEG$_6$ 20 (0.8 g, 1.46 mmol) was dissolved in toluene and added to a phosgene solution (10 ml, 20% in toluene) which was cooled with an ice bath. The reaction mixture was stirred for 1 h at 0° C. and then for 3 h at room temperature. Then phosgene and toluene were distilled off and the remaining substantially monodispersed stearoyl PEG6 chloroformate 21 was dried over P$_2$O$_5$ overnight.

2) To a solution of monodispersed stearoyl-PEG$_6$ chloroformate 21 (0.78 g, 1.27 mmol) and TEA (128 mg, 1.27 mmol) in anhydrous methylene chloride, N-hydroxy succinimide (NHS) solution in methylene chloride was added. The reaction mixture was stirred for 16 hours, then washed with water, dried over MgSO$_4$, filtered, concentrated and dried via vacuum to provide the monodispersed activated C$_{18}$(PEG$_6$) oligomer 22.

Example 5

Synthesis of Activated C$_{18}$(PEG$_8$) Oligomer (28)

Tetraethylene glycol monobenzylether (23). To the oil of monodispersed tetraethylene glycol (19.4 g, 0.10 mol) was added a solution of NaOH (4.0 g in 4.0 mL) and the reaction was stirred for 15 mm. Then benzyl chloride (3.54 mL, 30.8 mmol) was added and the reaction mixture was heated to 100° C. and stirred overnight. The reaction mixture was cooled to room temperature, diluted with sat. NaCl (250 mL), and washed CH$_2$Cl$_2$ (2×200 mL). The organic layers were combined, washed sat. NaCl, dried MgSO$_4$, and chromatographed (silica, ethyl acetate) to afford the monodispersed compound 23 as a yellow oil (6.21 g, 71% yield).

Mesylate of tetraethylene glycol monobenzylether (24). To a solution of CH$_2$Cl$_2$ (20 mL) was added monodispersed tetraethylene glycol monobenzylether 23 (6.21 g, 22 mmol) and cooled to 0° C. in an ice bath. Then triethylamine (3.2 mL, 24 mmol) was added and the reaction mixture was stirred for 15 min at 0° C. Then methanesulfonyl chloride (1.7 mL, 24 mmol) dissolved in CH$_2$Cl$_2$ (2 mL) was added and the reaction mixture was stirred at 0° C. for 30 min, the ice bath was removed and the reaction was stirred for an additional 2 h at room temperature. The crude reaction mixture was filtered through Celite (washed CH$_2$Cl$_2$, 80 mL) and the filtrate was washed H$_2$O (100 mL), 5% NaHCO$_3$ (2×100 mL), H$_2$O (100 mL), sat. NaCl (100 mL), and dried MgSO$_4$. The resulting yellow oil was chromatographed on a pad of silica containing activated carbon (10 g) to afford the monodispersed compound 24 as a clear oil (7.10 g, 89% yield).

Octaethylene glycol monobenzylether (25). To a solution of tetrahydrofuran (140 mL) containing sodium hydride (0.43 g, 18 mmol) was added dropwise a solution of monodispersed tetraethylene glycol (3.5 g, 18 mmol) in tetrahydrofuran (10 mL) and the reaction mixture was stirred for 1 h. Then mesylate of monodispersed tetraethylene glycol monobenzylether 24 (6.0 g, 16.5 mmol) dissolved in tetrahydrofuran (10 mL) was added dropwise and the reaction mixture was stirred overnight. The crude reaction mixture was filtered through Celite (washed, CH$_2$Cl$_2$, 250 mL) and the filtrate was washed H$_2$O, dried MgSO$_4$, and evaporated to dryness. The resultant oil was chromatographed (silica, ethyl acetate/methanol, 10:1) and chromatographed (silica, chloroform/methanol, 25:1) to afford the monodispersed compound 25 as a clear oil (2.62 g, 34% yield).

Synthesis of Stearate PEG$_8$-Benzyl (26). To a stirred cooled solution of monodispersed octaethylene glycol monobenzylether 25 (0.998 g, 2.07 mmol) and pyridine (163.9 mg, 2.07 mmol) was added monodispersed stearoyl chloride (627.7 mg, 2.07 mmol) in benzene. The reaction mixture was stirred overnight (18 hours). The next day the reaction mixture was washed with water, dried over MgSO$_4$, concentrated and dried via vacuum. Then the crude product was chromatographed on flash silica gel column, using 10% methanol/90% chloroform. The fractions containing the product were combined, concentrated and dried via vacuum to afford the monodispersed compound 26.

Hydrogenolysis of Stearate-PEG8-Benzyl. To a methanol solution of monodispersed stearate-PEG$_8$-Bzl 26 (0.854 g 1.138 mmol ) Pd/C(10%) (palladium, 10% wt. on activated carbon) was added. The reaction mixture was stirred overnight (18 hours) under hydrogen. Then the solution was filtered, concentrated and purified by flash column chromatography using 10% methanol/90% chloroform, fractions with R$_f$=0.6 collected, concentrated and dried to provide the monodispersed acid 27.

Activation of C$_{18}$(PEG$_8$) Oligomer. Two step activation of monodispersed stearate-PEG8 oligomer 27 was performed as described for stearate-PEG$_6$ in Example 4 above to provide the monodispersed activated C$_{18}$(PEG$_8$) oligomer 28.

Example 6

Synthesis of Activated Triethylene Glycol Monomethyl Oligomers

A solution of toluene containing 20% phosgene (100 ml, approximately 18.7 g, 189 mmol phosgene) was chilled to 0° C. under a N$_2$ atmosphere. Monodispersed mTEG (triethylene glycol, monomethyl ether, 7.8 g, 47.5 mmol) was dissolved in 25 mL anhydrous ethyl acetate and added to the chilled phosgene solution. The mixture was stirred for one hour at 0° C., then allowed to warm to room temperature and stirred for another two and one half hours. The remaining phosgene, ethyl acetate and toluene were removed via vacuum distillation to leave the monodispersed mTEG chloroformate as a clear oily residue.

The monodispersed nTEG chloroformate was dissolved in 50 mL of dry dichloromethane to which was added TEA (triethyleamine, 6.62 mL, 47.5 mmol) and NHS (N-hydroxysuccinimide, 5.8 g, 50.4 mmol). The mixture was stirred at room temperature under a dry atmosphere for twenty hours during which time a large amount of white precipitate appeared. The mixture was filtered to remove this precipitate and concentrated in vacuo. The resultant oil was taken up in dichloromethane and washed twice with cold deionized water, twice with 1N HCl and once with brine. The organics were dried over MgSO$_4$, filtered and concentrated to provide the monodispersed title compound as a clear, light yellow oil. If necessary, the NHS ester could be further purified by flash chromatography on silica gel using EtOAc as the elutant.

Example 7

Synthesis of Activated Palmitat-TEG Oligomers

Monodispersed palmitic anhydride (5 g; 10 mmol) was dissolved in dry THF (20 mL) and stirred at room temperature. To the stirring solution, 3 mol excess of pyridine was added followed by monodispersed triethylene glycol (1.4 mL). The reaction mixture was stirred for 1 hour (progress of the reaction was monitored by TLC; ethyl acetate-chloroform; 3:7). At the end of the reaction, THF was removed and the product was mixed with 10% $H_2SO_4$ acid and extracted ethyl acetate (3×30 mL). The combined extract was washed sequentially with water, brine, dried over $MgSO_4$, and evaporated to give monodispersed palmitate-TEG oligomers.

A solution of N,N'-disuccinimidyl carbonate (3 mmol) in DMF (~10 mL) is added to a solution of the monodispersed palmitate-TEG oligomers (1 mmol) in 10 mL of anydrous DMF while stirring. Sodium hydride (3 mmol) is added slowly to the reaction mixture. The reaction mixture is stirred for several hours (e.g., 5 hours). Diethyl ether is added to precipitate the monodispersed activated title oligomer. This process is repeated 3 times and the product is finally dried.

Example 8

Synthesis of Activated Hexaethylene Glycol Monomethyl Oligomers

Monodispersed activated hexaethylene glycol monomethyl ether was prepared analogously to that of monodispersed triethylene glycol in Example 14 above. A 20% phosgene in toluene solution (35 mL, 6.66 g, 67.4 mmol phosgene) was chilled under a $N_2$ atmosphere in an ice/salt water bath. Monodispersed hexaethylene glycol (1.85 mL, 2.0 g, 6.74 mmol) was dissolved in 5 mL anhydrous EtOAc and added to the phosgene solution via syringe. The reaction mixture was kept stirring in the ice bath for one hour, removed and stirred a further 2.5 hours at room temperature. The phosgene, EtOAc, and toluene were removed by vacuum distillation, leaving monodispersed methyl hexaethylene glycol chloroformate as a clear, oily residue.

The monodispersed chloroformate was dissolved in 20 mL dry dichloromethane and placed under a dry, inert atmosphere. Triethylamine (0.94 mL, 0.68 g, 6.7 mmol) and then NHS (N-hydroxy succinimide, 0.82 g, 7.1 mmol) were added, and the reaction mixture was stirred at room temperature for 18 hours. The mixture was filtered through silica gel to remove the white precipitate and concentrated in vacuo. The residue was taken up in dichloromethane and washed twice with cold water, twice with 1 N HCl and once with brine. The organics were dried over $Na_2SO_4$, filtered and concentrated. Final purification was done via flash chromatography (silica gel, EtOAc) to obtain the activated monodispersed hexaethylene monomethyl ether.

Example 9

Synthesis of Avtivated Heptaethylene Glycol Monomethyl Ether

8-Methoxy-1-(methylsulfonyl)oxy-3,6-dioxaoctane (29). A solution of monodispersed triethylene glycol monomethyl ether molecules (4.00 mL, 4.19 g, 25.5 mmol) and triethylamine (4.26 mL, 3.09 g, 30.6 mmol) in dry dichloromethane (50 mL) was chilled in an ice bath and place under a nitrogen atmosphere. A solution of methanesulfonyl chloride (2.37 mL, 3.51 g, 30.6 mmol) in dry dichloromethane (20 mL) was added dropwise from an addition funnel. Ten minutes after the completion of the chloride addition, the reaction mixture was removed from the ice bath and allowed to come to room temperature. The mixture was stirred for an additional hour, at which time TLC ($CHCl_3$ with 15% MeOH as the elutant) showed no remaining triethylene glycol monomethyl ether.

The reaction mixture was diluted with another 75 mL of dichloromethane and washed successively with saturated $NaHCO_3$, water and brine. The organics were dried over $Na_2SO_4$, filtered and concentrated in vacuo to give a monodispersed mixture of compounds 29 as a clear oil (5.31 g, 86%).

Heptaethylene glycol mono methyl ether (30). To a stirred solution of monodispersed tetraethylene glycol (35.7 mmol) in dry DMF (25.7 mL), under $N_2$ was added in portion a 60% dispersion of NaH in mineral oil, and the mixture was stirred at room temperature for 1 hour. To the resulting sodium salt of the tetraethylene glycol was added a solution of monodispersed mesylate 29 (23.36) in dry DMF (4 ml) in a single portion, and the mixture was stirred at room temperature for 3.5 hours. Progress of the reaction was monitored by TLC (12% $CH_3OH—CHCl_3$). The reaction mixture was diluted with an equal amount of 1N HCl, and extracted with ethyl acetate (2×20 ml) and discarded. Extraction of aqueous solution and work-up gave monodispersed heptaethylene glycol monomethyl ether 30 (82-84% yield). Oil; Rf 0.46 (methanol: chloroform=3:22); MS m/z calc'd for $C_{15}H_{32}O_8$ 340.21 ($M^++1$), found 341.2.

Activation of heptaethylene glycol monomethyl ether. Monodispersed heptaethylene glycol monomethyl ether 30 is activated by a procedure similar to that used in Example 6 above to activate triethylene glycol monomethyl ether to provide the activated heptaethylene glycol monomethyl ether.

Example 10

Synthesis of Activated Decaethylene Glycol Monomethyl Ether (33)

20-methoxy-1-(methylsulfonyl)oxy-3,6,9,12,15,18-hexaoxaeicosane (31). Monodispersed compound 31 was obtained in quantitative yield from compound 30 and methanesulfonyl chloride as described for 29 in Example 9 above, as an oil; Rf 0.4 (ethyl acetate: acetonitrile=1:5); MS m/z calc'd for $C_{17}H_{37}O_{10}$ 433.21 ($M^++1$), found 433.469.

Decaethylene glycol monomethyl ether (32). Monodispersed compound 32 was prepared from compound 31 and monodispersed triethylene glycol using the procedure described above in Example 17. Oil; Rf 0.41 (methanol: chloroform=6:10); MS m/z calc'd for $C_{21}H_{44}O_{11}$ 472.29 ($M^++1$), found 472.29.

Activation of decaethylene glycol monomethyl ether. Monodispersed decaethylene glycol monomethyl ether 32 is activated by a procedure similar to that used in Example 6 above to activate triethylene glycol monomethyl ether to provide the activated decaethylene glycol monomethyl ether 33.

Example 11

Preparation of $Lys^{B29}$-Oligomer-Conjugated Insulin

Figure 11:
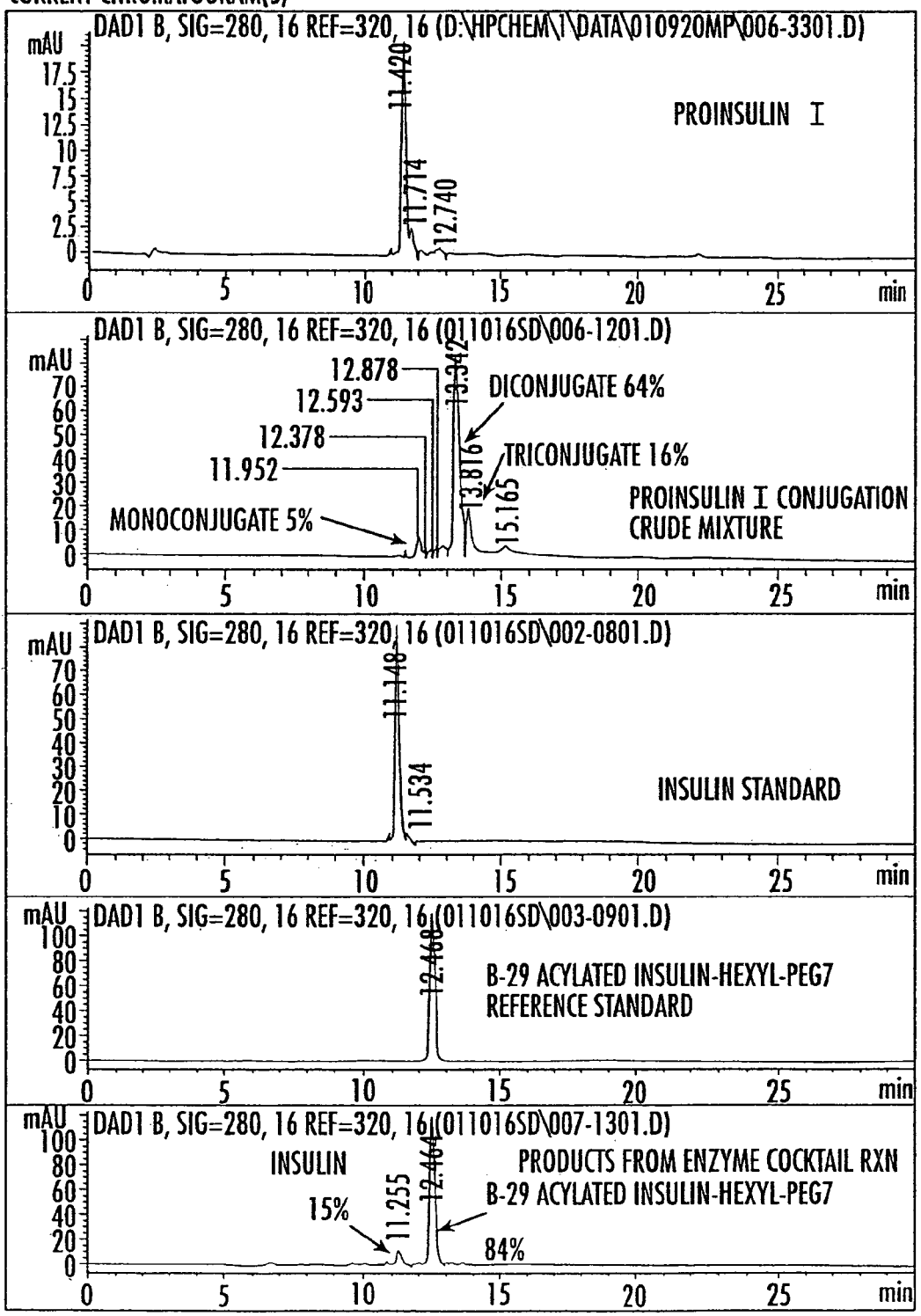
FIG. 11 illustrates an HPLC profile of production of B-29 acylated Insulin-hexyl-PEG7 via proinsulin I.

Conjugation of Recombinant Proinsulin I. Recombinant Proinsulin I (MW 10,642 Daltons) was obtained from Biobras, of Belo Horizonte, Brazil. A $2.32 \times 10^{-3}$ mmol portion of proinsulin I was dissolved in 10 mL of DMSO. To the solution was added 324 μL of triethylamine. The resulting solution was allowed to stir for 5 minutes, and then a solution of activated methylheptaethylene glycol ((PEG7)-hexyl oligomer) ($9.30 \times 10^{-3}$ mmol) in acetonitrile was added. The course of the conjugation (acylation) reaction was monitored by HPLC. When reaction appeared to be complete, it was quenched by addition of 3.54 mL of 5% aqueous trifluoroacetic acid solution. The reaction mixture was then processed and exchanged into 100 mM Tris-HCl Buffer, pH 7.6. The HPLC profile of the product mixture, oligomer-conjugated recombinant Proinsulin I, is shown in FIG. 11.

Figure 12:
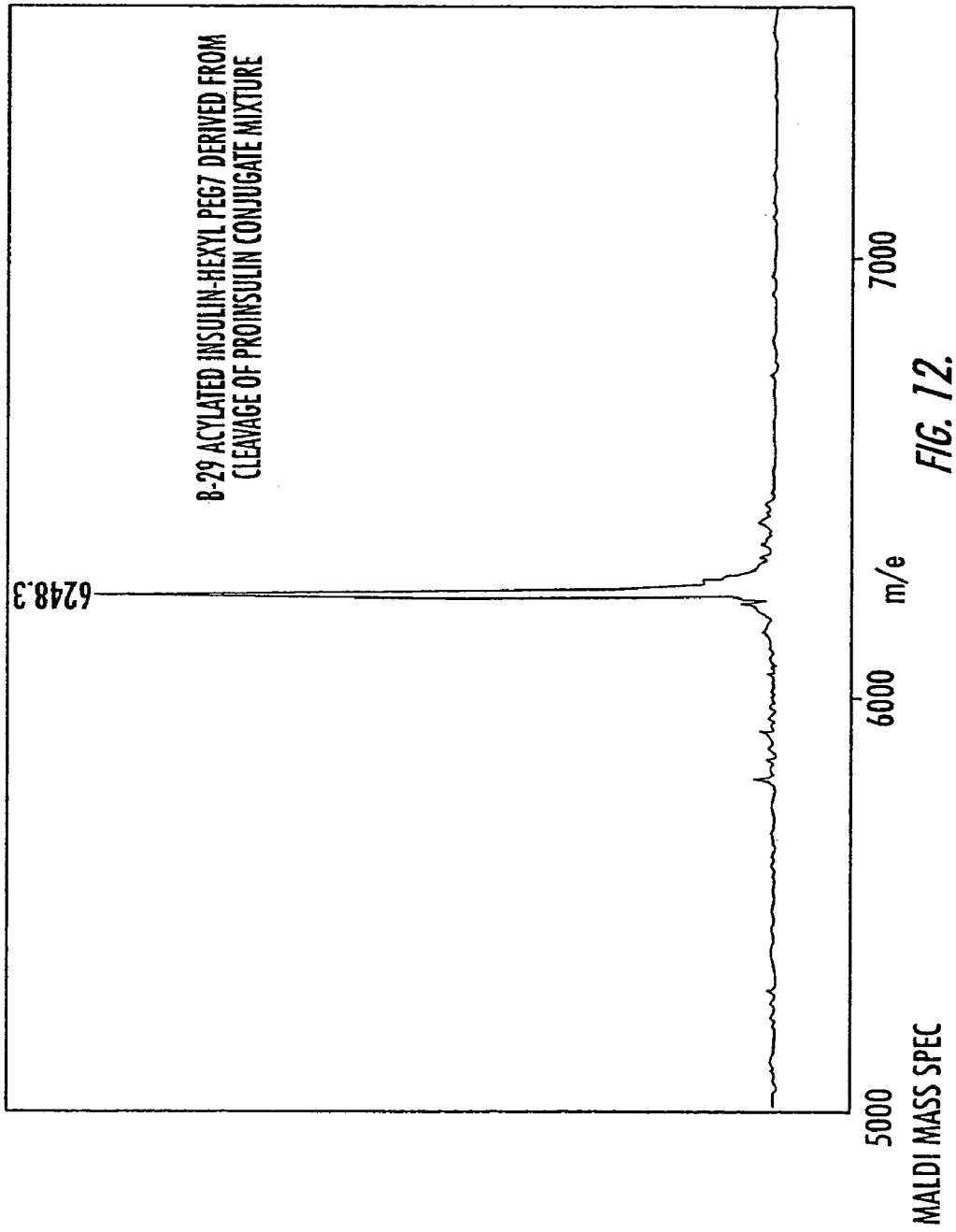
FIG. 12 illustrates an m.s. spectrum of B-29 acylated Insulin-hexyl-PEG7 via proinsulin I.
Figure 13:
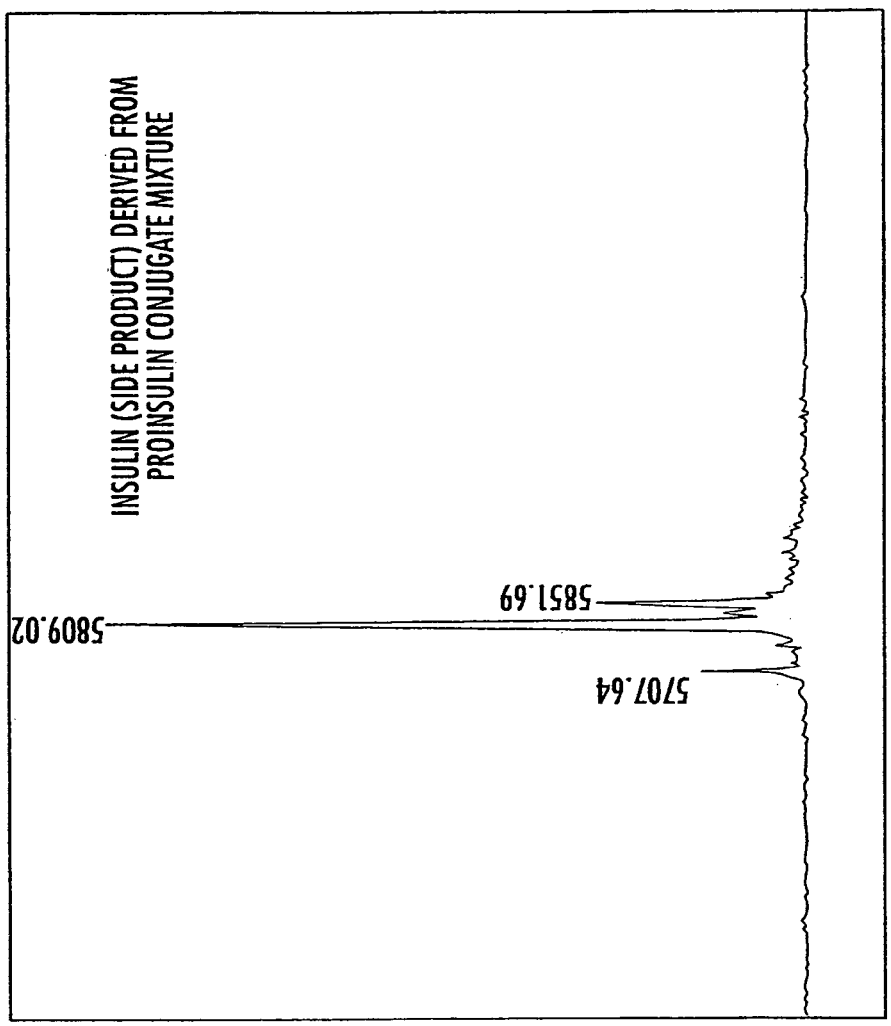
FIG. 13 illustrates an m.s. spectrum of insulin (side product) derived from proinsulin I conjugate mixture.

(b) Enzyme Cocktail Cleavage of Oligomer-Conjugated Recombinant Proinsulin I. An aliquot of the Tris-HCl solution of the product mixture from Example 1(a) was analyzed by HPLC to determine the polypeptide concentration. A solution of trypsin (TPCK treated; from bovine pancreas) was prepared in 100 mM Tris-HCl Buffer, pH 7.6. A solution of carboxypeptidase B (from porcine pancreas) was prepared in 100 mM Tris-HCl Buffer, pH 7.6. The product mixture from Example 11(a) (0.424 μmol/mL) was then allowed to react with trypsin ($5.97 \times 10^{-4}$ μmol/mL) and carboxypeptidase B ($1.93 \times 10^{-4}$ μmol/L). After 30 minutes, the reaction was quenched by the addition of 1.58 mL of 1% trifluoroacetic acid in acetonitrile. The major products were identified by HPLC retention time (relative to the retention times of known reference standards) and mass spectral analysis. Insulin (10%) and $Lys^{B29}$-Hexyl-PEG7-Oligomer-Conjugated Insulin (84%) were thus obtained (FIGS. 11-13).

Example 12

Isolation of the Products of Oligomer-Conjugation of Recombinant Proinsulin I

Reversed-phase HPLC was used to isolate the major products from the product mixture obtained from the conjugation reaction described in Example 11(a). An HPLC column (1.0 cm. i.d.×25 cm. length) was packed with a commercially available C18 stationary phase known to be useful for the separation of peptides and proteins, and then was incorporated into an HPLC system. The system was equilibrated with elution buffer, a mixture comprising 72% mobile phase A ($H_2O$ with 0.1% trifluoroacetic acid) and 28% mobile phase B (acetonitrile with 0.1% trifluoroacetic acid) that was delivered at a flow rate of 5 mL/min. A solution of the product mixture in 100 mM Tris-HCl Buffer, pH 7.6, was applied to the reversed-phase column, and the products were separated and eluted using a gradient in which the acetonitrile component of the elution buffer (mobile phase B) was increased as follows:

28%-30% mobile phase B over 60 minutes, then
30%-32% mobile phase B over 30 minutes, then
32%-36% mobile phase B over 40 minutes.

Figure 14:
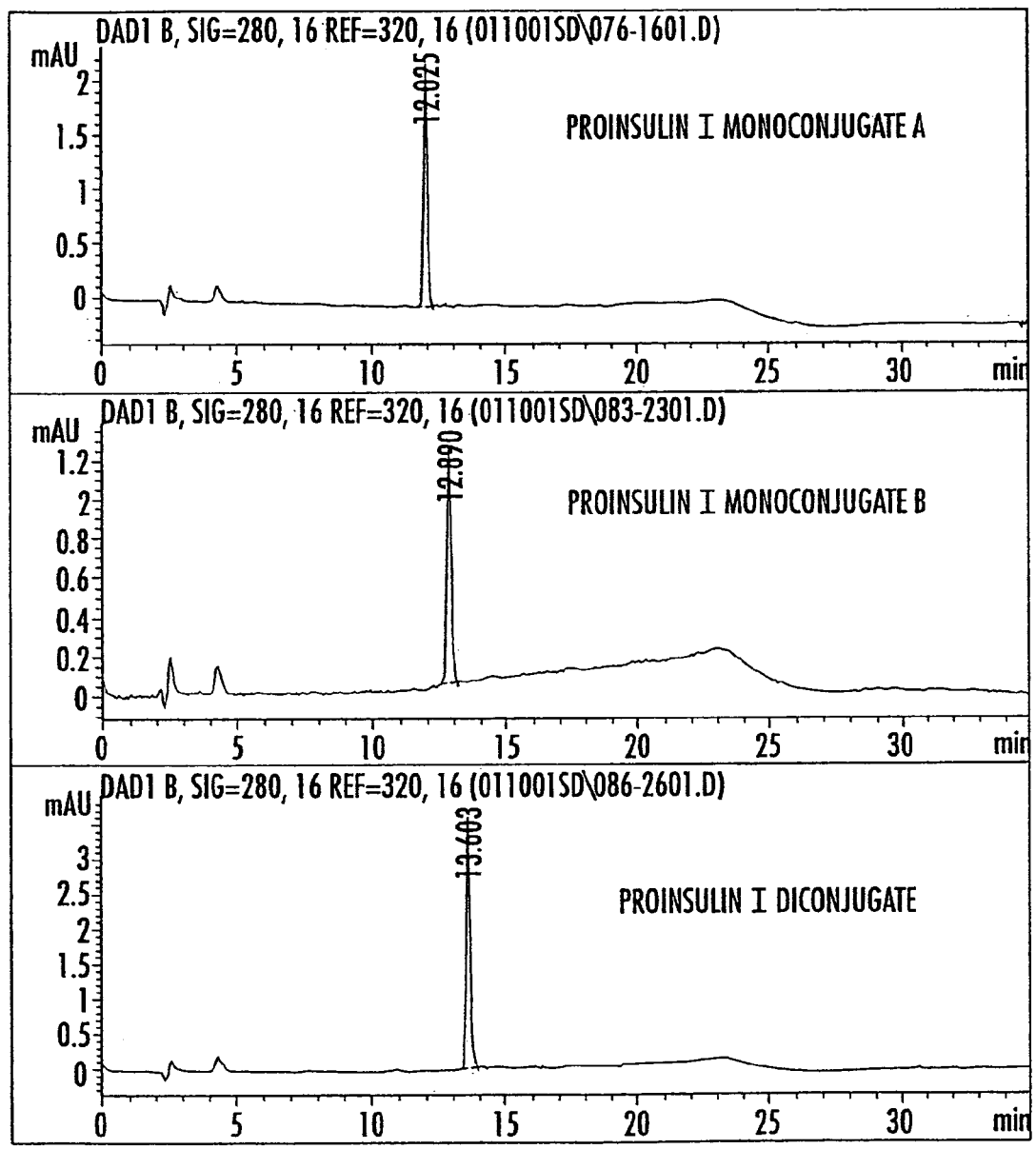
FIG. 14 illustrates an HPLC profile of proinsulin I monoconjugate A, proinsulin I monocojugate B and proinsulin I diconjugate.
Figure 15:
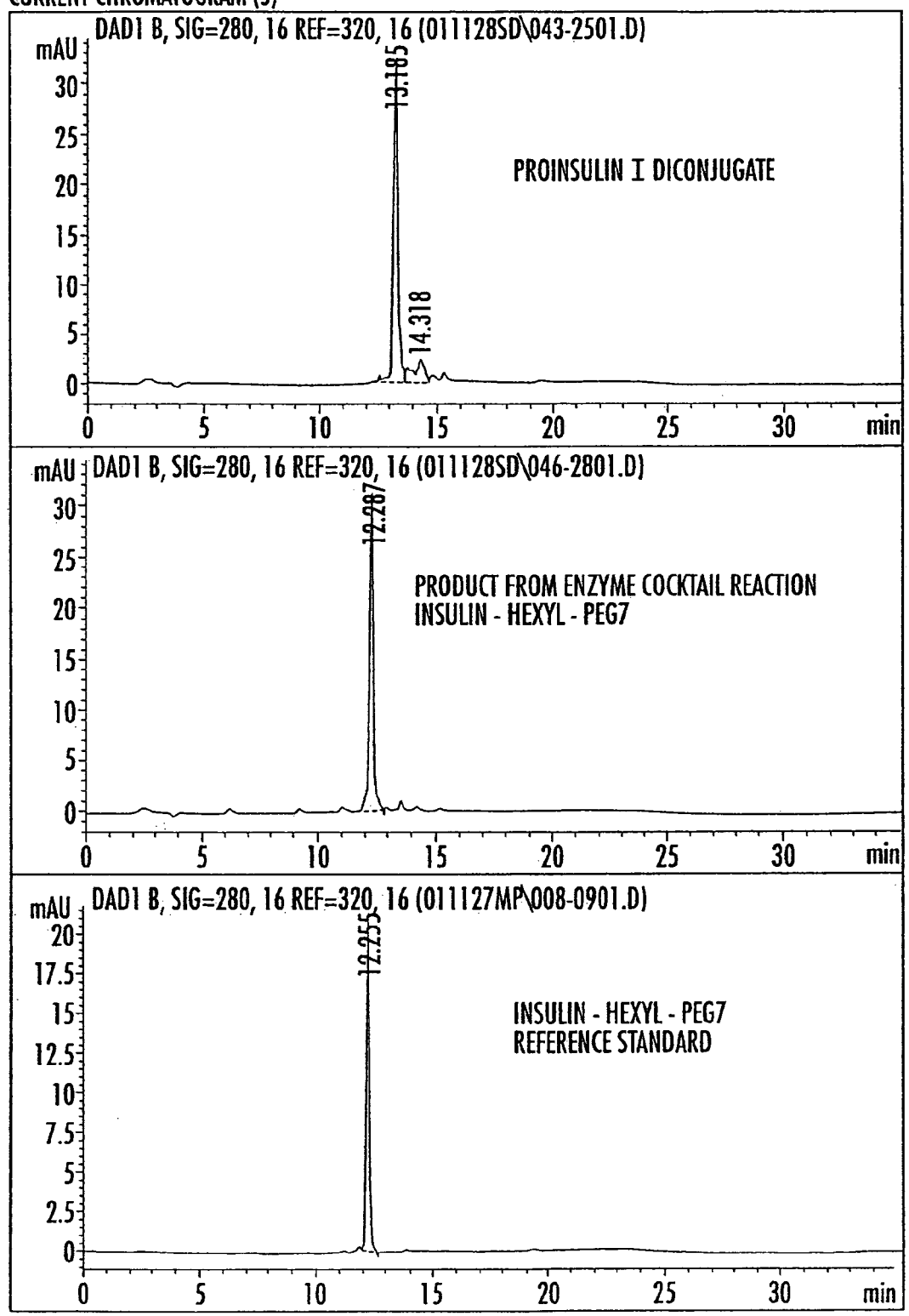
FIG. 15 illustrates an HPLC profile of production of Insulin-hexyl-PEG7 monoconjugate from reaction of proinsulin I diconjugate with enzyme cocktail of carboxy peptidase B and trypsin.
Figure 16:
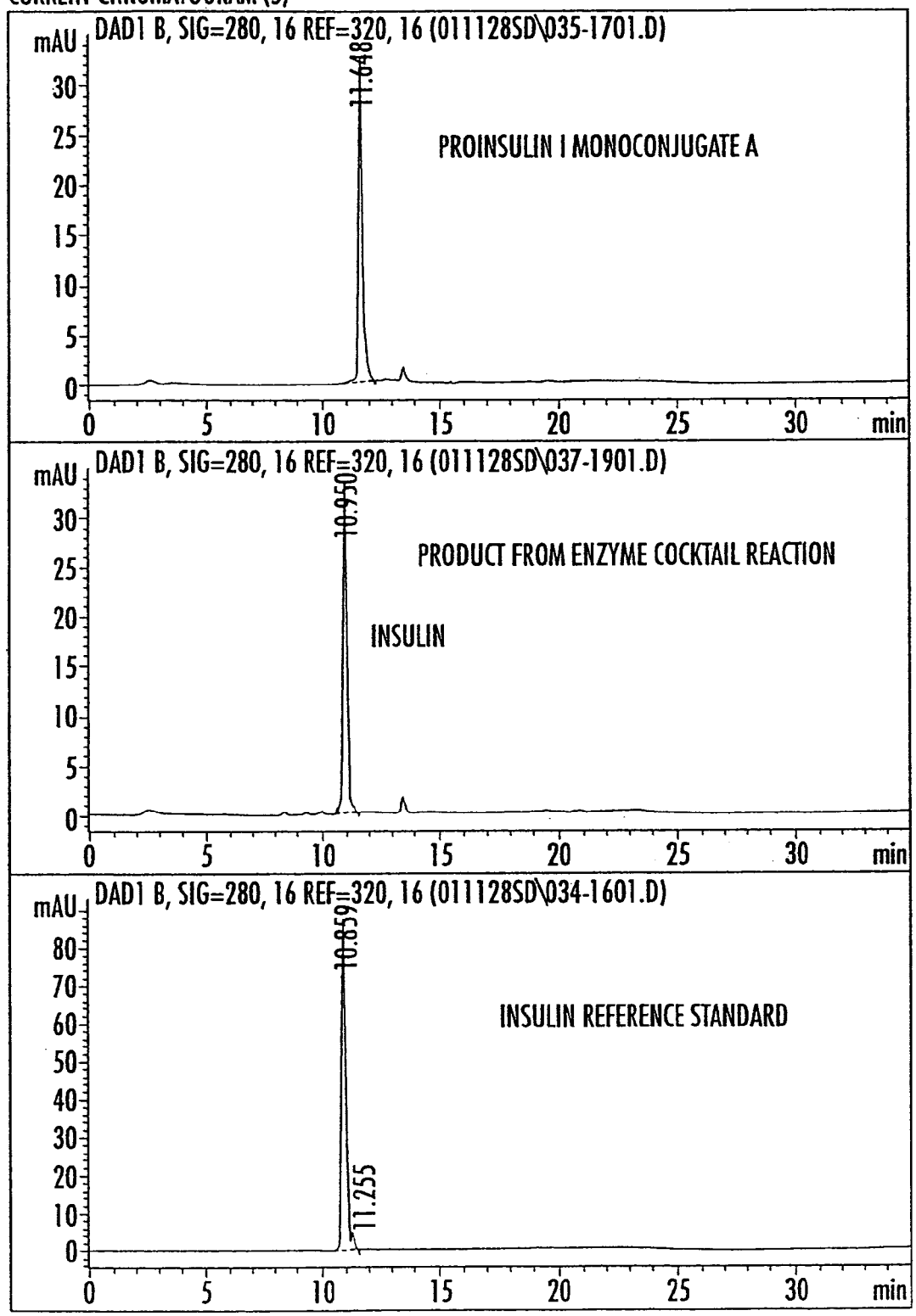
FIG. 16 illustrates an HPLC profile of production of insulin (side product) from reaction of proinsulin I monoconjugate A with enzyme cocktail of carboxy peptidase B and trypsin.

Fractions were collected and individually analyzed by HPLC to determine the identity and purity of the product contained therein. Common fractions containing one of the four products (monoconjugate-A ("Proinsulin I Monoconjugate-A"), monoconjugate-B ("Proinsulin I Monoconjugate-B"), diconjugate ("Proinsulin I Diconjugate") and triconjugate ("Proinsulin I Triconjugate") were then pooled, and the solvent was removed by rotary evaporation. HPLC (FIG. 14) and mass spectral analysis were used to determine the identity and purity of each isolate.

Example 13

Enzyme Cocktail Cleavage of Isolated Conjugates of Recombinant Proinsulin (I)

Each conjugate (Proinsulin I Mono A, Mono B, Di, or Tri) that was isolated using the procedure described in Example 12 was dissolved in 100 mM Tris-HCl Buffer, pH 7.6, and analytical HPLC was used to determine the polypeptide concentration of the resulting solution. A solution of trypsin (TPCK treated; from bovine pancreas) was prepared in 100 mM Tris-HCl Buffer, pH 7.6. A solution of carboxypeptidase B (from porcine pancreas) was prepared in 100 mM Tris-HCl Buffer, pH 7.6. The crude mixture (1 mmol) was then allowed to react with trypsin ($1.39 \times 10^{-3}$ mmol) and carboxypeptidase B ($4.56 \times 10^{-4}$ mmol). After 30 minutes, the reaction was quenched by addition of 1% trifluoroacetic acid in acetonitrile. The product mixture from each reaction was processed and analyzed by HPLC. The HPLC retention time relative to that of reference standards and mass spectral analysis were used to determine the identity and purity of each product (Table 1).

TABLE 1

Oligomer-conjugates of Proinsulin I and Products (or Expected Products) from Enzyme Cocktail Cleavage of Each

| Conjugate | Product (Expected Products) | FIG. |
|---|---|---|
| Proinsulin I Mono A | Insulin | 16 |
| Proinsulin I Mono B | (Lys-hexyl-PEG7-oligomer-conjugated leader peptide) | — |
| Proinsulin I Di | $Lys^{B29}$-Hexyl-PEG7-Oligomer-Conjugated Insulin | 15 |
| Proinsulin I Tri | ($Lys^{B29}$-Hexyl-PEG7-Oligomer-Conjugated Insulin and Lys-hexyl-PEG7-oligomer-conjugated C-peptide) | — |

Example 14

Trypsin Cleavage of Isolated Conjugates of Proinsulin I

Each conjugate (Proinsulin I Mono A, Mono B, Di, or Tri) that was isolated using the procedure described in Example 12 is dissolved in 100 mM Tris-HCl Buffer, pH 7.6, and the resulting solution is analyzed by HPLC to determine the polypeptide concentration. A solution of trypsin (TPCK treated; from bovine pancreas) is prepared in 100 mM Tris-HCl Buffer, pH 7.6. Each conjugate (300 mmol) is then allowed to react with trypsin (1 mmol). After 20 minutes, the reaction is quenched by addition of 1% trifluoroacetic acid in acetonitrile. The products of the reaction are isolated and analyzed by HPLC retention time and mass spectral analysis to determine identity. The expected products are Insulin ($Arg^{31}$) or $Lys^{B29}$-hexyl-PEG7-oligomer-conjugated Insulin ($Arg^{31}$) illustrated in Table 2.

TABLE 2

| Conjugate | Expected Products |
|---|---|
| Proinsulin I Mono A | Insulin($Arg^{31}$) and Lys-hexyl-PEG7-oligomer conjugated C-peptide |
| Proinsulin I Mono B | $Lys^{B29}$-hexyl-PEG7-oligomer-conjugated insulin($Arg^{31}$) and C-peptide |

TABLE 2-continued

| Conjugate | Expected Products |
| --- | --- |
| Proinsulin I Di | Lys$^{B29}$-hexyl-PEG7-oligomer-conjugated insulin(Arg$^{31}$) and Lys-hexyl-PEG7-oligomer conjugated C-peptide |
| Proinsulin I Tri | Lys$^{B29}$-hexyl-PEG7-oligomer-conjugated insulin(Arg$^{31}$) and Lys-hexyl-PEG7-oligomer-conjugated C-peptide and Lys-hexyl-PEG7-oligomer conjugated leader peptide |

Example 15

Carboxypeptidase B Cleavage of Trypsin Cleavage Product Mixture

An aliquot of the reaction mixture containing Lys$^{B29}$-hexyl-PEG7-oligomer-conjugated Insulin(Arg$^{31}$) (300 mmol) (from Example 14) in 100 mM Tris-HCl buffer, pH 7.6, is removed. A solution of carboxypeptidase B (from porcine pancreas) is prepared in 100 mM Tris-HCl buffer, pH 7.6. Carboxypeptidase B (1 mmol) is added to the reaction mixture. The reaction is allowed to continue for 15 hours, and then is quenched with addition of 1% trifluoroacetic acid in acetonitrile. The expected products of each reaction are illustrated in Table 3.

TABLE 3

| Conjugate | Expected Products |
| --- | --- |
| Proinsulin I Mono A | Insulin and Lys-hexyl-PEG7-oligomer conjugated C-peptide |
| Proinsulin I Mono B | Lys$^{B29}$-hexyl-PEG7-oligomer-conjugated insulin and C-peptide |
| Proinsulin I Di | Lys$^{B29}$-hexyl-PEG7-oligomer-conjugated insulin and Lys-hexyl-PEG7-oligomer conjugated C-peptide |
| Proinsulin I Tri | Lys$^{B29}$-hexyl-PEG7-oligomer-conjugated insulin and Lys-hexyl-PEG7-oligomer-conjugated C-peptide and Lys-hexyl-PEG7-oligomer conjugated leader peptide |

Example 16

Figure 2:
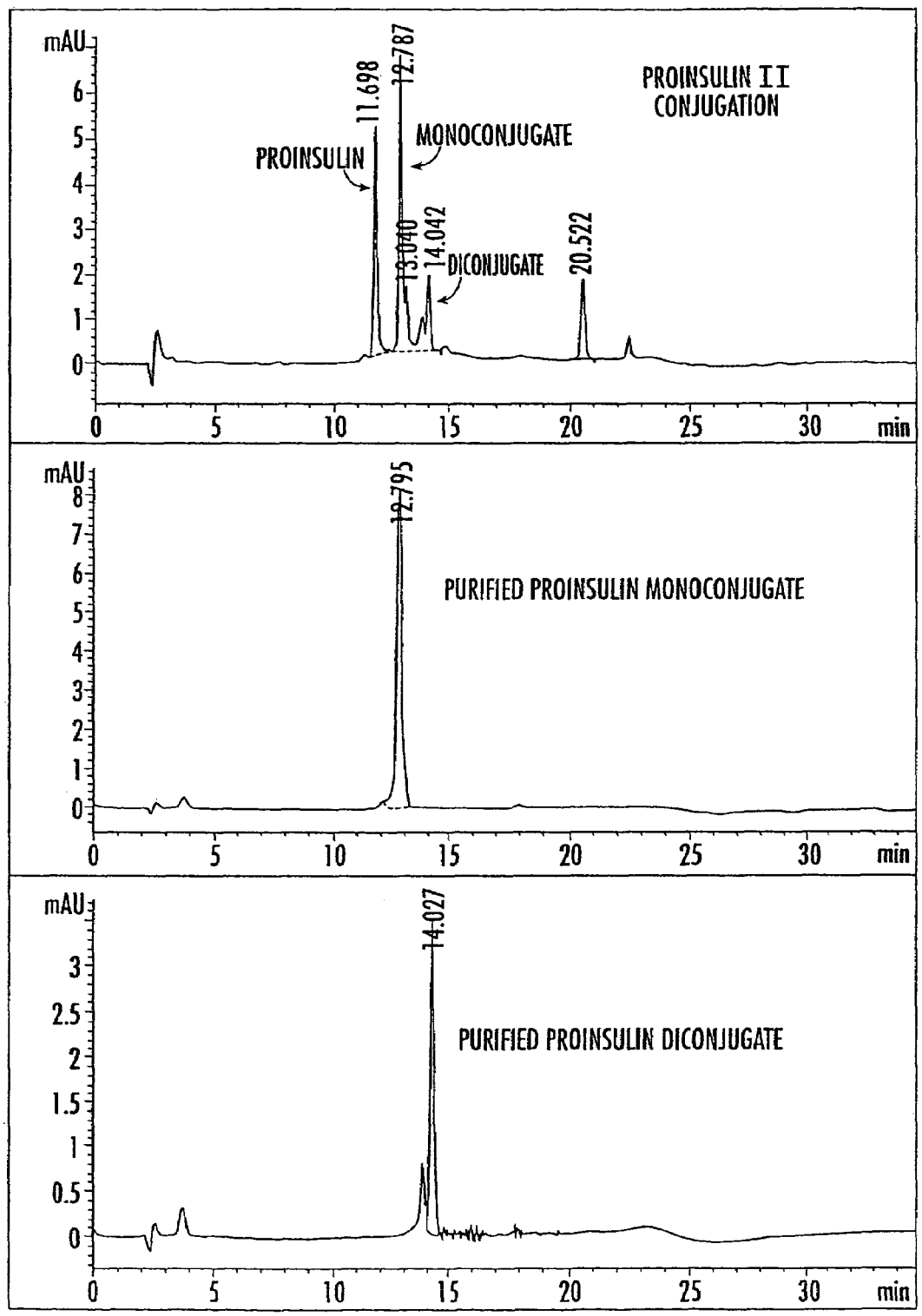
FIG. 2 illustrates an HPLC profile of proinsulin II conjugation.

Preparation of Lys$^{B29}$-Oligomer Conjugated Insulin (a) Conjugation of Recombinant Proinsulin II. Recombinant Proinsulin II (MW 11,133 Daltons) was obtained from Itoham Foods, Inc. of Ibaraki Pref, Japan. The Recombinant Proinsulin II had a leader peptide and a C-peptide that were each devoid of Lysine residues. A 2.55×10$^{-3}$ mmol portion of recombinant Proinsulin II was dissolved in 10 mL of DMSO. To the solution was added 355 µL of triethylamine. The resulting solution was allowed to stir for 5 minutes, and then a solution of activated methylpolyethylene glycol ((PEGn)-hexyl oligomer) (n=7±3 or n=7) (5.10×10$^{-3}$ mmol) in acetonitrile was added. The course of the reaction was monitored by HPLC. After the reaction appeared to be complete, it was quenched by addition of 3.7 mL of 5% aqueous trifluoroacetic acid solution. The reaction mixture was then processed and exchanged into 100 mM Tris-HCl Buffer, pH 7.6. The HPLC profile of the oligomer-conjugated recombinant Proinsulin II product mixture is shown in FIG. 2.

Figure 9:
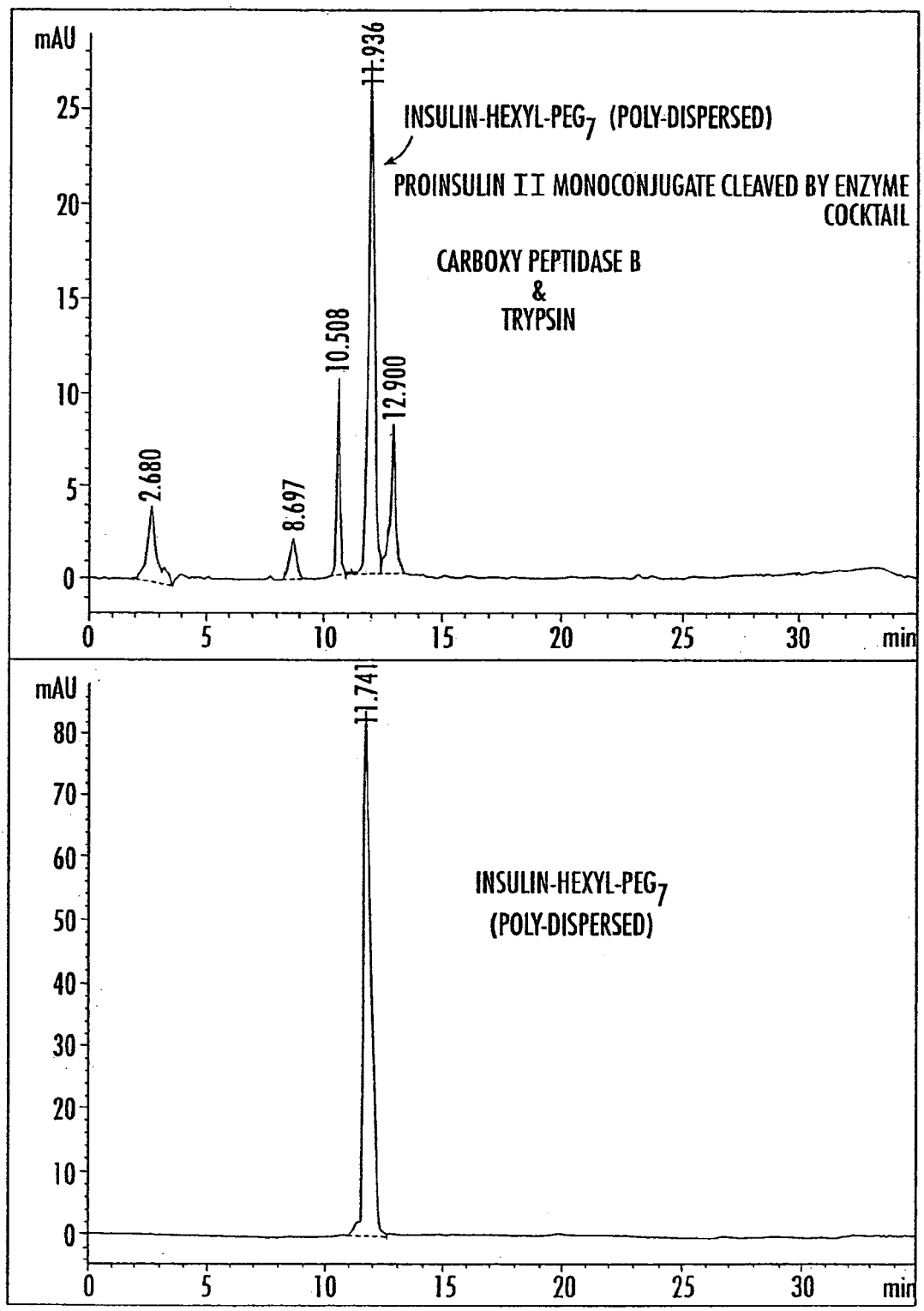
FIG. 9 illustrates an HPLC profile of the production of Insulin-hexyl-PEG7 (polydispersed) from Proinsulin II monoconjugate cleaved by an enxyme cocktail of carboxy peptidase B and trypsin.
Figure 10:
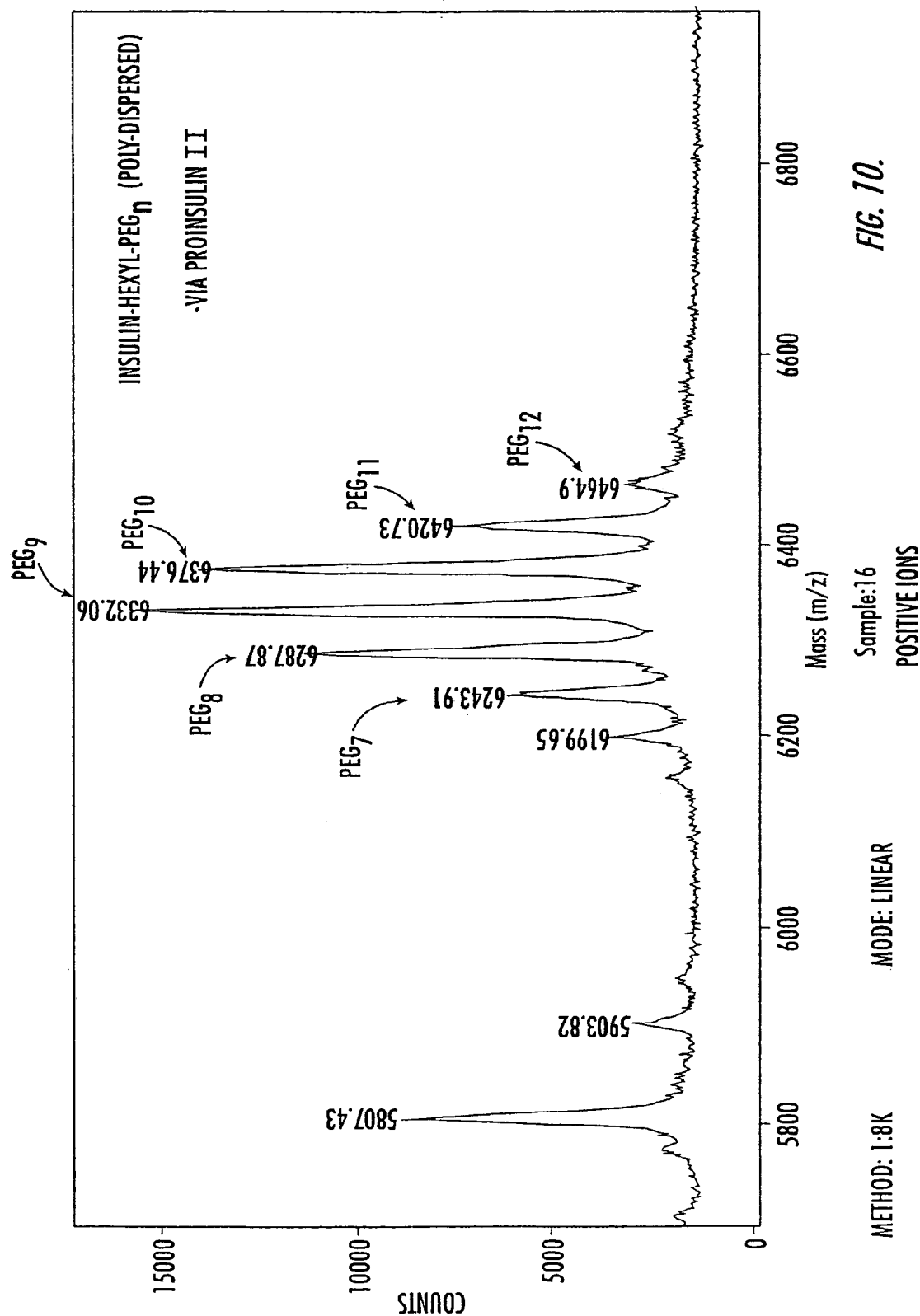
FIG. 10 illustrates an m.s. spectrum of Insulin-hexyl-PEGn (polydispersed) via proinsulin II.

(b) Enzyme Cocktail Cleavage of Oligomer-Conjugated Recombinant Proinsulin II. The Tris-HCl solution of the product mixture from Example 16(a) was analyzed by HPLC to determine the polypeptide concentration therein. A solution of trypsin (TPCK treated; from bovine pancreas) was prepared in 100 mM Tris-HCl Buffer, pH 7.6. A solution of carboxypeptidase B (from porcine pancreas) was prepared in 100 mM Tris-HCl Buffer, pH 7.6. The product mixture (0.399 µmol/mL) was allowed to react with trypsin (5.57×10$^{-4}$ µmol/mL) and carboxypeptidase B (1.82×10$^{-4}$ µmol/mL). After 30 minutes, the reaction was quenched by addition of 550 µL of 1% trifluoroacetic acid in acetonitrile. The major products were identified by HPLC retention time (relative to that of known reference standards) and mass spectral analysis. Insulin (23%) and Lys$^{B29}$-hexyl-PEGn-oligomer-conjugated Insulin (60%) and other (17%) were thus obtained (FIGS. 9-10).

Example 17

Isolation of the Products of Oligomer-Conjugation of Recombinant Proinsulin II

Figure 3:
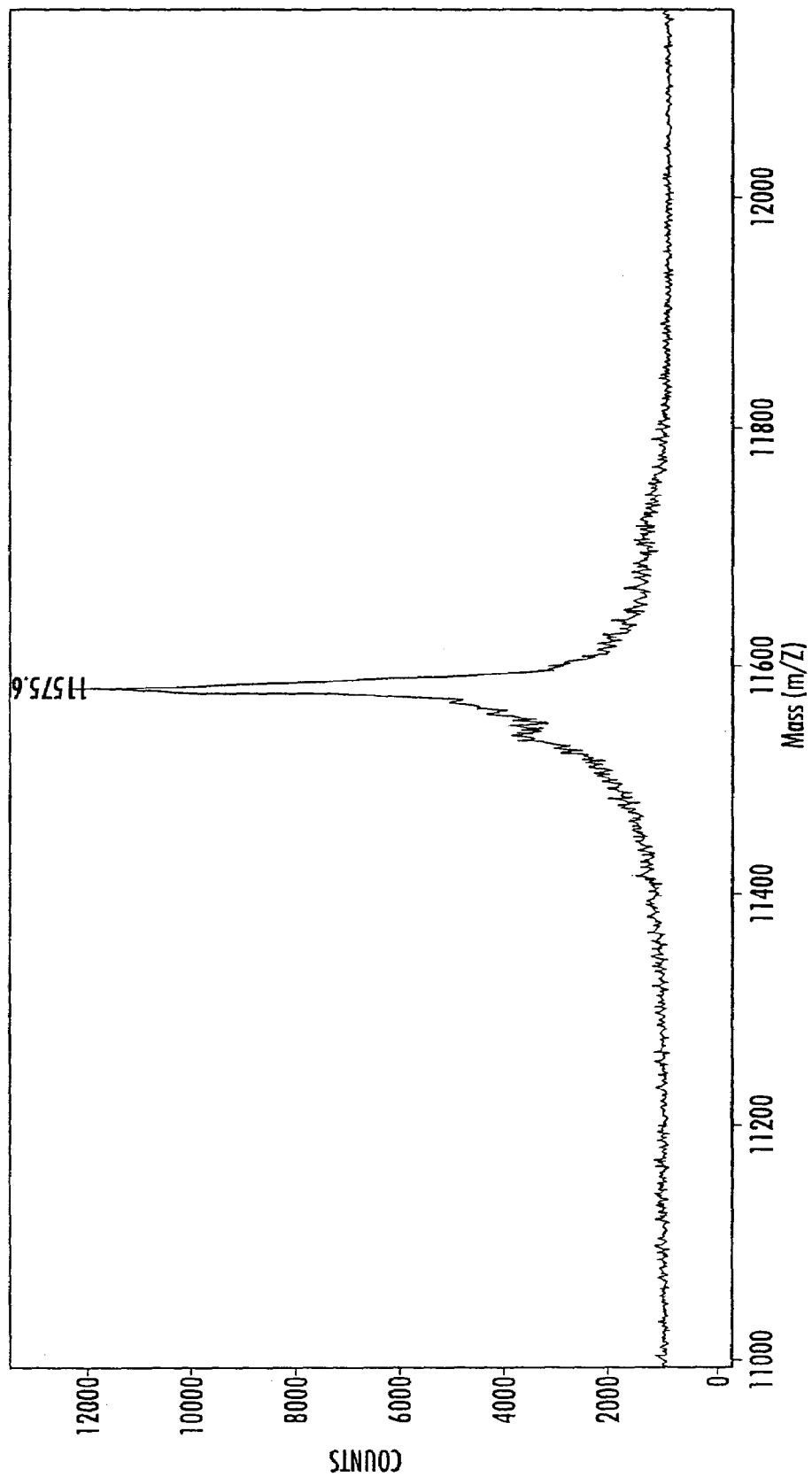
FIG. 3 illustrates an m.s. spectrum of purified proinsulin II monoconjugate.
Figure 4:
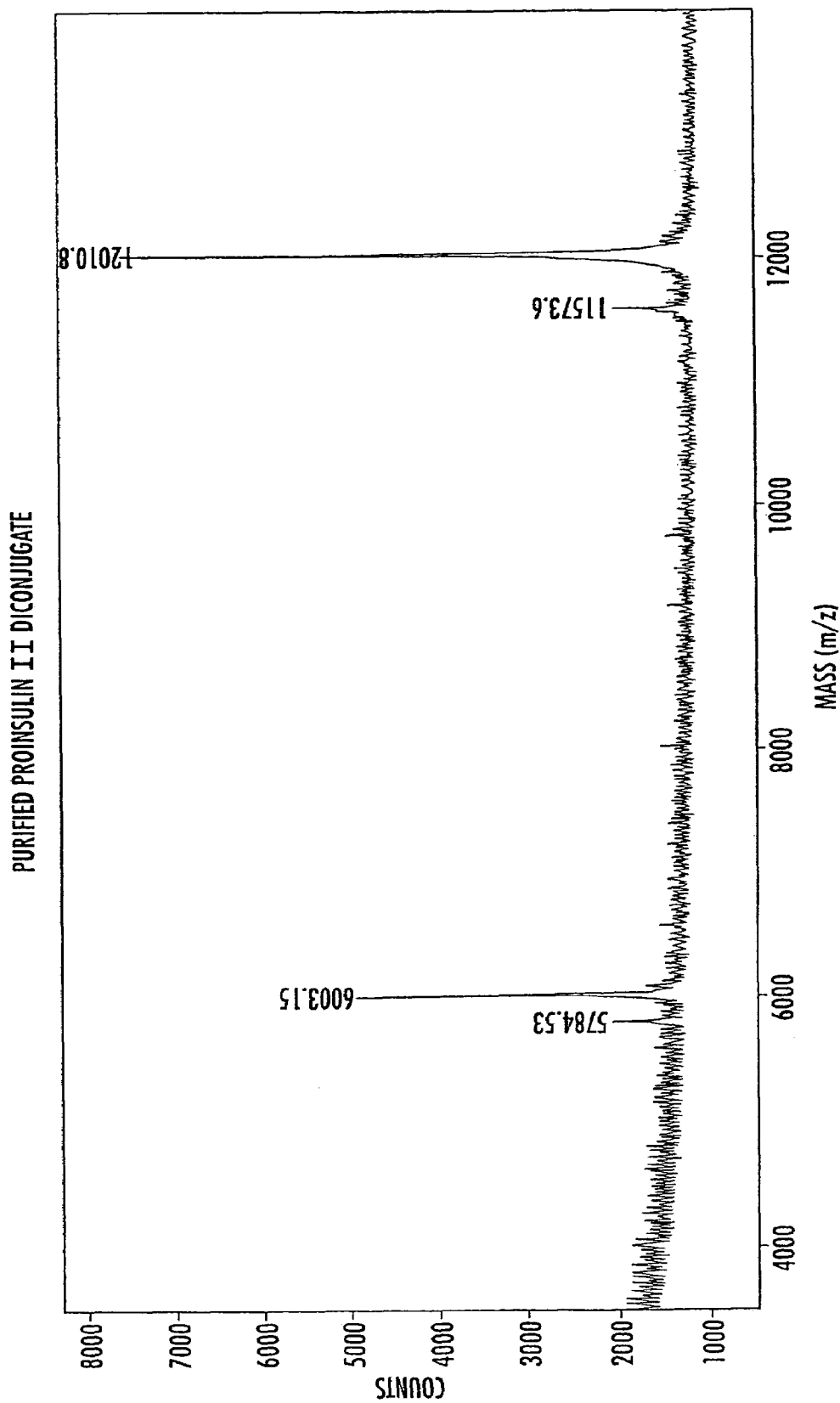
FIG. 4 illustrates an m.s. spectrum of purified proinsulin II diconjugate.

Each major product from the conjugation reaction described in Example 16(a) was isolated using reversed-phase HPLC. A column (1.0 cm. i.d.×25 cm. length) was packed with a commercially available C18 stationary phase known to be useful for the resolution of polypeptides and proteins, and then was incorporated into an HPLC system. The system was equilibrated with elution buffer that was a mixture of 75% mobile phase A (H$_2$O with 0.1% trifluoroacetic acid) and 25% mobile phase B (acetonitrile with 0.1% trifluoroacetic acid) that was delivered at a flow rate of 5 mL/min. The Tris-HCl solution of the product mixture from Example 16(a) was applied to the column, and the major products were separated and eluted using a gradient elution in which the composition of the elution buffer was changed from 25% mobile phase B to 35% mobile phase B over 120 minutes. Each of the fractions that were collected was analyzed by HPLC to determine the identity and purity of the product contained therein. Common fractions of each product (Proinsulin II monoconjugate ("Proinsulin II Mono") and diconjugate ("Proinsulin II Di") were then pooled, and the solvent was removed by rotary evaporation. The identity and purity of each product were determined by HPLC and mass spectrometric analyses (FIGS. 2-4).

Example 18

Enzyme Cocktail Cleavage of Isolated Conjugates of Recombinant Proinsulin II

Each Proinsulin II conjugate (Proinsulin II Mono, Di or Tri) that was isolated using the procedure described in Example 17 was dissolved in 100 mM Tris-HCl Buffer, pH 7.6, and an aliquot of the solution was analyzed by HPLC to determine the polypeptide concentration therein. A solution of trypsin (TPCK treated; from bovine pancreas) was prepared in 100 mM Tris-HCl Buffer, pH 7.6. A solution of carboxypeptidase B (from porcine pancreas) was prepared in 100 mM Tris-HCl Buffer, pH 7.6. The conjugate (0.127 µmol/mL) was allowed to react with trypsin (1.77×10$^{-4}$ µmol/mL) and carboxypeptidase B (5.77×10$^{-5}$ µmol/mL). After 30 minutes, the reaction was quenched by addition of 250 µL of 1% trifluoroacetic acid in acetonitrile. Isolation of the major products followed by identification by HPLC retention time against reference standards and mass spectral analysis showed that Insulin or B-29 acylated Insulin-hexyl-PEG7 were produced in the reaction. The products and yields of each reaction are illustrated in Table 4.

TABLE 4

| Conjugate | Expected Products | Yield |
|---|---|---|
| Proinsulin II Mono | Insulin | 15% |
| | $Lys^{B29}$-hexyl-PEGn-oligomer conjugated insulin | 85% |
| Proinsulin II Di | $Lys^{B29}$-hexyl-PEGn-oligomer-conjugated insulin | 92% |

Example 19

Trypsin Cleavage of Isolated Conjugates of Proinsulin II

Each conjugate (Proinsulin II Mono, Di or Tri) from Example 17 was dissolved in 100 mM Tris-HCl Buffer, pH 7.6, and the resulting solution was analyzed by HPLC to determine the polypeptide concentration therein. A solution of trypsin (TPCK treated; from bovine pancreas) was prepared in 100 mM Tris-HCl Buffer, pH 7.6. Each conjugate (0.127 μmol/mL) was then allowed to react with trypsin (4.23×10$^{-4}$ μmol/mL). After 20 minutes, reaction was quenched by addition of 250 μL of 1% trifluoroacetic acid in acetonitrile. Isolation of the major products followed by identification by HPLC retention time and mass spectral analysis showed that Insulin($Arg^{31}$) or $Lys^{B29}$-hexyl-PEGn-oligomer-conjugated Insulin($Arg^{31}$) was produced in the reaction. The products and yields of each reaction are illustrated in Table 5.

Example 20

Carboxypeptidase B Cleavage of Trypsin Cleavage Mixture

Figure 5:
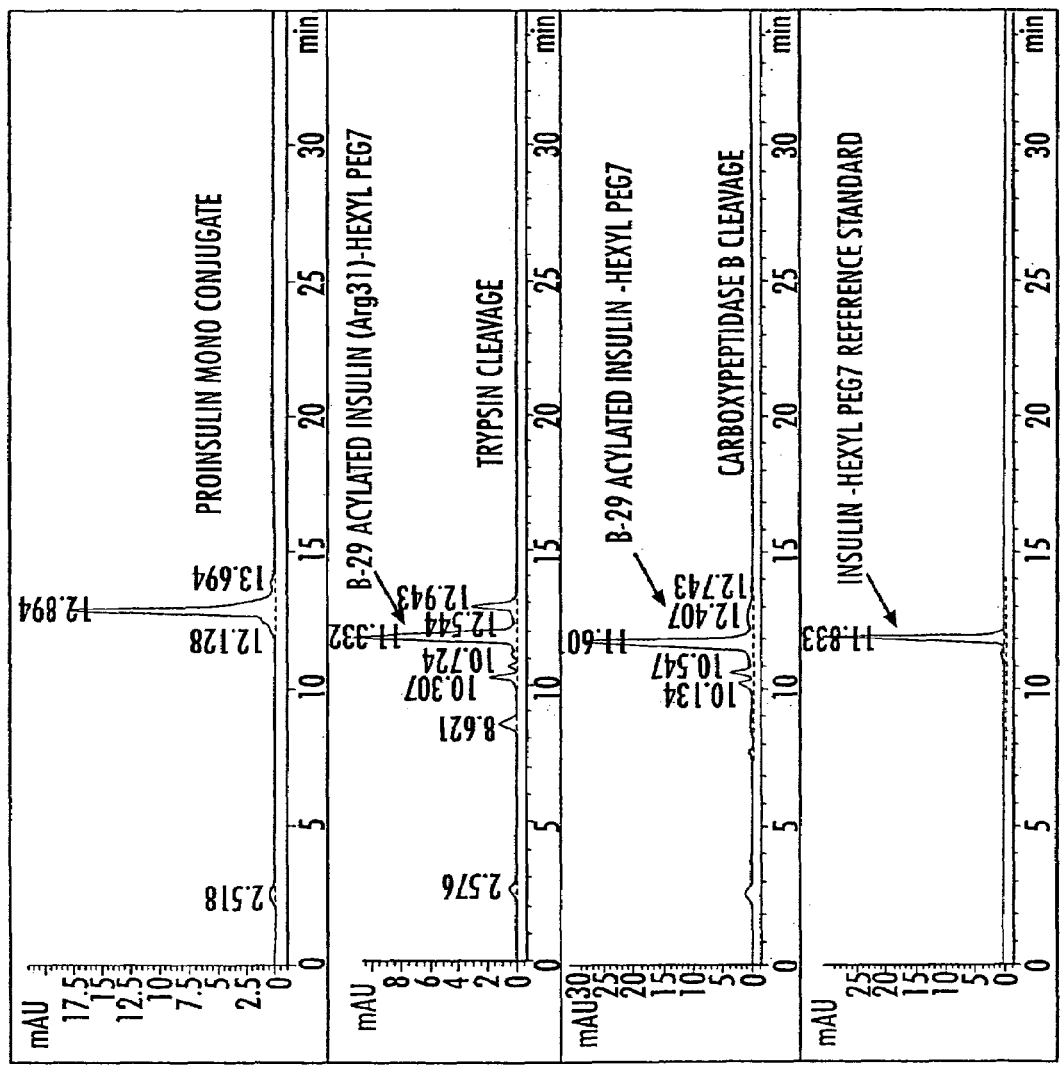
FIG. 5 illustrates an HPLC profile of production of Insulin-hexyl-PEG7 monoconjugate.
Figure 6:
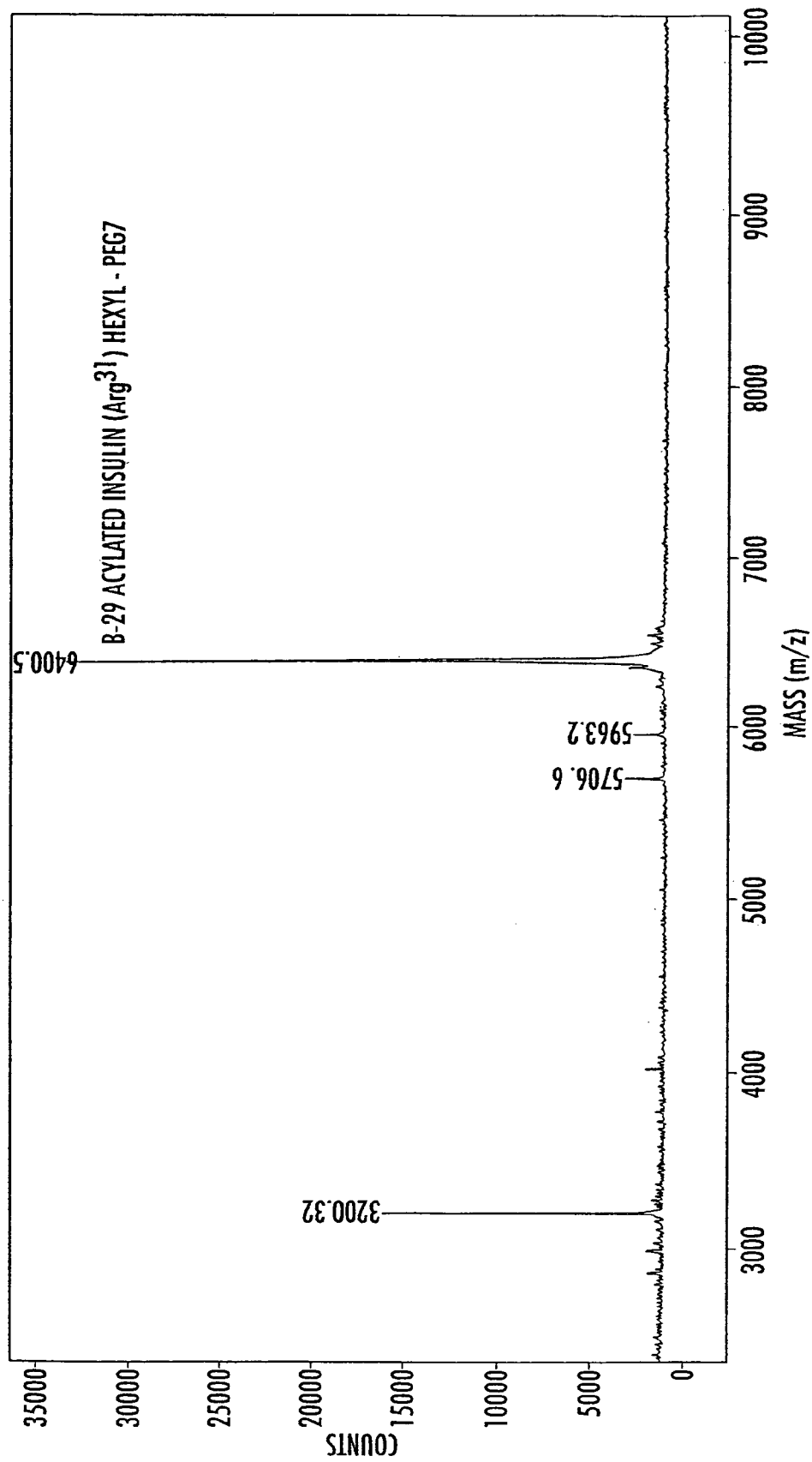
FIG. 6 illustrates an m.s. spectrum of the product of trypsin cleavage of a proinsulin II monoconjugate.
Figure 7:
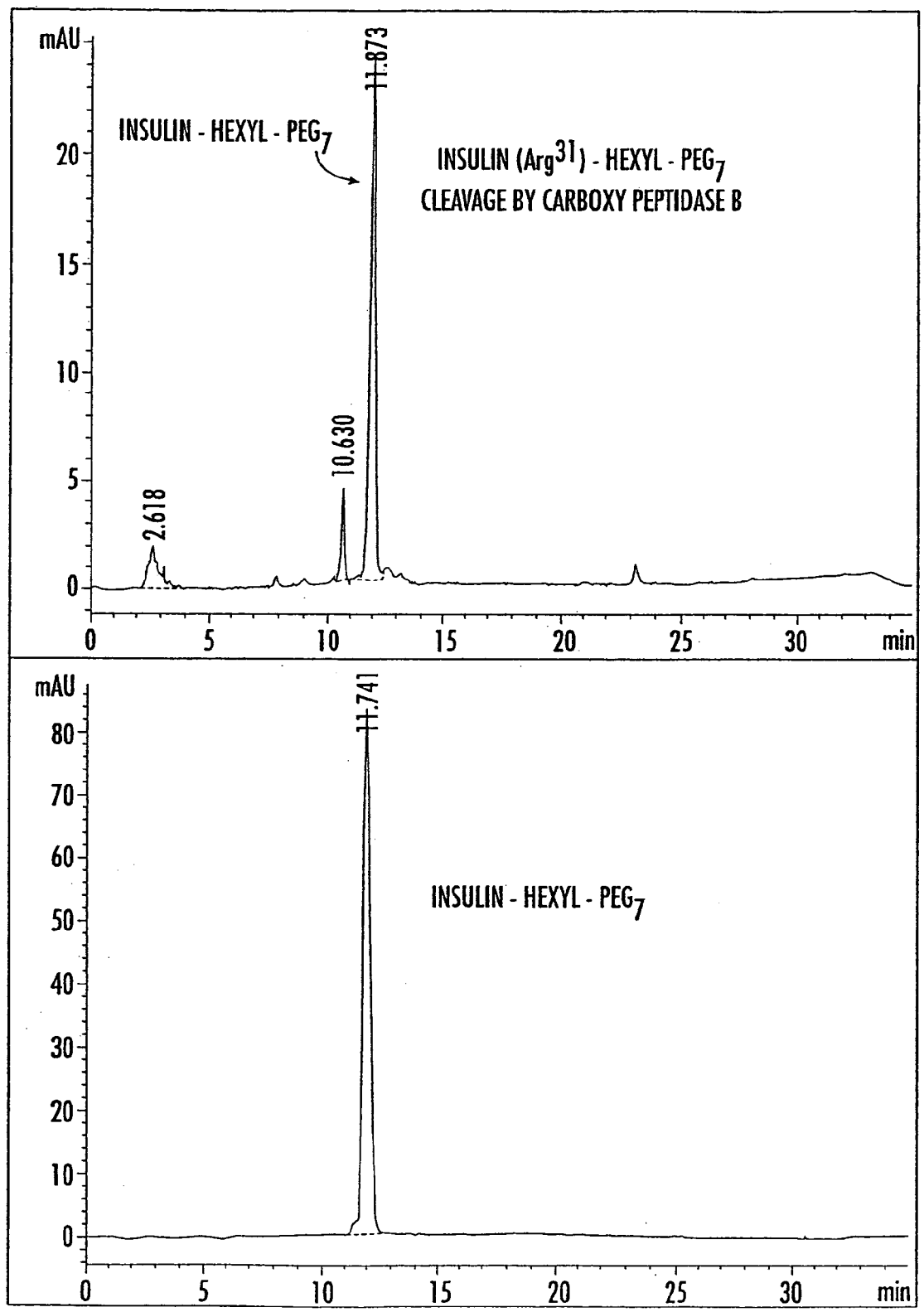
FIG. 7 illustrates an HPLC profile of Insulin(Arg$^{31}$)-hexyl-PEG7 cleavage by carboxy peptidase B.
Figure 8:
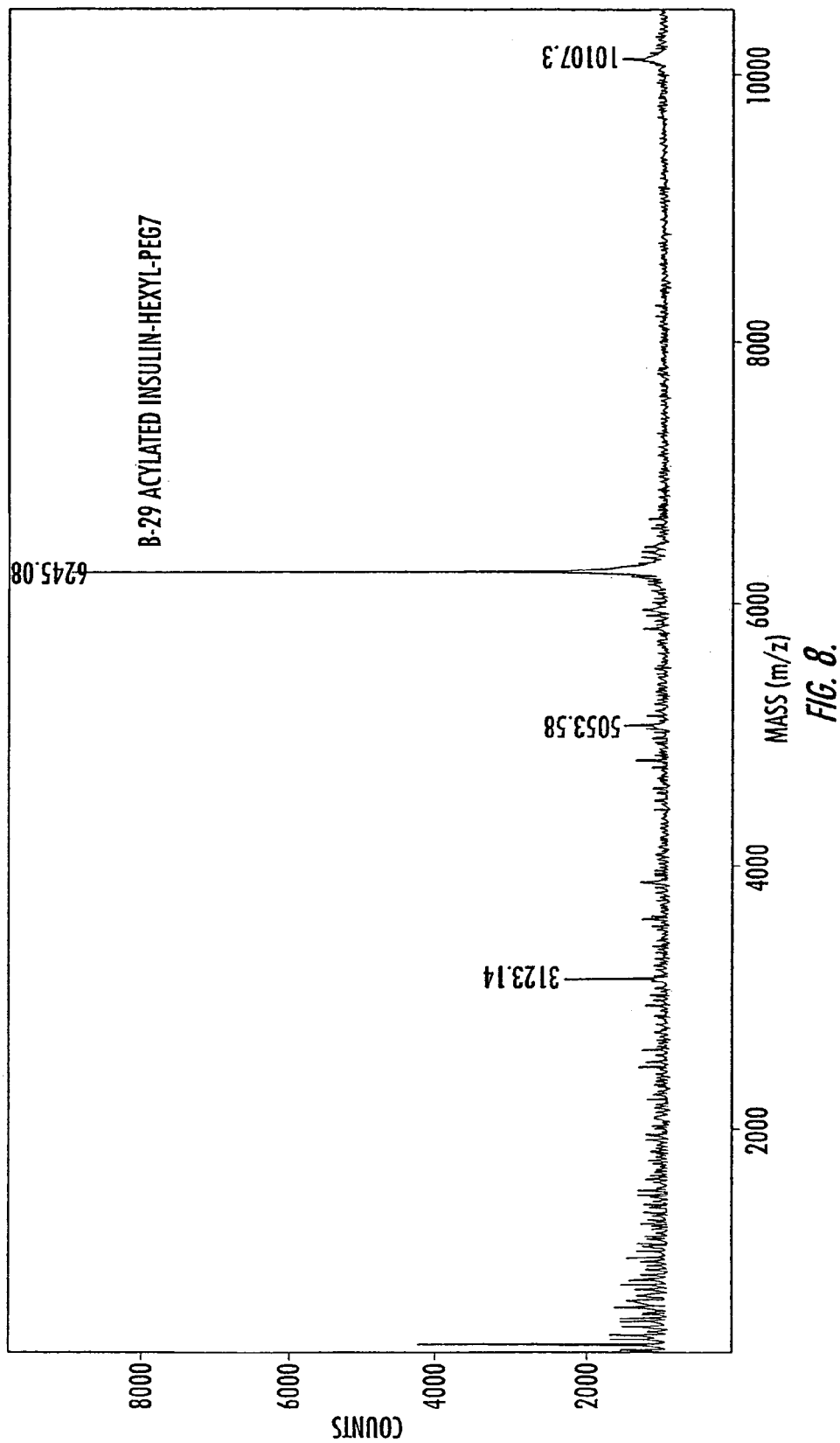
FIG. 8 illustrates an m.s. spectrum of the product of carboxypeptidase cleavage of B-29 acylated Insulin(Arg$^{31}$)-hexyl-PEG7 conjugate.

An aliquot of the reaction mixture of $Lys^{B29}$-hexyl-PEG7-oligomer-conjugated Insulin($Arg^{31}$) (3.10×10$^{-5}$ mmol) from Example 19 was removed. A solution of carboxypeptidase B (from porcine pancreas) was prepared in 100 mM Tris-HCl buffer pH 7.6. Carboxypeptidase B (1.03×10$^{-7}$) was added to the reaction mixture. Reaction was allowed to continue for 15 hours, and then was quenched with addition of 1% trifluoroacetic acid in acetonitrile. After processing, the products of the reaction were analyzed by HPLC. Retention time and mass spectral analysis were used to determine identity. Insulin (23%) and $Lys^{B29}$-hexyl-PEGn-oligomer-conjugated insulin (60%) (FIGS. 5, 7-8) were produced from the reaction of Proinsulin II monoconjugate. The expected products of the Proinsulin II diconjugate reaction are illustrated in Table 6.

TABLE 6

| Conjugate | Products (Expected Products) | Yield |
|---|---|---|
| Proinsulin II Mono | Insulin and | 23% |
| | $Lys^{B29}$-hexyl-PEGn-oligomer-conjugated Insulin | 60% |
| Proinsulin II Di | ($Lys^{B29}$-Hexyl-PEGn-oligomer-conjugated Insulin) | |

Example 21

Preparation of $Lys^{B29}$-Oligomer-Conjugated Insulin (a) Conjugation of Natural Human Proinsulin. Natural human proinsulin (Sigma Chemical Co.) (3.20×10$^{-4}$ mmol) is dissolved in 5 mL of DMSO. To the solution is added 45 μL of triethylamine. The solution is allowed to stir for 5 minutes before a solution of activated PEG7-hexyl oligomer (6.4×10$^{-4}$ mmol) in acetonitrile is added. After the reaction has progressed such that HPLC analysis indicates that the proinsulin has been consumed (or the concentration of proinsulin is no longer decreasing), the reaction is quenched by addition of 0.5 mL of 5% aqueous trifluoroacetic acid solution. The reaction mixture is then processed and exchanged into 100 mM Tris-HCl Buffer, pH 7.6.

(b) Enzyme Cocktail Cleavage of Oligomer-Conjugated Natural Proinsulin. An aliquot of the Tris-HCl solution of the product mixture from Example 21(a) is analyzed by HPLC to determine the polypeptide concentration therein. A solution of trypsin (TPCK treated; from bovine pancreas) is prepared in 100 mM Tris-HCl Buffer, pH 7.6. A solution of carboxypeptidase B (from porcine pancreas) is prepared in 100 mM Tris-HCl Buffer, pH 7.6. The crude mixture (1 mol eq.) is then allowed to react with trypsin (1.39×10$^{-3}$ mol eq) and carboxypeptidase B (4.56×10$^{-4}$ mol eq.). After 30 minutes, the reaction is quenched by addition of 1% trifluoroacetic acid in acetonitrile. The product mixture of the reaction is processed and analyzed by HPLC. Retention time (versus that of reference standards) and mass spectral analysis are used to determine identity. The expected products of the reaction are Insulin and $Lys^{B29}$-hexyl-PEG7-oligomer-conjugated Insulin.

Example 22

Isolation of the Products of Conjugation of Natural Human Proinsulin

Each major product obtained from the conjugation reaction described in Example 11(a) is isolated using reversed-phase HPLC. A column (1.0 cm. i.d.×25 cm. length) is packed with a commercially available C18 stationary phase known to be useful for the resolution of polypeptides and proteins, and then is incorporated into an HPLC system. The system is equilibrated with elution buffer that comprises a mixture of 75% mobile phase A (H2O with 0.1% trifluoroacetic acid) and 25% mobile phase B (acetonitrile with 0.1% trifluoroacetic acid). The Tris-HCl solution of the product mixture from Example 21(a) is applied to the column, and the major products are separated and eluted using a gradient elution in which the percentage of the acetonitrile component is increased from 25%-35% over 120 minutes. Fractions are collected and analyzed by HPLC to determine the identity and purity of the product therein. Common fractions of each product are pooled, and the solvent is removed by rotary evaporation. The identity and purity of each product peak are determined by HPLC and mass spectrometry. The expected products consist of 2 human Proinsulin monoconjugates, 1 human Proinsulin diconjugate and 1 human Proinsulin triconjugate.

Example 23

Enzyme Cocktail Cleavage of Isolated Conjugates of Natural Human Proinsulin

Each conjugate that is obtained using the procedure described in Example-22 is dissolved in 100 mM Tris-HCl Buffer, pH 7.6, and the resulting solution is analyzed by HPLC to determine the polypeptide concentration therein. A solution of trypsin (TPCK treated; from bovine pancreas) is prepared in 100 mM Tris-HCl Buffer, pH 7.6. A solution of carboxypeptidase B (from porcine pancreas) is prepared in 100 mM Tris-HCl Buffer, pH 7.6. The crude mixture (1 mol eq.) is then allowed to react with trypsin (1.39×10$^{-3}$ mol eq.) and carboxypeptidase B (4.56×10$^{-4}$ mol eq.). After 30 minutes, the reaction is quenched by addition of 1% trifluoroacetic acid in acetonitrile. The products are processed and analyzed by HPLC. Retention time (compared to that of reference standards) and mass spectral analysis are used to determine identity. The expected products of the reaction are Insulin or Lys$^{B29}$-hexyl-PEG7-oligomer-conjugated Insulin.

Example 24

Trypsin Cleavage of Isolated Conjugates of Natural Human Proinsulin

Each conjugate that is obtained as described in Example 22 is dissolved in 100 mM Tris-HCl Buffer, pH 7.6, and the resulting solution is analyzed by HPLC to determine the polypeptide concentration therein. A solution of trypsin (TPCK treated; from bovine pancreas) is prepared in 100 mM Tris-HCl Buffer, pH 7.6. The conjugate (300 mol eq.) is then allowed to react with trypsin (1 mol eq). After 20 minutes, reaction is quenched by addition of 1% trifluoroacetic acid in acetonitrile. The products are processed and analyzed by HPLC. Retention time and mass spectrometry are used to determine identity. The expected products of the reaction are Insulin(Arg$^{31}$) or Lys$^{B29}$-hexyl-PEG7-oligomer-conjugated Insulin(Arg$^{31}$).

Example 25

Carboxypeptidase B Cleavage of Trypsin Cleavage Mixture

An aliquot of the reaction mixture of Lys$^{B29}$-hexyl-PEG7-oligomer-conjugated Insulin(Arg$^{31}$) (300 mmol) from Example 24 is removed. A solution of carboxypeptidase B (from porcine pancreas) is prepared in 100 mM Tris-HCl buffer, pH 7.6. Carboxypeptidase B (1 mmol) is added to the reaction mixture. Reaction is allowed to continue for 15 hours, and then is quenched with addition of 1% trifluoroacetic acid in acetonitrile. The products are processed and analyzed by HPLC. Retention time and mass spectral analysis are used to determine identity. The expected products are Insulin or Lys$^{B29}$-hexyl-PEG7-oligomer-conjugated Insulin.

Example 26

Optimized Preparation of Lys$^{B29}$-Oligomer-Conjugated Insulin

Analysis of the experimental data from Example 11 indicated that Lys$^{B29}$-hexyl-PEG7-oligomer-conjugated Insulin and Lys-hexyl-PEG7-oligomer-conjugated C-peptide could be obtained in high yield and purity by (a) acylating the ε-amino group of all lysine residues that are present on a proinsulin raw material, and (b) cleaving the resulting, fully oligomer-conjugated proinsulin with an enzyme cocktail made up of trypsin and carboxypeptidase B. Experimental confirmation of this hypothesis was obtained as follows.

(a) Conjugation of Recombinant Proinsulin I. Recombinant Proinsulin I (MW 10,642 Daltons) is obtained from Biobras, Belo Horizonte, Brazil. A 2.32×10$^{-3}$ mmol portion of proinsulin I is dissolved in 10 mL of DMSO. To the solution is added 324 μL of triethylamine. The resulting solution is allowed to stir for 5 minutes, and then a solution of activated methylheptaethylene glycol(PEG7)-hexyl oligomer (4-6 mol eq.; sufficient to covert all Proinsulin I to the triconjugate) in acetonitrile is added. The course of the conjugation (acylation) reaction is monitored by HPLC. When reaction appears to be complete (i.e., no unconjugated Proinsulin I is observed by HPLC), it is quenched by addition of 3.54 mL of 5% aqueous trifluoroacetic acid solution. The reaction mixture is then processed and exchanged into 100 mM Tris-HCl Buffer, pH 7.6. The HPLC profile of the product mixture, oligomer-conjugated recombinant Proinsulin I, is expected to show peaks corresponding to triconjugate (all Lys and N-terminus conjugated) and diconjugate only.

(b) Enzyme Cocktail Cleavage of Oligomer-Conjugated Recombinant Proinsulin I. An aliquot of the Tris-HCl solution of the product mixture from Example 16(a) is analyzed by HPLC to determine the polypeptide concentration. A solution of trypsin (TPCK treated; from bovine pancreas) is prepared in 100 mM Tris-HCl Buffer, pH 7.6. A solution of carboxypeptidase B (from porcine pancreas) is prepared in 100 mM Tris-HCl Buffer, pH 7.6. The product mixture from Example 16(a) (0.424 μmol/mL) is then allowed to react with trypsin (5.97×10$^{-4}$ μmol/mL) and carboxypeptidase B (1.93×10$^{-4}$ μmol/mL). After 30 minutes, the reaction is quenched by the addition of 1.58 mL of 1% trifluoroacetic acid in acetonitrile. The major products are identified by HPLC retention time (relative to the retention times of known reference standards) and mass spectral analysis. Lys$^{B29}$-Hexyl-PEG7-Oligomer-Conjugated Insulin, the only insulin conjugate that is present, is expected to be obtained in near 95% yield. Lys$^{1}$-Hexyl-PEG7-Oligomer-Conjugated C-peptide is also obtained in near quantitative yield.

The present invention has been described herein with reference to its preferred embodiments. These embodiments do not serve to limit the invention, but are set forth for illustrative purposes. The scope of the invention is defined by the claims that follow.

That which is claimed is:

1. A method of synthesizing an insulin polypeptide-oligomer conjugate comprising:

contacting a proinsulin polypeptide comprising an insulin polypeptide coupled to one or more peptides by peptide bond(s) capable of being cleaved to yield the insulin polypeptide with an oligomer comprising the structure of Formula II:

$$A-X(CH_2)_m Y(C_2H_4O)_n R \qquad (II)$$

wherein:

A is —C(O)—OH, C(S)—OH, —C(S)—SH, —OH, —SH, or NH$_2$;

X is an oxygen atom or a covalent bond, with the proviso that X is not an oxygen atom when A is —OH;

Y is an ester, an ether, a carbamate, a carbonate, or an amide bonding moiety;

m is between 1 and 30;

n is between 1 and 50; and

R is an alkyl moiety, a sugar moiety, cholesterol, adamantane, an alcohol moiety, or a fatty acid moiety;

under conditions sufficient to couple the oligomer to the insulin polypeptide portion of the proinsulin polypeptide and provide a proinsulin polypeptide-oligomer conjugate; and cleaving the one or more peptides from the proinsulin polypeptide-oligomer conjugate to provide the insulin polypeptide-oligomer conjugate.

2. The method according to claim 1, wherein the contacting of the proinsulin polypeptide to the oligomer comprises:

contacting the oligomer with an activating agent under conditions sufficient to provide an activated oligomer capable of coupling to a nucleophilic functionality on the proinsulin polypeptide; and contacting the activated oligomer with the proinsulin polypeptide under conditions sufficient to provide the proinsulin polypeptide-oligomer conjugate.

3. The method according to claim 2, wherein the contacting of the oligomer with the activating agent and the contacting of the activated oligomer with the proinsulin polypeptide is performed in situ.

4. The method according to claim 2, wherein the molar ratio of activated oligomer to proinsulin polypeptide is greater than about 1:1.

5. The method according to claim 2, wherein the molar ratio of activated oligomer to proinsulin polypeptide is greater than about 3:1.

6. The method according to claim 2, wherein the molar ratio of activated oligomer to proinsulin polypeptide is greater than about 4:1.

7. The method according to claim 6, wherein the yield of insulin polypeptide-oligomer conjugate is greater than 75 percent.

8. The method according to claim 6, wherein the yield of insulin polypeptide-oligomer conjugate is greater than 80 percent.

9. The method according to claim 6, wherein the yield of insulin polypeptide-oligomer conjugate is greater than 85 percent.

10. The method according to claim 6, wherein the yield of insulin polypeptide-oligomer conjugate is greater than about 90 percent.

11. The method according to claim 6, wherein the yield of insulin polypeptide-oligomer conjugate is greater than about 95 percent.

12. The method according to claim 1, wherein the yield of insulin polypeptide-oligomer conjugate is greater than 75 percent.

13. The method according to claim 1, wherein the yield of insulin polypeptide-oligomer conjugate is greater than 80 percent.

14. The method according to claim 1, wherein the yield of insulin polypeptide-oligomer conjugate is greater than 85 percent.

15. The method according to claim 1, wherein the yield of insulin polypeptide-oligomer conjugate is greater than about 90 percent.

16. The method according to claim 1, wherein the yield of insulin polypeptide-oligomer conjugate is greater than about 95 percent.

17. The method according to claim 1, wherein the insulin polypeptide has an A-chain polypeptide and a B-chain polypeptide, and wherein the one or more peptides comprise a connecting peptide coupled at a first end to the C-terminus of the B-chain polypeptide and coupled at a second end to the N-terminus of the A-chain polypeptide.

18. The method according to claim 17, wherein the connecting peptide is a C-peptide polypeptide.

19. The method according to claim 17, wherein the connecting peptide is C-peptide.

20. The method according to claim 17, wherein the connecting peptide is devoid of lysine residues.

21. The method according to claim 17, wherein the one or more peptides further comprise a leader peptide coupled to the N-terminus of the B-chain polypeptide.

22. The method according to claim 21, wherein the leader peptide is devoid of lysine residues.

23. The method according to claim 1, wherein the proinsulin polypeptide is proinsulin.

24. The method according to claim 1, wherein the proinsulin polypeptide is proinsulin coupled at the N-terminus of the B-chain to a leader peptide by a peptide bond that is cleavable.

25. The method according to claim 1, wherein the insulin polypeptide is insulin.

26. The method according to claim 25, wherein the oligomer is coupled to the lysine at the B29 position of the insulin.

27. The method according to claim 1, wherein the insulin polypeptide-oligomer conjugate is amphiphilically balanced.

28. The method according to claim 1, wherein the polyalkylene glycol moiety is a polyethylene glycol moiety.

29. The method according to claim 1, wherein m is between 3 and 16.

30. The method according to claim 1, wherein m is between 4 and 14.

31. The method according to claim 1, wherein m is between 5 and 10.

32. The method according to claim 1, wherein n is between 3 and 18.

33. The method according to claim 1, wherein n is between 4 and 14.

34. The method according to claim 1, wherein n is between 5 and 10.

35. The method according to claim 1, wherein R is lower alkyl.

36. The method according to claim 1, wherein R is $C_1$ to $C_3$ alkyl.

37. The method according to claim 1, wherein R is methyl.

38. The method according to claim 1, wherein the cleaving of the one or more peptides from the proinsulin polypeptide-oligomer conjugate comprises contacting the proinsulin polypeptide-oligomer conjugate with one or more enzymes that are capable of cleaving the bond(s) between the one or more peptides and the insulin polypeptide under conditions sufficient to cleave the one or more peptides from the proinsulin polypeptide-oligomer conjugate.

39. The method according to claim 38, wherein the one or more enzymes are selected from the group consisting of trypsin, carboxy peptidase B, and mixtures thereof.

40. The method according to claim 17, wherein the connecting peptide has a terminal amino acid residue at the first end, and wherein the cleaving of the connecting peptide from the proinsulin-oligomer conjugate comprises:
   contacting the proinsulin polypeptide-oligomer conjugate with a first enzyme under conditions sufficient to provide a terminal amino acid residue-insulin polypeptide-oligomer conjugate; and
   contacting the terminal amino acid residue-insulin polypeptide-oligomer conjugate with a second enzyme under conditions sufficient to provide the insulin-oligomer conjugate.

41. The method according to claim 40, wherein the terminal amino acid residue is an arginine residue.

42. The method according to claim 41, wherein the insulin polypeptide is insulin, and wherein the connecting peptide is human C-peptide.

43. The method according to claim 40, wherein the contacting of the proinsulin-oligomer conjugate with a first enzyme and the contacting of the terminal amino acid residue-insulin polypeptide-oligomer conjugate with a second enzyme occur substantially concurrently.

44. The method according to claim 43, wherein the first enzyme and the second enzyme are provided in a mixture comprising the first enzyme and the second enzyme.

45. The method according to claim 40, wherein the first enzyme is trypsin, and wherein the second enzyme is carboxy peptidase B.

* * * * *